United States Patent [19]

Oshiro et al.

[11] Patent Number: 5,786,367
[45] Date of Patent: Jul. 28, 1998

[54] CYCLIC AMIDE DERIVATIVES

[75] Inventors: Yasuo Oshiro, Tokushima; Tatsuyoshi Tanaka; Takao Nishi, both of Itano-gun; Keiichi Kuwahara, Ako; Shigeki Fujisawa, Takasago; Keiko Takasu, Himeji; Yutaka Wada, Ako, all of Japan

[73] Assignee: Otsuka Pharmaceutical Co., Ltd., Tokyo, Japan

[21] Appl. No.: 600,987

[22] PCT Filed: Jul. 12, 1995

[86] PCT No.: PCT/JP95/01392

§ 371 Date: Mar. 5, 1996

§ 102(e) Date: Mar. 5, 1996

[87] PCT Pub. No.: WO96/02508

PCT Pub. Date: Feb. 1, 1996

[30] Foreign Application Priority Data

Jul. 14, 1994 [JP] Japan ................. 6-161639

[51] Int. Cl.$^6$ ................. A61K 31/47; C07D 215/227
[52] U.S. Cl. ................. 514/312; 546/153; 546/157; 546/158
[58] Field of Search ................. 546/153, 157, 546/158; 514/312

[56] References Cited

U.S. PATENT DOCUMENTS 5,081,044  1/1992  Buckler et al. ................. 436/135
5,576,324  11/1996  Kyotani et al. ................. 514/291

FOREIGN PATENT DOCUMENTS

| 59-175468 | 10/1984 | Japan. |
| 60-209567 | 10/1985 | Japan. |
| 63-168403 | 7/1988 | Japan. |
| 63-230687 | 9/1988 | Japan. |
| 63-258903 | 10/1988 | Japan. |
| 63-290821 | 11/1988 | Japan. |
| 4346974 | 12/1992 | Japan. |
| WO 93/22317 | 11/1993 | WIPO. |

OTHER PUBLICATIONS

CA 123: 164215, 1995.
CA 89(19): 163810r—1978.
CA 90(3): 23348s—1978.
CA 90(5): 39080j—1978.
CA 93(25): 239721t—1980.
CA 94(11): 84337s—1980.
CA 94(21): 175334e—1980.
CA 95(25): 219961j—1981.
CA 96(15): 123047k—1982.
CA 98(25): 212803n—1982.
CA 99(9): 71039z—1983.
CA 100(1): 6901z—1983.
CA 100(25): 206492d—1984.
CA 101(15): 126820q—1984.
CA 103(1): 6548b—1984.
CA 104(7): 50765q—1985.
CA 105(7): 60788j—1985.
CA 106(15): 116465s—1986.
CA 107(23): 217504e—1986.
CA 108(25): 221701e—1987.
CA 109(15): 125871k—1988.
CA 111(19): 174468j—1988.
CA 116(5): 41269b—1991.
CA 119(15): 156247x—1993.
Guiotto et al., CA 123: 164215 (Jun. 6, 1995).

*Primary Examiner*—Yogendra N. Gupta
*Attorney, Agent, or Firm*—Finnegan, Henderson, Farabow, Garrett & Dunner

[57] ABSTRACT

The present invention provides novel cyclic amide derivatives having activity for protecting against the ultraviolet rays, activity for scavenging active oxygen species and activity for inhibiting the formation of lipid peroxides, which is represented by the following general formula (1):

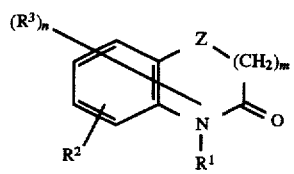

wherein $R^2$ is a hydroxyl group, a lower alkenyloxy group, a phenyl-lower alkenyloxy group, a cycloalkenyloxy group, a tetrahydropyranyloxy group, a pyridyloxy group, or a lower alkanoyloxy group which may have carboxyl group(s).

23 Claims, No Drawings

CYCLIC AMIDE DERIVATIVES

FIELD OF THE INDUSTRIAL UTILIZATION

The present invention relates to novel cyclic amide derivatives and salts thereof.

BACKGROUND ART

The sunlight is indispensable environmental factor to the living body, while at the same time the sunlight is harmful to the living body. The skin and eyes are contacted continuously with oxygen in the air, additionally these organs are unavoidably encountered in the environment where active oxygen species and lipid peroxides are formed easily by physical reactions caused by direct effect of the ultraviolet rays and radiations, and by chemical reactions in the presence of the sebum and other chemical substances. (Cf. Pharma. Medica., 1990, Vol. 8, No. 4, pp. 67–71). Harmful effects caused by the sunlight to the living body are mostly made on the basis of actions of ultraviolet rays. Among the ultraviolet rays, ultraviolet ray-C has the highest energy level and shows strong germicidal activity, and is also known that it accelerates the cancerization. Ultraviolet ray-C is absorbed in the ozonosphere in the stratosphere surrounding the earth, so that very little amount of ultraviolet ray-C only reaches the earth ground. Ultraviolet ray-A causes pigmentation of the skin due to increase of melanin formation in the skin. Ultraviolet ray-B causes sunburn, such as "feel hot" and varicella, and it has been known that the skin cancerization may be caused by long hour-exposure to the ultraviolet ray-B. (Cf. Active oxygen . Free radicals, 1993, Vol. 4, pp. 20–22).

In recent years, it has been well known as the fact that the cancerization tends to upward by increasing of irradiated amount of ultraviolet ray-B due to destruction of the ozonosphere. These disturbances and injuries of the living body caused by ultraviolet rays are presumed on the basis of various active oxygen radicals which are formed by exposure to the ultraviolet rays.

Formation of the active oxygen species caused by exposure to the ultraviolet rays is proposed as two types of mechanisms as follows. That is, one type of the mechanism is that the substrate (e.g., lipid) is oxidized and/or reduced by reacting with excited state of sensitized materials which are excited by action of the ultraviolet rays or lights. Then, oxygen is added to the substrate, which is changed to radical state, to form peroxide (lipid peroxide). Further, oxygen anion radicals are formed by transformation of electrons from the radical to oxygen. Another type of formation mechanism is that the sensitized materials in excited state are first reacted with oxygen, so that energy or electron transfer causes the formation of singlet oxygen or oxygen anion radical. Furthermore, hydrogen peroxide is formed from oxygen anion radical by disproportionation, and hydroxy radicals are also formed by Fenton reaction (Cf. Active Oxygen . Free Radicals, 1993, Vol. 4, pp. 6–19).

Pharmaceutical chemicals which possess activities for scavenging these oxygen radicals can be used as agents for prevention and treatment of various injuries and diseases caused by the ultraviolet rays. In addition to the above, superoxide dismutases (SOD), which act disproportionation against oxygen anion radicals, present in the living bodies (Cf. Journal of Investigative Dermatology, 1984, Vol. 83, pp. 166–168), and there are known some agents for preventing and treating dermatological injuries which are caused by active oxygen species present in the living bodies [Cf. Hifuka Kiyou (Bulletin of Dermatology (Japan)), 1987, Vol. 82, No. 2, pp. 179–182]. Glutathione is known that it possesses activity for scavenging alkoxy radicals, so that it is used as treating agent of cataract. Vitamin E possesses skin protection activity (Cf. Fragrance Journal, 1991, No. 8, pp. 28–33). Vitamin C possesses anti-oxidation activity, and is known that it is effective to prevention of pigmentation (Cf. Fragrance Journal and Biophysics, 1992, Vol. 296, No. 2, pp. 575–582; Journal of Dermatology, 1990, Vol. 17, pp. 595–598). However, it should be noted the fact that, because SOD and glutathione are endgenous substances, they have some problems in stabilities thereof and raw materials obtained therefor are not easily available. Also, these vitamins have problems because their stabilities and the effects in vivo are not good enough.

In view of these circumstances, the present inventors have made extensive research works and as the result that the present invention have successfully completed based on the finding of the facts that the cyclic amide derivatives of the present invention possess effective scavenging activities against active oxygen species, and said cyclic amide derivatives clearly show the activities for decreasing and removing lipid superoxides, which are formed increasingly in the living bodies, by irradiation of ultraviolet rays.

DISCLOSURE OF THE INVENTION

The cyclic amide derivatives of the present invention are novel compounds which have not been known in any literature, and are represented by the general formula (1) as follows:

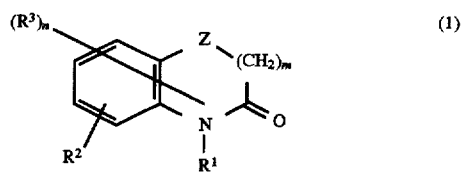

wherein $R^2$ is a hydroxyl group, a lower alkenyloxy group, a phenyl-lower alkenyloxy group, a cycloalkenyloxy group, a tetrahydropyranyloxy group, a pyridyloxy group, or a lower alkanoyloxy group which may have carboxy group(s);

$R^3$ is a lower alkenyl group;

Z is an oxygen atom, a sulfur atom, a group of —$CH_2$—, or a group of —CH=CH—;

n is an integer of 1 to 3;

m is 0 or 1; provided that when Z is a group of —CH=CH—, then m is 0;

$R^1$ is a hydrogen atom, an alkyl group, an alkenyl group, a phenyl-lower alkenyl group, a cycloalkyl-lower alkyl group, a phenyl group which may have, in the phenyl ring, substituent(s) selected from the group consisting of a lower alkoxy group and a halogen atom, a hydroxyl group-substituted alkyl group, a halogen-substituted lower alkyl group, a cycloalkenyl group; a lower alkynyl group, a phenyl-lower alkyl group which may have, on the phenyl ring, 1 to 3 substituents selected from the group consisting of a lower alkenyloxy group, a lower alkoxy group, a lower alkenyl group, a hydroxyl group, a lower alkyl group, a carboxyl group, a lower alkoxycarbonyl group and a group of the formula:

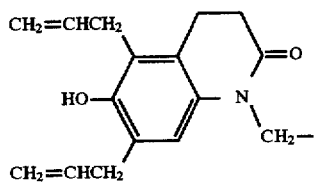

a naphthyl-substituted lower alkyl group, a phthalimido-substituted lower alkyl group, a lower alkoxycarbonyl-substituted lower alkyl group, a group of the formula:

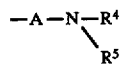

(wherein A is a lower alkylene group; $R^4$ and $R^5$ are the same or different, and are each a hydrogen atom, a carbamoyl group, a lower alkanoyl group which may have halogen atom(s), a phenylsulfonyl group which may have, in the phenyl ring, lower alkyl group(s) as substituent(s), a lower alkoxy-lower alkyl group, a lower alkyl group, a hydroxyl group-substituted lower alkyl group, a lower alkoxycarbonyl-substituted lower alkyl group, or a carboxy-substituted lower alkyl group; further $R^4$ and $R^5$ may form 5- or 6-membered saturated or unsaturated hetero-cyclic group by combining to each other, together with the adjacent nitrogen atom being bonded thereto, further with or without other nitrogen atom or oxygen atom; said heterocyclic group may have, as substituent(s) selected from the group consisting of a carbamoyl group, a carboxyl group, a cycloalkyl group and a phenyl group which may have halogen atom(s) as substituent in the phenyl ring);

a lower alkanoyloxy-lower alkyl group, a cyano group-substituted lower alkyl group, a group of the formula:

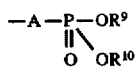

(wherein, A is a lower alkylene group; $R^9$ and $R^{10}$ are the same or different, and are each a hydrogen atom or a lower alkyl group), a carboxy-substituted lower alkyl group, a lower alkoxycarbonyl-substituted lower alkyl group or a carbamoyl-substituted lower alkyl group.

An object of the present invention is to provide cyclic amide derivatives and salt thereof, having activity for protecting injuries from ultraviolet rays, activity for scavenging active oxygen radicals, activity for inhibiting formation of lipid peroxides, and they are useful as active ingredients to be contained in pharmaceutical composition, medicines of external use, eye lotion, medicated cosmetics and common cosmetics for preventing and treating various diseases caused by exposure to ultraviolet rays, contact with active oxygen species and lipid peroxides.

As to the active oxygen species, there can be exemplified hydroxy radical, alkoxy radical, hydroperoxy radical, peroxy radical, superoxide, hydrogen peroxide, hydroperoxide, singlet oxygen, ozone and others.

The cyclic amide derivatives of the present invention clearly inhibit the formation of lipid peroxides in the skin caused by exposure to ultraviolet rays. Furthermore, the cyclic amide derivatives of the present invention trap a radical from diphenylpicrylhydrazyl, which is understood as a typical model of lipid peroxides. For these reasons, the cyclic amide derivatives of the present invention are useful as agents for preventing and treating various dermatological injuries and various diseases which are caused by ultraviolet rays, active oxygen species, radicals and lipid peroxides, as well as agent for preventing aging of the skin [Cf. Hifubyo Shinryo (Treatment of Dermatitis (Japan)), 1991, Vol. 13, No. 3, pp. 201–205; Fragrance Journal, 1993, No. 11, pp. 35–42]. For example, the cyclic amide derivatives of the present invention are useful as agents for preventing and treating solar dermatitis, precancerous lesions of the skin (containing solar keratosis), malignant tumors of the skin, hyperpigmentation such as melasma, ephelides, senile pigment freckle, pigmentatio petaloides actinica; chronic actinic dermatoses such as sailor's skin, farmer's skin, cutis rhomboidalis nuchae, cheilitis actinica, senile atrophy, seborrheic keratosis; photocontact dermatitis, berlick dermatitis, skin vascular inflammation, erythema multiforme, Bechcet's disease, varicella dermatitis, cement dermatitis, neurodermatitis, eczema, pruritus around anal or genital region, dermatitis of human beings, skin diseases of mammals other than human beings (e.g., pet animals such as dogs and cats, and domestic cattles such as cows and horses), photosensitive dermatoses such as photosensitizing drug eruption, polymorphous light eruption, hydroa vacciniforme, solar urtiaria and porphyria, and burn injury (Burns, 1989, Vol. 15, No. 5, pp. 291–294 and Ibid., 1992, Vol. 18, No. 2, pp. 127–131); keloid, comedo, atopic dermatitis, contact dermatitis, diaper dermatitis, seborrheic dermatitis, autosensitization dermatitis, stasis dermatitis, urticaria, prurigo, pruritus cutaneous, keratosis such as psoriasis, lichen planus, follicular keratosis, pityriasis, and used as cosmetics and medicines for external use (including medicated cosmetics) for protection of sunburn, prevention of melasma and ephelides caused by sunburn, prevention of wrinkles, aging of the skin and photoaging; and also useful as active ingredient for quasi-drugs (Cf. Active Oxygen . Free Radicals, 1992, Vol. 3, pp. 306–311). In addition to the activity for scavenging active oxygen species, the cyclic amide derivatives of the present invention are useful as agent for preventing cataract because they possess excellent property of transference to the aqueous humor (Cf. Active Oxygen . Free Radicals, 1993, Vol. 4, pp. 20–26).

The cyclic amide derivatives of the present invention are useful as agents for preventing and treating various disturbances and diseases other than those mentioned above, caused by active oxygen radicals. As to the agents for preventing and treating various disturbances and diseases, for example, agent of antiarteriosclerosis, agent for preventing cancerization, carcinostatic agent, antiiflammatory agent, analgesic, agent for treating autoimmune diseases, agent for inhibiting aggregation of platelets, hypotensive agent, antihyperlipidemia agent and agent for preventing and treating retinopathy of prematurity. Further, the cyclic amide derivatives of the present invention are useful as agents for treating diseases of various organs, for example the heart, the kidney, the digestive tract, the brain, ischematic diseases in the nervous system, ischematic heart diseases such as myocardial infarction and arrhythmia; agents for improving disturbances of hepatic and renal functions caused by transplantation and microcirculation disfunction; agents for treating digestive tract ulcers such as gastric ulcer; agents for treating cerebral hemorrhage, cerebral infarction and transient ischematic cerebral attack; agents for treating disturbances such as decreasing the number of leukocytes, alopecia, reddening of the skin, vomiting, anorexia and the like which are caused by exposure to radiations such as X ray, α ray, β ray, γ ray, neutron beam, accelerated electron beam and the like; agents for treating diabetes mellitus, ophthalmological diseases such as siderosis of eyeball, retinitus and the like; pigmentation, sepsis, pulmonary edema, adult respiratory distress syndrome, common arthritis, malignant rheumatic arthritis, ulcerative colitis, Crohn's disease, Parkinson's disease and Raynau's disease, as well as burn injury, external injury, fatigue and the like. Furthermore, the cyclic amide derivatives of the present invention are useful not only as use of the above-mentioned pharmaceutical applications, but also effective as use of other industrial fields such as antioxidation agents for oils and fats being contained in processed food products and the like.

In the present specification, concrete examples of the substituents are shown as follows.

As to the lower alkenyloxy group, a straight chain- or branched chain-alkenyloxy group having 2 to 6 carbon atoms, such as vinyloxy, allyloxy, 2-butenyloxy, 3-butenyloxy, 1-methylallyloxy, 2-pentenyloxy and 2-hexenyloxy groups can be exemplified.

As to the phenyl-lower alkenyloxy group, a phenyl-alkenyloxy group in which the alkenyl moiety is a straight chain- or branched chain-alkenyl group having 2 to 6 carbon atoms, such as styryloxy, cinnamyloxy, 2-phenyl-2-butenyloxy, 3-phenyl-3-butenyloxy, 1-methyl-2-phenylallyloxy, 5-phenyl-2-pentenyloxy and 6-phenyl-2-hexenyloxy groups can be exemplified.

As to the cycloalkenyloxy group, a cycloalkenyloxy group having 3 to 8 carbon atoms, such as cyclopropenyloxy, cyclobutenyloxy, cyclopentenyloxy, cyclohexenyloxy, cycloheptenyloxy and cyclooctenyloxy groups can be exemplified.

As to the lower alkanoyloxy group which may have carboxyl group(s) as the substituent(s), a straight chain- or branched chain-alkanoyloxy group having 1 to 6 carbon atoms which may have 1 to 3 carboxyl groups as the substituents, such as formyloxy, acetyloxy, propionyloxy, butyryloxy, isobutyryloxy, pentanoyloxy, tert-butylcarbonyloxy, hexanoyloxy, 2-carboxyacetyloxy, 2,2-dicarboxyacetyloxy, 3,3,3-tricarboxypropionyloxy, 3-carboxypropionyloxy, 4,4,4-tricarboxybutyryloxy, 4-carboxybutyryloxy, 5-carboxypentanoyloxy, 3-carboxy-2-methylpropionyloxy, 6-carboxyhexanoyloxy and 5,6-dicarboxyhexanoyloxy groups can be exemplified.

As to the alkyl group, a straight chain- or branched chain-lower alkyl group having 1 to 6 carbon atoms, such as methyl, ethyl, propyl, isopropyl, butyl, tert-butyl, pentyl and hexyl groups can be exemplified, and a straight chain- or branched chain-alkyl group having 7 to 12 carbon atoms, such as heptyl, octyl, nonyl, decyl, undecyl, dodecyl, 3-ethylpentyl, 2,3,5-trimethylhexyl, and 5-methyl-4-propyloctyl groups can be exemplified.

As to the alkenyl group, a straight chain- or branched chain-alkenyl group having 2 to 11 carbon atoms and having 1 to 3 double bonding therein, such as vinyl, allyl, 3-methylbutenyl, 2-butenyl, 3-butenyl, 1-methylallyl, 2-pentenyl, 2-hexenyl, 1-heptenyl, 1-octenyl, 1-nonenyl, 1-decenyl, 1-undecenyl, 2-heptenyl, 3-heptenyl, 2-methyl-4-heptenyl, 2-methyl-5-heptenyl, 4-methyl-2-heptenyl, 3-methyl-1-heptenyl, 2,4-butadienyl, 1,3-pentadienyl, 2,4-hexadienyl, 1,3,5-hexatrienyl, 1,3-heptadienyl, 1,4-heptadienyl, 1,5-heptadienyl, 1,6-heptadienyl, 2,4-heptadienyl, 2-methyl-2,4-heptadienyl, 2,6-dimethyl-2,4-heptadienyl, 2,5-dimethyl-1,3-heptadienyl, 2,4,6-trimethyl-2,4-heptadienyl, 2-octenyl, 3-octenyl, 4-octenyl, 2-methyl-5-octenyl, 2-methyl-6-octenyl, 2-methyl-7-octenyl, 1,3-octadienyl, 1,4-octadienyl, 1,5-octadienyl, 1,6-octadienyl, 1,7-octadienyl, 2,4-octadienyl, 3,7-octadienyl, 4,8-dimethyl-3,7-octadienyl, 2,4,6-trimethyl-3,7-octadienyl, 3,4-dimethyl-2,5-octadienyl, 3,7-dimethyl-2,6-octadienyl, 4,8-dimethyl-2,6-octadienyl, 2-nonenyl, 3-nonenyl, 4-nonenyl, 2-methyl-5-nonenyl, 2-methyl-6-nonenyl, 2-methyl-7-nonenyl, 2-methyl-8-nonenyl, 1,3-nonadienyl, 1,4-nonadienyl, 1,5-nonadienyl, 1,6-nonadienyl, 1,7-nonadienyl, 1,8-nonadienyl, 2,4-nonadienyl, 3,7-nonadienyl, 4,8-dimethyl-3,7-nonadienyl, 2,4,6-trimethyl-3,7-nonadienyl, 3,4-dimethyl-2,5-nonadienyl, 4,8-dimethyl-2,6-nonadienyl, 2-decenyl, 3-decenyl, 4-decenyl, 5-decenyl, 2-methyl-6-decenyl, 3-methyl-7-decenyl, 4-methyl-8-decenyl, 5-methyl-9-decenyl, 1,3-decadienyl, 1,4-decadienyl, 1,5-decadienyl, 1,6-decadienyl, 1,7-decadienyl, 1,8-decadienyl, 1,9-decadienyl, 2-methyl-2,4-decadienyl, 3-methyl-2,5-decadienyl, 4,8-dimethyl-2,6-decadienyl, 2,4,6-trimethyl-3,7-decadienyl, 2,9-dimethyl-3,7-decadienyl, 2-undecenyl, 3-undecenyl, 4-undecenyl, 5-undecenyl, 2-methyl-6-undecenyl, 3-methyl-7-undecenyl, 4-methyl-8-undecenyl, 5-methyl-9-undecenyl, 2-methyl-10-undecenyl, 1,3-undecadienyl, 1,4-undecadienyl, 1,5-undecadienyl, 1,6-undecadienyl, 1,7-undecadienyl, 1,8-undecadienyl, 1,9-undecadienyl, 1,10-undecadienyl, 2-methyl-2,4-undecadienyl, 3-methyl-2,5-undecadienyl, 4,8-dimethyl-2,6-undecadienyl, 2,4,6-trimethyl-3,8-undecadienyl, 2,9-dimethyl-3,8-uecadienyl, 1,3,5-heptatrienyl, 2,4,6-octatrienyl, 1,3,6-nonatrienyl and 1,5,7-undecatrienyl groups can be exemplified.

As to the phenyl-lower alkenyl group, a phenyl-alkenyl group in which the alkenyl moiety is a straight chain- or branched chain-alkenyl group having 2 to 6 carbon atoms, such as styryl, cinnamyl, 2-phenyl-2-butenyl, 3-phenyl-3-butenyl, 1-methyl-2-phenylallyl, 5-phenyl-2-pentenyl and 6-phenyl-2-hexenyl group can be exemplified.

As to the cycloalkyl-lower alkyl group, a straight chain- or branched chain-alkyl group having 1 to 6 carbon atoms to which a cycloalkyl group having 3 to 8 carbon atoms is bonded, such as cyclopropylmethyl, 2-cyclobutylethyl, cyclopentylmethyl, 2-cyclopentyl-propyl, cyclohexylmethyl, 2-cyclohexylethyl, 3-cyclohexylpropyl, 4-cyclohexylbutyl, 3-cyclobutylpropyl, 1,1-dimethyl-2-cyclohexylethyl, 1-methyl-2-cyclopentylethyl, 2-cyclooctylethyl, 4-cyclohexylbutyl, 2-cyclopentylethyl, 2-cyclohexyl-propyl, 2-cycloheptylethyl, 5-cyclohexylpentyl and 6-cyclohexylhexyl groups can be exemplified.

As to the phenyl group which may have as substituents selected from the group consisting of a lower alkoxy group (s) and a halogen atom(s) in the phenyl ring, a phenyl group which may have 1 to 3 substituents selected from the group consisting of a straight chain- or branched chain-alkoxy group having 1 to 6 carbon atoms and a halogen atom in the phenyl ring, such as phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-hexyloxyphenyl, 3,4-dimethoxyphenyl, 3,4-diethoxyphenyl, 2,5-dimethoxyphenyl, 3,4,5-trimetoxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 4-iodophenyl, 3,5-dichlorophenyl, 2,6-dichlorophenyl, 3,4-dichlorophenyl, 3,4-difluorophenyl, 3,5-dibromophenyl, 3,4,5-trichlorophenyl and 2-ethoxy-4-chlorophenyl groups can be exemplified.

As to the hydroxyl group-substituted alkyl group, a straight chain- or branched chain-alkyl group having 1 to 11 carbon atoms to which 1 to 3 hydroxyl groups are substituted, such as hydroxymethyl, 2-hydroxyethyl, 3-hydroxypropyl, 2-hydroxypropyl, 2-hydroxyisopropyl, 2-hydroxybutyl, 3-hydroxybutyl, 4-hydroxybutyl, 5-hydroxypentyl, 2-hydroxypentyl, 3-hydroxypentyl, 4-hydroxypentyl, 6-hydroxyhexyl, 2-hydroxyhexyl, 3-hydroxyhexyl, 4-hydroxyhexyl, 1-methyl-2-hydroxyethyl, 1,1-dimethyl-2-hydroxyethyl, 1,2-dihydroxyethyl, 2,2-dihydroxyethyl, 1,3-dihydroxypropyl, 2,3-dihydroxypropyl, 1,2,3-trihydroxypropyl, 1,4-dihydroxybutyl, 2,4-dihydroxybutyl, 3,4-hydroxybutyl, 1,2-dihydroxybutyl, 2,3-dihydroxybutyl, 1,3-dihydroxybutyl, 2,2-dihydroxybutyl, 1,2,3-trihydroxybutyl, 2,3,4-trihydroxybutyl, 2,3-dihydroxypentyl, 3,4-dihydroxypentyl, 3,5-dihydroxypentyl, 3,4,5-trihydroxypentyl, 2,4,5-trihydroxypentyl, 2,3-dihydroxyhexyl, 3,4-dihydroxyhexyl, 3,5-dihydroxyhexyl, 3,4,5-trihydroxyhexyl, 2,4,5-trihydroxyhexyl, 7-hydroxyheptyl, 8-hydroxyoctyl, 9-hydroxynonyl, 10-hydroxydecanyl and 11-hydroxyundecanyl groups can be exemplified.

As to the halogen-substituted alkyl group, a straight chain- or branched chain-alkyl group having 1 to 6 carbon atoms to which 1 to 3 halogen atoms are substituted, such as chloromethyl, 2-chloroethyl, 3-chloropropyl, 2-chloropropyl, 2-chloroisopropyl, 2-chlorobutyl, 3-chlorobutyl, 4-chlorobutyl, 5-chloropentyl, 2-chloropentyl, 3-chloropentyl, 4-chloropentyl, 6-chlorohexyl, 2-chlorohexyl, 3-chlorohexyl, 4-chlorohexyl, 1-methyl-2-chloroethyl, 1,1-dimethyl-2-chloroethyl, 1,2-dichloroethyl, 2,2-dichloroethyl, 1,3-dichloropropyl, 2,3-dichloropropyl, 1,2,3-trichloropropyl, 1,4-dichlorobutyl, 2,4-dichlorobutyl, 3,4-dichlorobutyl, 1,2-dichlorobutyl, 2,3-dichlorobutyl, 1,3-dichlorobutyl, 2,2-dichlorobutyl, 1,2,3-trichlorobutyl, 2,3,4-trichlorobutyl, 2,3-dichloropentyl, 3,4-dichloropentyl, 3,5-dichloropentyl, 3,4,5-trichloropentyl, 2,4,5-trichloropentyl, 2,3-dichlorohexyl, 3,4-dichlorohexyl, 3,5-dichlorohexyl, 3,4,5-trichlorohexyl, 2,4,5-trichlorohexyl, bromomethyl, 2-bromoethyl, 3-boromopropyl, 2-bromopropyl, 2-bromoisopropyl, 2-bromobutyl, 3-bromobutyl, 4-bromobutyl, 5-bromopentyl, 2-bromopentyl, 3-bromopentyl, 4-bromopentyl, 6-bromohexyl, 2-bromohexyl, 3-bromohexyl, 4-bromohexyl, 1-methyl-2-bromoethyl, 1,1-dimethyl-2-bromoethyl, 1,2-dibromoethyl, 2,2-dibromoethyl, 1,3-dibromopropyl 2,3-dibromopropyl, 1,2,3-tribromopropyl, 1,4-dibromobutyl, 2,4-dibromobutyl, 3,4-dibromobutyl, 1,2-dibromobutyl, 2,3-dibromobutyl, 1,3-dibromobutyl, 2,2-dibromobutyl, 1,2,3-tribromobutyl, 2,3,4-tribromobutyl, 2,3-dibromopentyl, 3,4-dibromopentyl, 3,5-dibromopentyl, 3,4,5-tribromopentyl, 2,4,5-tribromopentyl, 2,3-dibromohexyl, 3,4-dibromohexyl, 3,5-dibromohexyl, 3,4,5-tribromohexyl, 2,4,5-tribromohexyl, fluoromethyl, 2-fluoroethyl, 3-fluoropropyl, 2-fluoropropyl, 2-fluoroisopropyl, 2-fluorobutyl, 3-fluorobutyl, 4-fluorobutyl, 5-fluoropentyl, 2-fluoropentyl, 3-fluoropentyl, 4-fluoropentyl, 6-fluorohexyl, 2-fluorohexyl, 3-fluorohexyl, 4-fluorohexyl, 1-methyl-2-fluoroethyl, 1,1-dimethyl-2-fluoroethyl, 1,2-difluoroethyl, 2,2-difluoroethyl, 1,3-difluoropropyl, 2,3-difluoropropyl, 1,2,3-trifluoropropyl, 1,4-difluorobutyl, 2,4-difluorobutyl, 3,4-difluorobutyl, 1,2-difluorobutyl, 2,3-difluorobutyl, 1,3-difluorobutyl, 2,2-difluorobutyl, 1,2,3-trifluorobutyl, 2,3,4-trifluorobutyl, 2,3-difluoropentyl, 3,4-difluoropentyl, 3,5-difluoropentyl, 3,4,5-trifluoropentyl, 2,4,5-trifluoropentyl, 2,3-difluorohexyl, 3,4-difluorohexyl, 3,5-difluorohexyl, 3,4,5-trifluorohexyl, 2,4,5-trifluorohexyl, iodomethyl, 2-iodoethyl, 3-iodopropyl, 2-iodopropyl, 2-iodoisopropyl, 2-iodobutyl, 3-iodobutyl, 4-iodobutyl, 5-iodopentyl, 2-iodopentyl, 3-iodopentyl, 4-iodopentyl, 6-iodohexyl, 2-iodohexyl, 3-iodohexyl, 4-iodohexyl, 6-iodohexyl, 2-iodohexyl, 3-iodohexyl, 4-iodohexyl, 1-methyl-2-iodoethyl, 1,1-dimethyl-2-iodoethyl, 1,2-diiodoethyl, 2,2-diiodoethyl, 1,3-diiodopropyl, 2,3-diiodopropyl, 1,2,3-triiodopropyl, 1,4-diiodobutyl, 2,4-diiodobutyl, 3,4-diiodobutyl, 1,2-diiodobutyl, 2,3-diiodobutyl, 1,3-diiodobutyl, 2,2-diiodobutyl, 1,2,3-triiodobutyl, 2,3,4-triiodobutyl, 2,3-diiodopentyl, 3,4-diiodopentyl, 3,5-diiodopentyl, 3,4,5-triiodopentyl, 2,4,5-triiodopentyl, 2,3-diiodohexyl, 3,4-diiodohexyl, 3,5-diiodohexyl, 3,4,5-triiodohexyl, 2,4,5-triiodohexyl, 1-chloro-2-bromoethyl, and 2-chloro-4-fluorobutyl groups can be exemplified.

As to the cycloalkenyl group, a cycloalkenyl group having 3 to 8 carbon atoms, such as cyclopropenyl, cyclobutynyl, cyclopentynyl, cyclohexenyl, cycloheptenyl and cyclooctenyl groups can be exemplified.

As to the lower alkynyl group, a straight chain- or branched chain-alkynyl group having 2 to 6 carbon atoms, such as ethynyl, 2-propynyl, 2-butynyl, 3-butynyl, 1-methyl-2-propynyl, 2-pentynyl and 2-hexynyl groups can be exemplified.

As to the lower alkoxy group, a straight chain- or branched chain-alkoxy group having 1 to 6 carbon atoms, such as methoxy, ethoxy, propoxy, isopropoxy, butoxy, tert-butoxy, pentyloxy and hexyloxy groups can be exemplified.

As to the phenyl-lower alkyl group which may have 1 to 3 substituents selected from the group consisting of a lower alkenyloxy group, a lower alkoxy group, a lower alkenyl group, a hydroxyl group, a lower alkyl group, a carboxyl group, a lower alkoxycarbonyl group and a group of the formula:

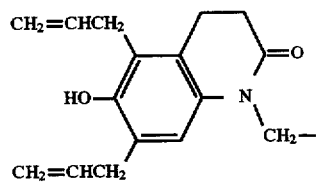

in the phenyl ring; a phenylalkyl group in which the alkyl moiety is a straight chain- or branched chain-alkyl group having 1 to 6 carbon atoms, said phenyl-alkyl group may have 1 to 3 substituents selected from the group consisting of a straight chain- or branched chain-alkenyloxy group having 2 to 6 carbon atoms, a straight chain- or branched chain-alkoxy group having 1 to 6 carbon atoms, a straight chain- or branched chain-alkenyl group having 1 to 6 carbon atoms, a hydroxyl group, a straight chian- or branched chain-alkyl group having 1 to 6 carbon atoms, a carboxyl group, a carbonyl group having a straight chain- or branched chain-alkoxy group having 1 to 6 carbon atoms and a group of the formula:

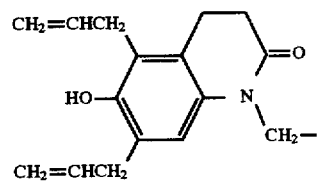

in the phenyl ring, such as benzyl, 2-phenylethyl, 1-phenylethyl, 3-phenylpropyl, 4-phenylbutyl, 1,1-dimethyl-2-phenylethyl, 2-methyl-3-phenylpropyl, 5-phenylpentyl, 6-phenylhexyl, 2-vinyloxybenzyl, 3-vinyloxybenzyl, 3-allyloxybenzyl, 4-allyloxybenzyl, 3,4-divinyloxybenzyl, 3,4,5-triallyloxybenzyl, 2-[2-(2-butenyloxy)phenyl]ethyl, 3-[3-(1-methylallyloxy)-phenyl]propyl, 4-[4-(2-pentenyloxy)phenyl]butyl, 5-[2-(2-hexenyloxy)phenyl]pentyl, 5-[3-(3-butenyloxy)-phenyl]ethyl, 2-[3,4-di-(2-butenyloxy)phenyl]ethyl, 2-(3,4-diallyloxyphenyl)ethyl, 1-(3,4-vinyloxypheyl)-ethyl, 2-(3,4,5-triallyloxyphenyl)ethyl, 3-(3,4-diallyloxyphenyl)propyl, 4-(3,4-diallyloxyphenyl)butyl, 6-(3,4-diallyloxyphenyl)hexyl, 1,1-dimethyl-2-(3,4-diallyloxyphenyl)ethyl, 2-(2,5-diallyloxyphenyl)ethyl, 2-methoxybenzyl, 3-methoxybenzyl, 4-methoxybenzyl, 3,4-dimethoxybenzyl, 3-ethoxy-4-methoxybenzyl, 3,4,5-trimethoxybenzyl, 2-(2-ethoxyphenyl)ethyl, 2-(3,4-dipropoxyphenyl)ethyl, 3-(3-propoxyphenyl)propyl, 4-(4-butoxyphenyl)butyl, 5-(2-pentyloxyphenyl)pentyl, 6-(3-hexyloxyphenyl)hexyl, 2-(4-isopropoxyphenyl)ethyl, 2-(3,4-diisopropoxyphenyl)ethyl, 2-(3,4-dibutoxyphenyl)ethyl, 1-(3,4-diethoxyphenyl)ethyl, 2-(3,4,5-trimethoxyphenyl)ethyl, 3-(3,4-dimethoxyphenyl)propyl, 4-(3,4-dimethoxyphenyl)butyl, 6-(3,4-dimethoxyphenyl)-hexyl, 1,1-dimethyl-2-(3,4-dimethoxyphenyl)ethyl, 2-(2,5-dimethoxyphenyl)ethyl, 2-vinylbenzyl, 3-vinylbenzyl, 4-allylbenzyl, 3,4-divinylbenzyl, 3,4,5-triallylbenzyl, 2-(2-vinylphenyl)ethyl, 2-[3-(1-methylallyl)phenyl]ethyl, 3-[4-(2-butenyl)phenyl]-propyl 4-[3-(3-butenyl)phenyl]butyl, 5-[2-(2-pentenyl)phenyl]pentyl, 2-[3,4-di-(2-butenyl)-phenyl]ethyl, 2-(3,4-diallylphenyl)ethyl, 6-[4-(2-hexenyl)phenyl]hexyl, 2-(3,4,5-triallylphenyl)ethyl, 3-(3,4-diallylphenyl)propyl, 4-(3,4-diallylphenyl)-butyl, 6-(3,4-diallylphenyl)hexyl, 1,1-dimethyl-2-(3,4-diallylphenyl)ethyl, 2-(2,5-diallylphenyl)ethyl, 2-hydroxybenzyl, 3-hydroxybenzyl, 4-hydroxybenzyl, 3,4-dihydroxybenzyl, 3,4,5-trihydroxybenzyl, 2-(2-hydroxyphenyl)ethyl, 2-(3-hydroxyphenyl)ethyl, 2-(4-hydroxyphenyl)ethyl, 2-(3,4-dihydroxyphenyl)ethyl, 2-(3,4-diethoxyphenyl)ethyl, 2-(3,4-diisopropoxyphenyl)ethyl, 2-(3,4-dibutoxyphenyl)ethyl, 1-(3,4-dihydroxyphenyl)ethyl, 2-(3,4,5-trihydroxyphenyl)ethyl, 3-(3,4-dihydroxyphenyl)propyl, 4-(3,4-dihydroxyphenyl)butyl, 6-(3,4-dihydroxyphenyl)hexyl, 1,1-dimethyl-2-(3,4-dihydroxyphenyl)ethyl, 2-(2,5-dihydroxyphenyl)ethyl, 2-methylbenzyl, 3-methylbenzyl, 4-ethylbenzyl, 4-methylbenzyl, 2-ethylbenzyl, 3-ethylbenzyl, 3,4-dimethylbenzyl, 3,4,5-trimethylbenzyl, 2-(2-methylphenyl)ethyl, 2-[3-(2-ethyl)phenyl]ethyl, 2-(3,4-dimethylphenyl)ethyl, 2-[3,4-di-(4-butyl)-phenyl]ethyl, 2-(3,5-dimethylphenyl)ethyl, 1-[3,4-di-(2-ethyl)phenyl]ethyl, 2-[3,4,5-tri-(2-ethyl)phenyl]-ethyl, 3-(3,4-dimethylphenyl)propyl, 4-(3,4-dimethylphenyl)butyl, 6-(3,4-dimethylphenyl)hexyl, 1,1-dimethyl-2-(3,4-dimethylphenyl)ethyl, 2-(2,5-dimethylphenyl)ethyl, 3-(2-pentylphenyl)propyl, 4-(3-butylphenyl)butyl, 5-(4-hexylphenyl)pentyl, 6-(2-methylphenyl)hexyl, 2-carboxybenzyl, 3-carboxybenzyl, 4-carboxybenzyl, 3,4-dicarboxybenzyl, 3,4,5-tricarboxybenzyl, 2-(2-carboxyphenyl)ethyl, 2-(3-carboxyphenyl)ethyl, 2-(4-carboxyphenyl)ethyl, 2-(3,4-dicarboxyphenyl)ethyl, 1-(3,4-dicarboxyphenyl)-ethyl, 2-(3,4,5-tricarboxyphenyl)ethyl, 3-(3,4-dicarboxyphenyl)propyl, 4-(3,4-dicarboxyphenyl)butyl, 6-(3,4-dicarboxyphenyl)hexyl, 1,1-dimethyl-2-(3,4-dicarboxyphenyl)ethyl, 2-(2,5-dicarboxyphenyl)ethyl, 2-methoxycarbonylbenzyl, 3-methoxycarbonylbenzyl, 4-methoxycarbonylbenzyl, 3,4-dimethoxycarbonylbenzyl, 3,4,5-trimethoxycarbonylbenzyl, 2-(2-ethoxycarbonylphenyl)ethyl, 3-(3-propoxycarbonylphenyl)propyl, 4-(4-butoxycarbonylphenyl)butyl, 5-(2-pentyloxycarbonylphenyl)pentyl, 6-(3-hexyloxycarbonylphenyl)-hexyl, 2-(3,4-diisopropoxycarbonylphenyl)ethyl, 2-(3,4-dibutoxycarbonylphenyl)ethyl, 1-(3,4-diethoxycarbonylphenyl)ethyl, 2-(3,4,5-trimethoxycarbonylphenyl)ethyl, 3-(3,4-dimethoxycarbonylphenyl)propyl, 4-(3,4-dimethoxycarbonylphenyl)butyl, 6-(3,4-dimethoxycarbonylphenyl)hexyl, 1,1-dimethyl-2-(3,4-dimethoxycarbonylphenyl)ethyl, 2-(2,5-dimethoxycarbonylphenyl)-ethyl, 2-(3,4-diethoxycarbonylphenyl)ethyl, 2-(3,4-diisopropoxycarbonylphenyl)ethyl, 2-(3,4-dibutoxycarbonylphenyl)ethyl, 2-(4-isopropoxycarbonylphenyl)-ethyl, 3-ethoxycarbonyl-4-methoxycarbonylbenzyl, 3-allyl-4-hydroxybenzyl, 4-hydroxy-3-allyl-2-methylphenyl, 3,5-diallyl-4-hydroxybenzyl and [(5,7-diallyl-4-hydroxy-3,4-dihydrocarbostyril-1-yl)methyl]benzyl groups can be exemplified.

As to the naphthyl-substituted lower alkyl group, a naphthyl-substituted alkyl group in which the alkyl moiety is a straight chain- or branched chain-alkyl group having 1 to 6 carbon atoms, such as naphthylmethyl, 2-naphthylethyl, 3-naphthylpropyl, 1-methyl-2-naphthylethyl, 4-naphthylbutyl, 1,1-dimethyl-2-naphthylethyl, 5-naphthylpentyl, 6-naphthylhexyl and 2-methyl-3-naphthylpropyl groups can be exemplified.

As to the phthalimido-substituted lower alkyl group, a phthalimido-substituted alkyl group in which the alkyl moiety is a straight chain- or branched chain-alkyl group having 1 to 6 carbon atoms, such as phthalimidomethyl, 2-phthalimidoethyl, 3-phthalimidopropyl, 1-methyl-2-phthalimidoethyl, 4-phthalimidobutyl, 1,1-dimethyl-2-phthalimidoethyl, 5-phthalimidopentyl, 6-phthalimidohexyl and 2-methyl-3-phthalimidopropyl groups can be exemplified.

As to the lower alkoxycarbonyl-substituted lower alkyl group, an alkoxycarbonylalkyl group in which the alkoxycarbonyl moiety is a straight chain- or branched chain-alkoxycarbonyl group having 1 to 6 carbon atoms, and the alkyl moiety is a straight chain- or branched chain-alkyl group having 1 to 6 carbon atoms, such as methoxycarbonylmethyl, 2-methoxycarbonylethyl, 3-methoxycarbonylpropyl, 4-methoxycarbonylbutyl, 5-methoxycarbonylpentyl, 6-methoxycarbonylhexyl, 1-methyl-2-methoxycarbonylethyl, 2-methoxycarbonylpropyl, 1,1-dimethyl-2-methoxycarbonylethyl, ethoxycarbonylmethyl, 2-ethoxycarbonylethyl, 3-ethoxycarbonylpropyl, 4-ethoxycarbonylbutyl, 5-ethoxycarbonylpentyl, 6-ethoxycarbonylhexyl, 1-methyl-2-ethoxycarbonylethyl, 2-ethoxycarbonylpropyl, 1,1-dimethyl-2-ethoxycarbonylethyl, propoxycarbonylmethyl, 2-propoxycarbonylethyl, 3-propoxycarbonylpropyl, 4-propoxycarbonylbutyl, 5-propoxycarbonylhexyl, 2-propoxycarbonylpropyl, 2-isopropoxycarbonylethyl, 2-butoxycarbonylethyl, 3-butoxycarbonylpropyl, 4-butoxycarbonylbutyl, 6-butoxycarbonylpropyl, 2-tertbutoxycarbonylethyl, 2-pentyloxycarbonylethyl, 5-pentyloxycarbonylpentyl, 2-hexyloxycarbonylethyl and 6-hexyloxycarbonylhexyl can be exemplified.

As to the lower alkylene group, a straight chain- or branched chain-alkylene group having 1 to 6 carbon atoms, such as methylene, ethylene, trimethylene, 2-methyltrimethylene, 2,2-dimethyltrimethylene, 1-methyltrimethylene, methylmethylene, ethylmethylene, tetramethylene, pentamethylene and hexamethylene group can be exemplified.

As to the phenylsulfonyl group which may have lower alkyl group(s) as the substituent(s) in the phenyl ring, a phenylsulfonyl group which may have 1 to 3 straight chain- or branched chain-alkyl groups having 1 to 6 carbon atoms as the substituents in the phenyl ring, such as phenylsulfonyl, 2-methylphenylsulfonyl, 3-methylphenylsulfonyl, 4-methylphenylsulfonyl, 2-ethylphenylsulfonyl, 3-ethylphenylsulfonyl, 4-ethylphenylsulfonyl, 3-isopropylphenylsulfonyl, 4-butyl-phenylsulfonyl, 4-pentylphenylsulfonyl, 4-hexylphenylsulfonyl, 3,4-dimethylphenylsulfonyl, 2,5-dimethylphenylsulfonyl and 3,4,5-trimethylphenylsulfonyl groups can be exemplified.

As to the lower alkoxy-lower alkyl group, a straight chain- or branched chain-alkyl group having 1 to 6 carbon atoms to which a straight chain- or branched chain-alkoxy group having 1 to 6 carbon atoms is substituted, such as methoxymethyl, 2-methoxyethyl, 3-methoxypropyl, 4-methoxybutyl, 5-methoxypentyl, 6-methoxyhexyl, 1-methyl-2-methoxyethyl, 2-methoxypropyl, 1,1-dimethyl-2-methoxyethyl, ethoxymethyl, 2-ethoxyethyl, 3-ethoxypropyl, 4-ethoxybutyl, 5-ethoxypentyl, 6-ethoxyhexyl, 1-methyl-2-ethoxyethyl, 2-ethoxypropyl, 1,1-dimethyl-2-ethoxyethyl, propoxymethyl, 2-propoxyethyl, 3-propoxypropyl, 4-propoxybutyl, 5-propoxyhexyl, 2-propoxypropyl, 2-isopropoxyethyl, 2-butoxyethyl, 3-butoxypropyl, 4-butoxybutyl, 6-butoxyhexyl, 2-tert-butoxyethyl, 2-pentyloxyethyl, 5-pentyloxypentyl, 2-hexyloxyethyl and 6-hexyloxyhexyl groups can be exemplified.

As to the phenyl group which may have halogen atom(s) as the substituent(s) in the phenyl ring, a phenyl group which may have 1 to 3 halogen atoms as the substituents in the phenyl ring, such as phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl and 3,4,5-trichlorophenyl groups can be exemplified.

As to the 5- or 6-membered saturated or unsaturated heterocyclic group by combining $R^4$ and $R^5$ together with the adjacent nitrogen atom being bonded thereto together with or without other nitrogen atom or oxygen atom, pyrrolidinyl, piperidinyl, piperazinyl, morpholino, pyrrolyl, imidazolyl, 1,2,4-triazolyl, 1,3,4-triazolyl, pyrazolyl, 2-pyrrolinyl, 2-imidazolinyl, imidazolidinyl, 2-pyrazolinyl, pyrazolidinyl, 1,2-dihydropyridyl, 1,2,3,4-tetrahydropyridyl and 1,2,3,4-tetrazolyl groups can be exemplified.

As to the heterocyclic group having substituent(s) selected from the group consisting of carbamoyl group, carboxyl group, cycloalkyl group and a phenyl group which may have halogen atom(s) in the phenyl ring, a heterocyclic group having 1 to 3 substituents selected from the group consisting of a carbamoyl group, a carboxyl group, a cycloalkyl group and a phenyl group which may have 1 to 3 halogen atoms in the phenyl ring, such as 2-carbamoylpyrrolidinyl, 3-carbamoylpyrrolidinyl, 4-carbamoylpiperidinyl, 3-carbamoylpiperidinyl, 2-carbamoylpiperidinyl, 4-carbamoylpiperazinyl, 3-carbamoylpiperazinyl, 2-carbamoylpiperazinyl, 3-carbamoylmorpholino, 2-carbamoylmorpholino, 2-carbamoylpyrrolyl, 3-carbamoylpyrrolyl, 2-carbamoylimidazolyl, 4-carbamoylimidazolyl, 5-carbamoylimidazolyl, 3-carbamoyl-1,2,4-triazolyl, 5-carbamoyl-1,2,4-triazolyl, 2-carbamoyl-1,2,4-triazolyl, 5-carbamoylpyrazolyl, 3-carbamoylpyrazolyl, 2-carbamoyl-2-pyrrolinyl, 3-carbamoyl-2-pyrrolinyl, 4-carbamoyl-2-pyrrolinyl, 5-carbamoyl-2-pyrrolinyl, 2-carbamoyl-2-imidazolinyl, 5-carbamoyl-1,2,3,4-tetrazolyl, 4-carbamoyl-2-imidazolinyl, 5-carbamoyl-2-imidazolinyl, 2-carbamoylimidazolidinyl, 4-carbamoylimidazolidinyl, 5-carbamoylimidazolidinyl, 3-carbamoyl-2-pyrazolinyl, 4-carbamoyl-2-pyrazolinyl, 5-carbamoyl-2-pyrazolinyl, 3-carbamoylpyrazolidinyl, 4-carbamoylpyrazolidinyl, 5-carbamoylpyrazolidinyl, 2-carbamoyl-1,2-dihydropyridyl, 3-carbamoyl-1,2-dihydropyridyl, 4-carbamoyl-1,2-dihydropyridyl, 2,6-dicarbamoyl-1,2-dihydropyridyl, 3,4-dicarbamoylpiperidinyl, 2,4,6-tricarbamoyl-1,2-dihydropyridyl, 4-carbamoyl-1,2,3,4-tetrahydropyridyl, 3,4,5-tricarbamoyl-1,2,3,4-tetrahydropyridyl, 3,4-dicarbamoyl-1,2,3,4-tetrahydropyridyl, 3,4-dicarbamoylpiperazinyl, 2-carboxypyrrolidinyl, 3-carboxypyrrolidinyl, 4-carboxypiperidinyl, 3-carboxypiperidinyl, 2-carboxypiperidinyl, 4-carboxypiperazinyl, 3-carboxypiperazinyl, 2-carbboxypiperazinyl, 3-carboxymorpholino, 2-carboxymorpholino, 2-carboxypyrrolyl, 3-carboxypyrrolyl, 2-carboxyimidazolyl, 4-carboxyimidazolyl, 5-carboxyimidazolyl, 3-carboxy-1,2,4-triazolyl, 5-carboxy-1,2,4-triazolyl, 2-carboxy-1,2,4-triazolyl, 5-carboxypyrazolyl, 3-carboxypyrazolyl, 2-carboxy-2-pyrrolinyl, 3-carboxy-2-pyrrolinyl, 4-carboxy-2-pyrrolinyl, 5-carboxy-2-pyrrolinyl, 2-carboxy-2-imidazolyl, 5-carboxy-1,2,3,4-tetrazolyl, 4-carboxy-2-imidazolinyl, 5-carboxy-2-imidazolyl, 2-carboxyimidazolidinyl, 4-carboxyimidazolidinyl, 5-carboxyimidazolidinyl, 5-carboxy-2-pyrazolinyl, 3-carboxypyrrazolidinyl, 4-carboxypyrrazolidinyl, 5-carboxypyrrazolidinyl, 2-carboxy-1,2-dihydropyridyl, 3-carboxy-1,2-dihydropyridyl, 4-carboxy-1,2-dihydropyridyl, 2,6-dicarboxy-1,2-dihydropyridyl, 3,4-dicarboxypiperidinyl, 2,4,6-tricarboxy-1,2-dihydropyridyl, 4-carboxy-1,2,3,4-tetrahydropyridyl, 3,4,5-tricarboxy-1,2,3,4-tetrahydropyridyl, 3,4-dicarboxy-1,2,3,4-tetrahydropyridyl, 3,4-dicarboxypiperazinyl, 2-cyclopropylpyrrolidinyl, 3-cyclopropylpyrrolidinyl, 4-cyclopropylpiperidinyl, 3-cyclopropylpiperidinyl, 2-cyclopropylpiperidinyl, 4-cyclopropylpiperazinyl, 3-cyclopropylpiperazinyl, 2-cyclopropylpiperazinyl, 3-cyclopropylmorpholino, 2-cyclopropylmorpholino, 2-cyclopropylpyrrolyl, 3-cyclopropylpyrrolyl, 2-cyclopropylimidazolyl, 4-cyclopropylimidazolyl, 5-cyclopropylimidazolyl, 3-cyclopropyl-1,2,4-triazolyl, 5-cyclopropyl-1,2,4-triazolyl, 2-cyclopropyl-1,2,4-triazolyl, 5-cyclopropylpyrazolyl, 3-cyclopropylpyrazolyl, 2-cyclopropyl-2-pyrrolinyl, 3-cyclopropyl-2-pyrrolinyl, 4-cyclopropyl-2-pyrrolinyl, 5-cyclopropyl-2-pyrrolinyl, 2-cyclopropyl-2-imidazolyl, 5-cyclopropyl-1,2,3,4-tetrazolyl, 4-cyclopropyl-2-imidazolinyl, 5-cyclopropyl-2-imidazolyl, 2-cyclopropylimidazolidinyl, 4-cyclopropylimidazolidinyl, 5-cyclopropylimidazolidinyl, 5-cyclopropyl-2-pyrazolinyl, 3-cyclopropylpyrazolidinyl, 4-cyclopropylpyrazolidinyl, 5-cyclopropylpyrazolidinyl, 2-cyclopropyl-1,2-dihydropyridyl, 3-cyclopropyl-1,2-dihydropyridyl, 4-cyclopropyl-1,2-dihydropyridyl, 2,6-dicyclopropyl-1,2-dihydropyridyl, 3,4-dicyclopropylpiperidinyl, 2,4,6-tricyclopropyl-1,2-dihydropyridyl, 4-cyclopropyl-1,2,3,4-tetrahydropyridyl, 3,4,5-tricyclopropyl-1,2,3,4-tetrahydropyridyl, 3,4-dicyclopropyl-1,2,3,4- tetrahydropyridyl, 3,4-dicyclopropylpiperazinyl, 2-cyclobutylpyrrolidinyl, 3-cyclobutylpyrrolidinyl, 4-cyclobutylpiperidinyl, 3-cyclobutylpiperidinyl, 2-cyclobutylpiperidinyl, 4-cyclobutylpiperazinyl, 3-cyclobutylpiperazinyl, 2-cyclobutylpiperazinyl, 3-cyclobutylmorpholino, 2-cyclobutylmorpholino, 2-cyclobutylpyrrolyl, 3-cyclobutylpyrrolyl, 2-cyclobutylimidazolyl, 4-cyclobutylimidazolyl, 5-cyclobutylimidazolyl, 3-cyclobutyl-1,2,4-triazolyl, 5-cyclobutyl-1,2,4-triazolyl, 2-cyclobutyl-1,2,4-triazolyl, 5-cyclobutylpyrazolyl, 3-cyclobutylpyrazolyl, 2-cyclobutyl-2-pyrrolinyl, 3-cyclobutyl-2-pyrrolinyl, 4-cyclobutyl-2-pyrrolinyl, 5-cyclobutyl-2-pyrrolinyl, 2-cyclobutyl-2-imidazolyl, 5-cyclobutyl-1,2,3,4-tetrazolyl, 4-cyclobutyl-2-imidazolinyl, 5-cyclobutyl-2-imidazolyl, 2-cyclobutylimidazolidinyl, 4-cyclobutylimidazolidinyl, 5-cyclobutylimidazolidinyl, 5-cyclobutyl-2-pyrazolinyl, 3-cyclobutylpyrazolidinyl, 4-cyclobutylpyrazolidinyl, 5-cyclobutylpyrazolidinyl, 2-cyclobutyl-1,2-dihydropyridyl, 3-cyclobutyl-1,2-dihydropyridyl, 4-cyclobutyl-1,2-dihydropyridyl, 2,6-dicyclobutyl-1,2-dihydropyridyl, 3,4-dicyclobutylpiperidinyl, 2,4,6-tricyclobutyl-1,2-dihydropyridyl, 4-cyclobutyl-1,2,3,4-tetrahydropyridyl, 3,4,5-tricyclobutyl-1,2,3,4-tetrahydropyridyl, 3,4-dicyclobutyl-1,2,3,4-tetrahydropyridyl, 3,4-dicyclobutylpiperazinyl, 2-cyclopentylpyrrolidinyl, 3-cyclopentylpyrrolidinyl, 4-cyclopentylpiperidinyl, 3-cyclopentylpiperidinyl, 2-cyclopentylpiperidinyl, 4-cyclopentylpiperazinyl, 3-cyclopentylpiperazinyl, 2-cyclopentylpiperazinyl, 3-cyclopentylmorpholino, 2-cyclopentylmorpholino, 2-cyclopentylpyrrolyl, 3-cyclopentylpyrrolyl, 2-cyclopentylimidazolyl, 4-cyclopentylimidazolyl, 5-cyclopentylimidazolyl, 3-cyclopentyl-1,2,4-triazolyl, 5-cyclopentyl-1,2,4-triazolyl, 2-cyclopentyl-1,2,4-triazolyl, 5-cyclopentylpyrazolyl, 3-cyclopentylpyrazolyl, 2-cyclopentyl-2-pyrrolinyl, 3-cyclopentyl-2-pyrrolinyl, 4-cyclopentyl-2-pyrrolinyl, 5-cyclopentyl-2-pyrrolinyl, 2-cyclopentyl-2-imidazolyl, 5-cyclopentyl-1,2,3,4-tetrazolyl, 4-cyclopentyl-2-imidazolinyl, 5-cyclopentyl-2-imidazolyl, 2-cyclopentylimidazolidinyl, 4-cyclopentylimidazolidinyl, 5-cyclopentylimidazolidinyl, 5-cyclopentyl-2-pyrazolinyl, 3-cyclopentylpyrazolidinyl, 4-cyclopentylpyrazolidinyl, 5-cyclopentylpyrazolidinyl, 2-cyclopentyl-1,2-dihydropyridyl, 3-cyclopentyl-1,2-dihyropyridyl, 4-cyclopentyl-1,2-dihyropyridyl, 2,6-dicyclopentyl-1,2-dihydropyridyl, 3,4-dicyclopentylpiperidinyl, 2,4,6-tricyclopentyl-1,2-dihydropyridyl, 4-cyclopentyl-1,2,3,4-tetrahydropyridyl, 3,4,5-tricyclopentyl-1,2,3,4-tetrahydropyridyl, 3,4-dicyclopentyl-1,2,3,4-tetrahydropyridyl, 3,4-dicyclopentylpiperazinyl, 2-cyclohexylpyrrolidinyl, 3-cyclohexylpyrrolidinyl, 4-cyclohexylpiperidinyl, 3-cyclohexylpiperidinyl, 2-cyclohexylpiperidinyl, 4-cyclohexylpiperazinyl, 3-cyclohexylpiperazinyl, 2-cyclohexylpiperazinyl, 3-cyclohexylmorpholino, 2-cyclohexylmorpholino, 2-cyclohexylpyrrolyl, 3-cyclohexylpyrrolyl, 2-cyclohexylimidazolyl, 4-cyclohexylimidazolyl, 5-cyclohexylimidazolyl, 3-cyclohexyl-1,2,4-triazolyl, 5-cyclohexyl-1,2,4-triazolyl, 2-cyclohexyl-1,2,4-triazolyl, 5-cyclohexylpyrazolyl, 3-cyclohexylpyrazolyl, 2-cyclohexyl-2-pyrrolinyl, 3-cyclohexyl-2-pyrrolinyl, 4-cyclohexyl-2-pyrrolinyl, 5-cyclohexyl-2-pyrrolinyl, 2-cyclohexyl-2-imidazolyl, 5-cyclohexyl-1,2,3,4-tetrazolyl, 4-cyclohexyl-2-imidazolinyl, 5-cyclohexyl-2-imidazolyl, 2-cyclohexylimidazolidinyl, 4-cyclohexylimidazolidinyl, 5-cyclohexylimidazolidinyl, 5-cyclohexyl-2-pyrazolinyl, 3-cyclohexylpyrazolidinyl, 4-cyclohexylpyrazolidinyl, 5-cyclohexylpyrazolidinyl, 2-cyclohexyl-1,2-dihydropyridyl, 3-cyclohexyl-1,2-dihydropyridyl, 4-cyclohexyl-1,2-dihydropyridyl, 2,6-dicyclohexyl-1,2-dihydropyridyl, 3,4-dicyclohexylpiperidinyl, 2,4,6-tricyclohexyl-1,2-dihydropyridyl, 4-cyclohexyl-1,2,3,4-tetrahydropyridyl, 3,4,5-tricyclohexyl-1,2,3,4-tetrahydropyridyl, 3,4-dicyclohexyl-1,2,3,4-tetrahydropyridyl, 3,4-dicyclohexylpiperazinyl, 2-cycloheptylpyrrolidinyl, 3-cycloheptylpyrrolidinyl, 4-cycloheptylpiperidinyl, 3-cycloheptylpiperidinyl, 2-cycloheptylpiperidinyl, 4-cycloheptylpiperazinyl, 3-cycloheptylpiperazinyl, 2-cycloheptylpiperazinyl, 3-cycloheptylmorpholino, 2-cycloheptylmorpholino, 2-cycloheptylpyrrolyl, 3-cycloheptylpyrrolyl, 2-cycloheptylimidazolyl, 4-cycloheptylimidazolyl, 5-cycloheptylimidazolyl, 3-cycloheptyl-1,2,4-triazolyl, 5-cycloheptyl-1,2,4-triazolyl, 2-cycloheptyl-1,2,4-triazolyl, 5-cycloheptylpyrazolyl, 3-cycloheptylpyrazolyl, 2-cycloheptyl-2-pyrrolinyl, 3-cycloheptyl-2-pyrrolinyl, 4-cycloheptyl-2-pyrrolinyl, 5-cycloheptyl-2-pyrrolinyl, 2-cycloheptyl-2-imidazolyl, 5-cycloheptyl-1,2,3,4-tetrazolyl, 4-cycloheptyl-2-imidazolinyl, 5-cycloheptyl-2-imidazolyl, 2-cycloheptylimidazolidinyl, 4-cycloheptylimidazolidinyl, 5-cycloheptylimidazolidinyl, 5-cycloheptyl-2-pyrazolinyl, 3-cycloheptylpyrazolidinyl, 4-cycloheptylpyrazolidinyl, 5-cycloheptylpyrazolidinyl, 2-cycloheptyl-1,2-dihydropyridyl, 3-cycloheptyl-1,2-dihydropyridyl, 4-cycloheptyl-1,2-dihydropyridyl, 2,6-dicycloheptyl-1,2-dihydropyridyl, 3,4-dicycloheptylpiperidinyl, 2,4,6-tricycloheptyl-1,2-dihydropyridyl, 4-cycloheptyl-1,2,3,4-tetrahydropyridyl, 3,4,5-tricycloheptyl-1,2,3,4-tetrahydropyridyl, 3,4-dicycloheptyl-1,2,3,4-tetrahydropyridyl, 3,4-dicycloheptylpiperazinyl, 2-cyclooctylpyrrolidinyl, 3-cyclooctylpyrrolidinyl, 4-cyclooctylpiperidinyl, 3-cyclooctylpiperidinyl, 2-cyclooctylpiperidinyl, 4-cyclooctylpiperazinyl, 3-cyclooctylpiperazinyl, 2-cyclooctylpiperazinyl, 3-cyclooctylmonopholino, 2-cyclooctylmonopholino, 2-cyclooctylpyrrolyl, 3-cyclooctylpyrrolyl, 2-cyclooctylimidazolyl, 4-cyclooctylimidazolyl, 5-cyclooctylimidazolyl, 3-cyclooctyl-1,2,4-triazolyl, 5-cyclooctyl-1,2,4-triazolyl, 2-cyclooctyl-1,2,4-triazolyl, 5-cyclooctylpyrazolyl, 3-cyclooctylpyrazolyl, 2-cyclooctyl-2-pyrrolinyl, 3-cyclooctyl-2-pyrrolinyl, 4-cyclooctyl-2-pyrrolinyl, 5-cyclooctyl-2-pyrrolinyl, 2-cyclooctyl-2-imidazolyl, 5-cyclooctyl-1,2,3,4-tetrazolyl, 4-cyclooctyl-2-imidazolinyl, 5-cyclooctyl-2-imidazolyl, 2-cyclooctylimidazolidinyl, 4-cyclooctylimidazolidinyl, 5-cyclooctylimidazolidinyl, 5-cyclooctyl-2-pyrazolinyl, 3-cyclooctylpyrazolidinyl, 4-cyclooctylpyrazolidinyl, 5-cyclooctylpyrazolidinyl, 2-cyclooctyl-1,2-dihydropyridyl, 3-cyclooctyl-1,2-dihydropyridyl, 4-cyclooctyl-1,2-dihydropyridyl, 2,6-dicyclooctyl-1,2-dihydropyridyl, 3,4-dicyclooctylpiperidinyl, 2,4,6-tricyclooctyl-1,2-dihydropyridyl, 4-cyclooctyl-1,2,3,4-tetrahydropyridyl, 3,4,5-tricyclooctyl-1,2,3,4-tetrahydropyridyl, 3,4-dicyclooctyl-1,2,3,4-tetrahydropyridyl, 3,4-dicyclooctylpiperazinyl, 4-phenylpiperazinyl, 5-(3-chlorophenyl)-1,2,3,4-tetrazolyl, 4-(3-chlorophenyl)piperazinyl, 4-(4-bromophenyl)piperidinyl, 3-(2-iodophenyl)pyrrolidinyl, 3-(4-fluorophenyl)morpholino, 3-(2-chlorophenyl)-pyrrolyl, 3-(3-bromophenyl)imidazolyl, 3-(4-iodophenyl)-1,2,4-triazolyl, 2-(2-fluorophenyl)-1,3,4-triazolyl, 3-(2,3-dichlorophenyl)pyrazolyl, 4-(3,4-dibromophenyl)-2- pyrrolinyl, 2-(2,5-diiodophenyl)-2-imidazolinyl, 3-(3,4-difluorophenyl)imidazolidinyl, 3-(2,4,6-trichlorophenyl)-2-pyrazolinyl, 4-(4-chlorophenyl)pyrazolidinyl, 4-(2-bromophenyl)-1,2-dihydropyridyl and 4-(2-chloro-4-bromophenyl)-1,2,3,4-tetrahydropyridyl groups can be exemplified.

As to the lower alkanoyloxy-substituted lower alkyl group, a straight chain- or branched chain-alkyl group having 1 to 6 carbon atoms being substituted with a straight chain- or branched chain-alkanoyloxy group having 2 to 6 carbon atoms, such as acetyloxymethyl, 2-propionyloxyethyl, 1-butyryloxyethyl, 3-acetyloxypropyl, 4-acetyloxybutyl, 4-isobutyryloxybutyl, 5-pentanoyloxypentyl, 6-acetyloxyhexyl, 6-tert-butylcarbonyloxyhexyl, 1,1-dimethyl-2-hexanoyloxyethyl and 2-methyl-3-acetyloxypropyl groups can be exemplified.

As to the cyano group-substituted lower alkyl group, a cyanoalkyl group in which the alkyl moiety is a straight chain- or branched chain-alkyl group having 1 to 6 carbon atoms, such as cyanomethyl, 2-cyanoethyl, 3-cyanopropyl, 1-methyl-2-cyanoethyl, 1-cyanoethyl, 4-cyanobutyl, 1,1-dimethyl-2-cyanoethyl, 5-cyanopentyl, 6-cyanohexyl, 2-methyl-3-cyanopropyl and 4-methyl-1-cyanopentyl groups can be exemplified.

As to the carboxy-substituted lower alkyl group, a carboxyalkyl group in which the alkyl moiety is a straight chain- or branched chain-alkyl group having 1 to 6 carbon atoms, such as carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxypropyl and 4-methyl-1-carboxypentyl groups can be exemplified.

As to the lower alkanoyl group which may have halogen atom(s), a straight chain- or branched chain-alkanoyl group having 1 to 6 carbon atoms which may have 1 to 3 halogen atoms as the substituents, such as formyl, acetyl, propionyl, butyryl, isobutyryl, pentanoyl, tert-butylcarbonyl, hexanoyl, 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 4,4,4-trichlorobutyryl, 4-fluorobutyryl, 5-chloropentanoyl, 3-chloro-2-methylpropionyl, 6-bromohexanoyl and 5,6-dibromohexanoyl groups can be exemplified.

As to the carbamoyl-substituted lower alkyl group, a carbamoylalkyl group in which the alkyl moiety is a straight chain- or branched chain-alkyl group having 1 to 6 carbon atoms, such as carbamoylmethyl, 2-carbamoylethyl, 1-carbamoylethyl, 3-carbamoylpropyl, 4-carbamoylbutyl, 5-carbamoylpentyl, 6-carbamoylhexyl, 1,1-dimethyl-2-carbamoylethyl and 2-methyl-3-carbamoylpropyl groups can be exemplified.

Among the cyclic amide derivatives of the present invention, when m is 1, then $R^3$ may preferably be bonded at any one of 5 to 8 position; and when m is 0, then $R^3$ may preferably be bonded at any one of 4 to 7 position. Further, as to preferable compounds of the present invention, those having that $R^2$ is a hydroxyl group; Z is a methylene group; m is 1; $R^1$ is an alkenyl group, a cycloalkyl-lower alkyl group or a phenyl-lower alkyl group having one substituent selected from the group consisting of a lower alkenyloxy group and an alkoxy group; n is 2; $R^2$ is bonded at 6-position and $R^3$ are bonded at 5- and 7-positions can be exemplified.

DETAILED DESCRIPTION OF THE PREFERRED EMBODIMENTS

The cyclic amide derivatives of the present invention can be prepared easily by methods as shown in various reaction formulae as follows.

Reaction formula-1

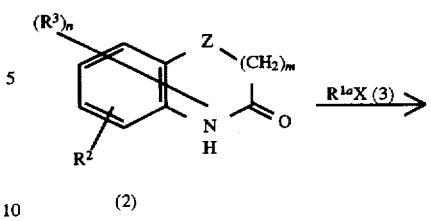

(2)

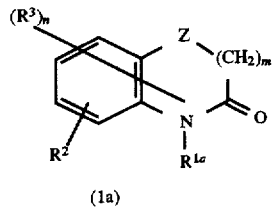

(1a)

In the Reaction formula-1, $R^2$, $R^3$, n, m and Z are the same as defined above; $R^{1a}$ is the same as defined above, except a hydrogen atom; X is a halogen atom, a lower alkylsulfonyloxy group or an arylsulfonyloxy group.

As to the lower alkylsulfonyloxy group, concretely, methylsulfonyloxy, ethylsulfonyloxy, isopropylsulfonyloxy, propylsulfonyloxy, butylsulfonyloxy, tert-butylsulfonyloxy, pentylsulfonyloxy and hexylsulfonyloxy groups can be exemplified. As to the arylsulfonyloxy group, concretely, phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy and α-naphthylsulfonyloxy groups can be exemplified.

In the above-mentioned Reaction formula-1, the reaction of a compound represented by the general formula (2) with a compound represented by the general formula (3) can be easily carried out without solvent or in a suitable inert solvent. Ratio of the used amount of a compound of the general formula (2) to the used amount of a compound of the general formula (3) is not specifically restricted and can be selected from a wide range. Generally, an equimolar to an excess quantity, preferably an equimolar to 5 times the molar quantity of the latter may be used to the molar quantity of the former. As to the inert solvent to be used in the reaction, aromatic hydrocarbons such as benzene, toluene and xylene; ethers such as dimethyl ether, diethyl ether, diisopropyl ether, tetrahydrofuran, dioxane and ethylene glycol; polar solvents such as dimethyl sulfoxide, dimethylformamide, hexamethylphosphoryl triamide and acetonitrile; as well as mixed solvent thereof can be exemplified.

The above reaction can advantageously be carried out by using a basic material as the dehydrohalogenation agent. As to the dehydrohalogenation agent to be used, alkali metals, such as metallic sodium and metallic potassium; alkali metal amides, such as sodium amide and potassium amide; sodium hydride and sodium hydroxide can be exemplified. The above reaction can also be carried out by adding, as the reaction accelerator, metal iodide compound for example, potassium iodide or sodium iodide; copper powder or copper halide to the reaction system. The reaction can be carried out generally at about 0 to 200° C., preferably at room temperature to 100° C. and is completed in about 1 to 24 hours.

Among the compounds represented by the general formula (1a), wherein $R^{1a}$ is a hydroxy-substituted alkyl group can be prepared by reating a compound represented by general formula (2) with a tetrahydropyranyloxy-substituted alkyl halide compound under the reaction condition similar to that employed in the reaction between a compound (2)

and a compound (3), then thus obtained compound (1a) wherein $R^{1a}$ is tetrahydropyranyloxy-substituted alkyl group is hydrolyzed under the condition similar to that employed in the hydrolysis in Reaction formula-7 as shown later.

In addition to the above, the compound (1a) wherein $R^{1a}$ is a phenyl-lower alkyl group having a group represented by the formula:

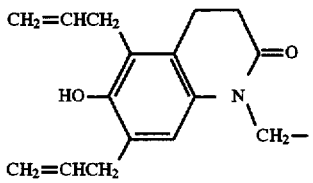

can be prepared by reacting a compound (2) with a phenyl-lower alkyl halide compound having halogenated methyl group as the substituent, under the reaction condition similar to that employed in the above-mentioned reaction of a compound (2) with a compound (3). In this case, 0.1 to 1.5 times the molar quantity of a phenyl-lower alkyl halide compound, having halogenated methyl group as the substituent, may preferably be used to a molar quantity of a compound (2).

Reaction formula-2

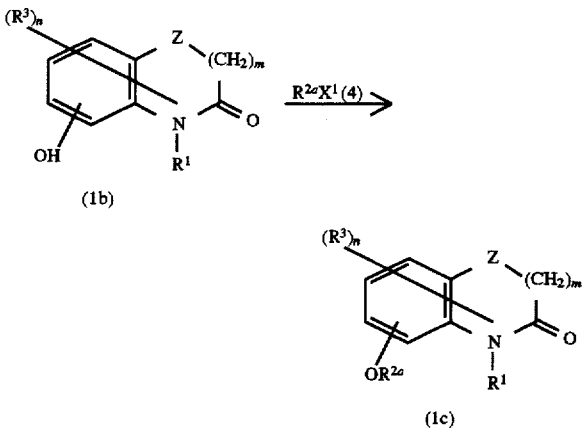

In the Reaction formula-2, $R^1$, $R^3$, n, m and Z are the same as defined above; $R^{2a}$ is a lower alkenyl group, a phenyl-lower alkenyl group, a cycloalkenyl group, a pyridyl group, a lower alkanoyl group which may have carboxy group(s); $X^1$ is a halogen atom.

In the above-mentioned Reaction formula-2, the reaction of a compound represented by the general formula (1b) with a compound represented by the general formula (4) can be carried out without solvent or in an inert solvent, in the absence of or in the presence of a basic compound. Ratio of the used amount of the compound of the general formula (1b) to the used amount of the compound of the general formula (4) is not specifically restricted, and generally an equimolar to an excess quantity, preferably an equimolar to 5 times the molar quantity of the latter may be used to the former. As to the inert solvent to be used, water; aromatic hydrocarbons such as benzene, toluene and xylene; ethers such as dimethyl ether, diethyl ether, diisopropyl ether, tetrahydrofuran, dioxane and diethylene glycol; halogenated hydrocarbons such as dichloromethane, chloroform, carbon tetrachloride; lower alcohol such as methanol, ethanol, isopropanol, butanol, tert-butanol; ketones such as methyl ethyl ketone; acetic acid; ethyl acetate; acetone; acetonitrile; pyridine; dimethyl sulfoxide; dimethylformamide and hexamethylphosphoryl triamide; and mixed solvents thereof can be exemplified. As to the basic materials, carbonate such as sodium carbonate, potassium carbonate, sodium hydrogen carbonate, potassium hydrogen carbonate; metal hydroxides such as sodium hydroxide, potassium hydroxide; sodium hydride; metallic potassium and metallic sodium; sodium amide; metal alcoholates such as sodium methylate and sodium ethylate; organic bases such as pyridine, N-ethyldiisopropylamine, dimethylaminopyridine, triethylamine, tripropylamine, 1,5-diazabicyclo[4.3.0]-5-nonene (DBN), 1,8-diazabicyclo[5.4.0]-7-undecene (DBU) and 1,4-diazabicyclo [2.2.2]octane (DABCO) can be exemplified. This reaction can be carried out, generally at about room temperature to 200° C., preferably at about room temperature to 100° C., and is generally completed in 1 to 24 hours. Into the reaction system, an alkali metal halide, such as sodium iodide or potassium iodide may be added.

Reaction formula-3

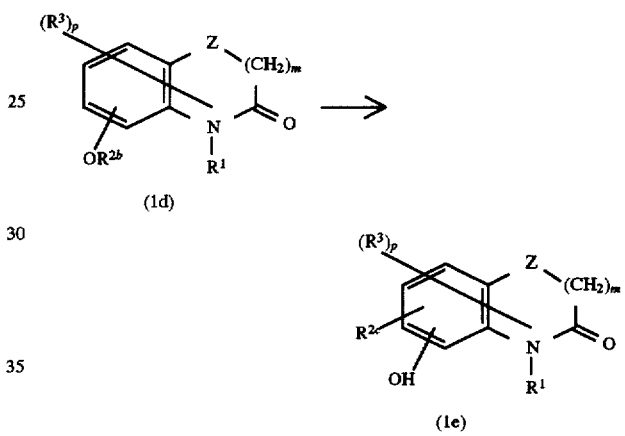

In the Reaction formula-3, $R^1$, $R^3$, m and Z are the same as defined above; $R^{2b}$ and $R^{2c}$ are each a lower alkenyl group, respectively; p is 0, 1 or 2.

The reaction introducing a compound represented by the general formula (1d) to a compound represented by the general formula (1e) is called as Claisen rearrangement, which is carried out without solvent or in an inert solvent, and generally under temperature condition at 100° to 250° C., preferably at 150° to 250° C., and is completed in 1 to 24 hours. As to the inert solvent to be used, solvents having higher-boiling point, such as diglyme, ethylene glycol, N,N-dimethylaniline, N,N,-diethylaniline, tetralin, decalin, dimethylformamide, tetrahydronaphthalene and diphenyl ether can be exemplified. The above-mentioned reaction can advantageously be carried out in an inert gas atmosphere. As to the inert gas, nitrogen gas and argon gas can be used.

Reaction formula-4

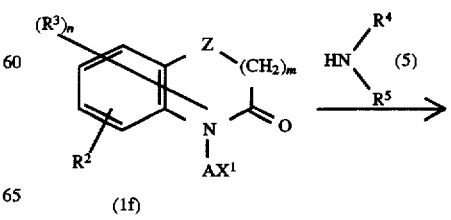

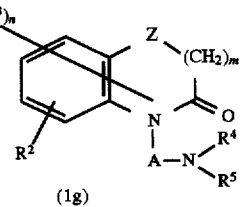

(1g)

In the Reaction formula-4, $R^2$, $R^3$, n, m, Z, A, $X^1$, $R^4$ and $R^5$ are the same as defined above.

The reaction of a compound represented by the general formula (1f) with a compound represented by the general formula (5) can be easily carried out without a solvent or in an inert solvent. Ratio of the used amounts of a compound of the general formula (1f) to a compound of the general formula (5) is not specifically restricted, and can be selected from a wide range. Generally, an equimolar to an excess quantity, preferably ably an equimolar to 5 times the molar quantity of the latter may be used to a molar quantity of the former. As to the inert solvent to be used, aromatic hydrocarbons such as benzene, toluene and xylene; ethers such as dimethyl ether, diethyl ether, diisopropyl ether, tetrahydrofuran, dioxane and diethylene glycol; halogenated hydrocarbons such as dichloromethane, chloroform and carbon tetrachloride; lower alcohols such as methanol, ethanol, isopropanol, butanol and tert-butanol; ketones such as methyl ethyl ketone; acetic acid, ethyl acetate, acetone, acetonitrile, pyridine, dimethyl sulfoxide, dimethylformamide, and hexamethylphosphoryl triamide; and mixed solvents thereof can be exemplified. The above-mentioned reaction can advantageously be carried out by using basic material. As to the basic material, carbonates such as sodium carbonate, potassium carbonate, sodium hydrogen carbonate and potassium hydrogen carbonate; metal hydroxides such as sodium hydroxide, and potassium hydroxide; sodium hydride, metallic potassium, metallic sodium, sodium amide, alkali metal alcoholate such as sodium methylate and sodium ethylate; organic basic compounds such as pyridine, N-ethyldiisopropylamine, dimethylaminopyridine, triethylamine, tripropylamine, DBN, DBU and DABCO can be exemplified. The reaction is carried out generally at about room temperature to 200° C., preferably at about room temperature to 100° C., and generally the reaction is completed in about 1 to 24 hours. Into the reaction system, an alkali metal halide, such as sodium iodide or potassium iodide may be added.

Reaction formula-5

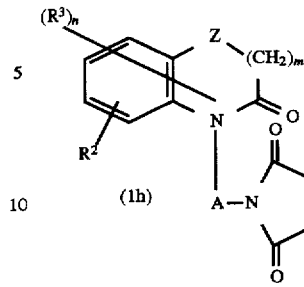

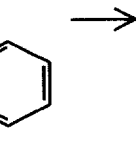

In the Reaction formula-5, $R^2$, $R^3$, n, m, Z and A are the same as defined above.

In the above-mentioned Reaction formula-5, the reaction for introducing a compound represented by the general formula (1h) to a compound represented by the general formula (1i) can be carried out by reacting a compound of the general formula (1h) with hydrazin monohydrate without solvent or in an inert solvent. Ratio of the used amounts of compound (1h) to hydrazin monohydrate is not specifically restricted, and can be selected from a wide range, and generally an equimolar to an excess quantity, preferably an equimolar to 5 times the molar quantity of the latter may be used to the molar quantity of the former. As to the inert solvent to be used, aromatic hydrocarbons such as benzene, toluene and xylene; ethers such as tetrahydrofuran, dioxane, diethylene glycol dimethyl ether, diethyl ether, diisopropyl ether and ethylene glycol; lower alcohols such as methanol, ethanol, isopropanol and butanol; acetic acid, ethyl acetate, acetone, acetonitrile, dimethyl sulfoxide, dimethylformamide, hexamethylphosphoryl triamide can be exemplified. The reaction is generally carried out at about room temperature to 150° C., preferably at room temperature to 100° C., and the reaction is generally completed in about 1 to 24 hours.

Reaction formula-6

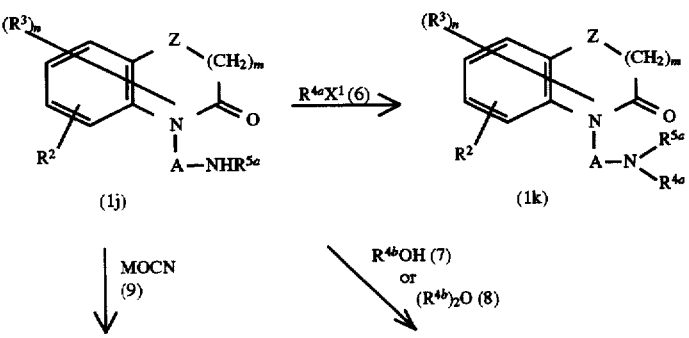

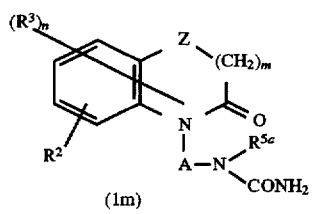
(1m)

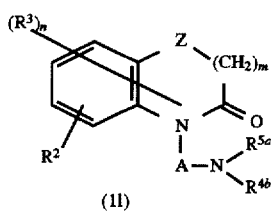
(1l)

In the Reaction formula-6, $R^2$, $R^3$, n, m, Z, $X^1$ and A are the same as defined above; $R^{4a}$ is a phenylsulfonyl group which may have lower alkyl group(s) as substituent(s) in the phenyl ring, a lower alkoxy-lower alkyl group, a lower alkyl group, a hydroxyl group-substituted lower alkyl group, a lower alkoxycarbonyl group-substituted lower alkyl group or a carboxy-substituted lower alkyl group; $R^{4b}$ is a lower alkanoyl group which may have halogen atom(s) as substituent(s); $R^{5a}$ is a hydrogen atom, a carbamoyl group, a lower alkanoyl group which may have halogen atom(s), a phenylsulfonyl group which may have lower alkyl group(s) as substituent(s) in the phenyl ring, a lower alkoxy-lower alkyl group, a lower alkyl group, a hydroxyl group-substituted lower alkyl group, a lower alkoxycarbonyl-substituted lower alkyl group or a carboxy-substituted lower alkyl group; and M is alkali metal such as sodium or potassium.

The reaction of a compound represented by the general formula (1j) with a compound represented by the general formula (6) is carried out under condition similar to that employed in the reaction of a compound of (1f) with a compound of (5) as disclosed in the Reaction formula-4.

The reaction of a compound of the general formula (1j) with a compound of the general formula (9) is carried out in the absence or presence of an acid, in a suitable solvent. As to the acid to be used, organic acids such as acetic acid and trifluoroacetic acid; mineral acids such as hydrochloric acid and sulfuric acid can be exemplified. As to the solvent to be used, alcohols such as methanol, ethanol, propanol, butanol, 3-methoxy-1-butanol, ethyl cellosolve and methyl cellosolve; pyridine; acetone; water; halogenated hydrocarbons such as dichloromethane, dichloroethane and chloroform; aromatic hydrocarbons such as benzene, toluene and xylene; ethers such as dimethoxyethane, tetrahydrofuran, diethyl ether and diisopropyl ether; esters such as ethyl acetate and methyl acetate; aprotic polar solvents such as N,N-dimethylformamide, dimethyl sulfoxide, acetonitrile and hexamethylphosphory triamide; and mixed solvents thereof can be exemplified. The amount of compound (9) may be used in generally, an equimolar quantity to an excess quantity, preferably an equimolar quantity to about 5 times the molar quantity to the molar quantity of a compound of (1j). The reaction is generally carried out at 0° to 150° C., preferably at room temperature to 100° C., and generally the reaction is completed in about 10 minutes to 15 hours.

The reaction of a compound of the general formula (1j) with a compound represented by the general formula (7) or (8) is carried out in the presence of a basic compound, in a suitable solvent. As to the basic compound to be used, known basic compounds can selected from a wide range, thus organic bases such as triethylamine, trimethylamine, pyridine, dimethylaniline, DBN, DBU and DABCO; inorganic bases such as potassium carbonate, sodium carbonate, potassium hydrogen carbonate, sodium hydrogen carbonate; sodium hydroxide, potassium hydroxide, sodium hydride and potassium hydride can be exemplified. As to the solvent to be used, alcohols such as methanol, ethanol, propanol, butanol, 3-methoxy-1-butanol, ethyl cellosolve and methyl cellosolve; pyridine; acetone; water; halogenated hydrocarbons such as chloromethane, dichloroethane and chloroform; aromatic hydrocarbons such as benzene, toluene and xylene; ethers such as dimethoxyethane, tetrahydrofuran, diethyl ether and diisopropyl ether; esters such as ethyl acetate and methyl acetate; aprotic polar solvents such as N,N-dimethylformamide, dimethyl sulfoxide, acetonitrile and hexamethylphosphoryl triamide can be exemplified. The ratio of used amounts of a compound of the general formula (1j) to a compound of the general formula (7) or (8) is not specifically restricted, and can be selected from a wide range, generally an equimolar quantity to an excess quantity, preferably an equimolar to 5 times the molar quantity of the latter may be used to the molar quantity of the former. The reaction is generally carried out at −20° to about 180° C., preferably at 0° to about 150° C., and the reaction is generally completed in about 5 minutes to 30 hours.

Reaction formula-7

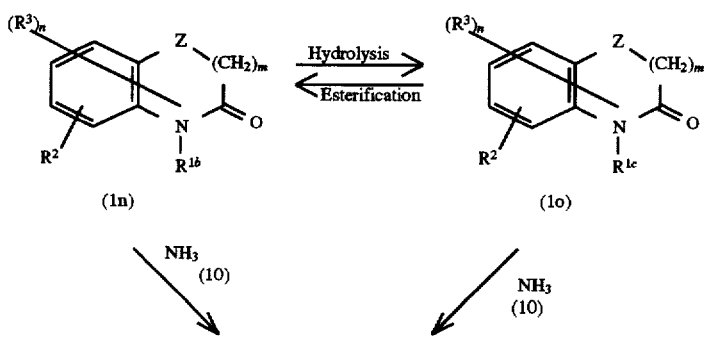

-continued

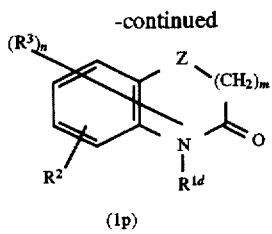

(1p)

In the Reaction formula-7, $R^2$, $R^3$, n, m and Z are the same as defined above; $R^{1b}$ is a lower alkoxycarbonyl-substituted lower alkyl group, a lower alkanoyloxy-lower alkyl group or a group of the formula:

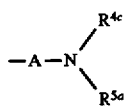

(wherein A and $R^{5a}$ are the same as defined above; and $R^{4c}$ is a lower alkoxycarbonyl-substituted lower alkyl group); $R^{1c}$ is a carboxy-substituted lower alkyl group, a hydroxyl group-substituted lower alkyl group or a group of the formula:

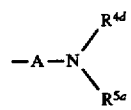

(wherein A and $R^{5a}$ are the same as defined above; and $R^{4d}$ is a carboxy-substituted lower alkyl group); and $R^{1d}$ is a carbamoyl-substituted lower alkyl group.

In the Reaction formula-7, the hydrolysis reaction of a compound represented by the general formula (1n) can be carried out without solvent or in a suitable inert solvent, in the presence of an acid or basic compound. As to the solvent to be used, water; a lower alcohol such as methanol, ethanol and isopropanol; ketones such as acetone and methyl ethyl ketone; ethers such as dioxane, tetrahydrofuran and ethylene glycol dimethyl ether; fatty acids such as acetic acid and formic acid; dimethylformamide; and mixed solvents thereof can be exemplified. As to the acid, mineral acids such as hydrochloric acid, sulfuric acid, hydrobromic acid, phosphoric acids and polyphosphoric acids; organic acids such as formic acid, acetic acid and aromatic sulfonic acids can be exemplified. Furthermore, as to the basic compounds, metal carbonates such as sodium carbonate and potassium carbonate; metal hydroxides such as sodium hydroxide, potassium hydroxide and calcium hydroxide; sodium acetate can be exemplified. Generally, the reaction is carried out at room temperature to about 150° C., preferably at room temperature to about 100° C. and is completed generally in about 10 minute to 25 hours. Ratio of used amount of a compound (1n) to the amount of acid or basic compound is not specifically restricted, and generally an equimolar quantity to an excess quantity, preferably an equimolar quantity to 5 times the molar quantity of the latter may be used to the molar quantity of the former.

Among the compound represented by the general formula (1o), esterification reaction of the compound wherein $R^{1c}$ is a carboxy-substituted lower alkyl group

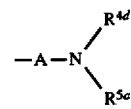

(wherein A, $R^{4d}$ and $R^{5a}$ are the same as defined above) can be carried out by reacting a compound of the formula (1o) with an alcohol such as methanol, ethanol or isopropanol, generally at 0° to 150° C., preferably at 50° to 100° C., for about 5 minutes to 10 hours, in the presence of a mineral acid such as hydrochloric acid or sulfuric acid; or halogenating agent such as thionyl chloride, phosphorus oxychloride, phosphorus pentachloride or phosphorus trichloride.

Among the compounds represented by the general formula (1n), a compound having a lower alkoxycarbonyl substituted-lower alkyl group as to $R^{1b}$, or among the compounds represented by the general formula (1o), a compound having carboxy-substituted lower alkyl group as to $R^{1c}$ the reaction with ammonia (10) can be carried out easily in a suitable inert solvent. Ratio of the used amount of a compound of the general formula (1n) or (1o) to the used amount of ammonia (10) is not specifically restricted and can be selected from a wide range, and generally an equimolar quantity to an excess quantity, preferably 2 to 10 times the molar quantity of the latter may be used to the molar quantity of the former. As to the inert solvent, water is generally used, and lower alcohols such as methanol, ethanol and isopropanol; ethers such as dioxane, ethylene glycol, tetrahydrofuran and ethylene glycol dimethyl ether; dimethyl sulfoxide, dimethylformamide, hexamethylphosphoryl trimide, pyridine, acetone, acetonitrile and mixed solvents thereof can be exemplified. The reaction is carried out, generally at room temperature to 150° C., preferably at room temperature to 100° C., and generally the reaction is completed in about 1 to 30 hours.

Reaction formula-8

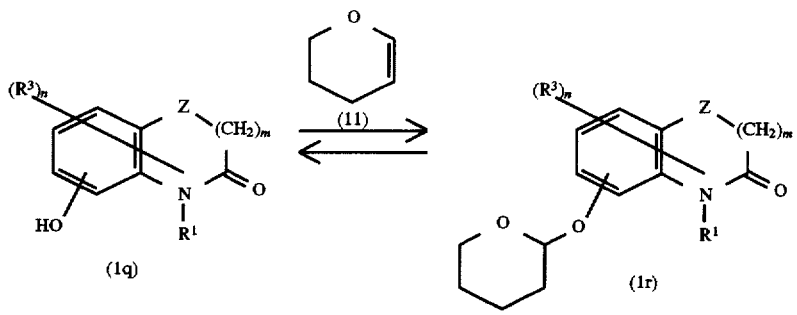

In the Reaction formula-8, $R^1$, $R^3$, n, m and Z are the same as defined above.

The reaction of a compound represented by the general formula (1q) with a compound represented by the general formula (11) is carried out, in the presence of an acid, in a suitable solvent or without solvent. As to the acid to be used, organic acids such as acetic acid, trifluoroacetic acid, formic acid and aromatic sulfonic acid; and mineral acids such as hydrochloric acid, sulfuric acid, hydrobromic acid and phosphoric acids can be exemplified. As to the solvent to be used, alcohols such as methanol, ethanol, propanol, butanol and 3-methoxy-1-butanol; halogenated hydrocarbons such as chloroform, dichloromethane and dichloroethane; aromatic hydrocarbon such as benzene, p-chlorobenzene, toluene and xylene; ethers such as diethyl ether, diisopropyl ether, tetrahydrofuran and dimethoxyethane; esters such as methyl acetate and ethyl acetate; aprotic polar solvents such as N,N-dimethylformamide, dimethyl sulfoxide, acetonitrile and hexamethylphosphoryl triamide; pyridine; acetone; water; and mixed solvents thereof can be exemplified.

Used amount of a compound (11) may be generally at least an equimolar quantity, preferably an equimolar quantity to an excess quantity to the molar quantity of a compound (1q). The reaction is carried out generally at room temperature to 150° C., preferably at room temperature to around 100° C., and the reaction is generally completed in about 10 minutes to 12 hours.

A compound of the general formula (1q) can be obtained by heating the compound of the general formula (1r) in the presence of a suitable acid, and in a suitable solvent or without solvent, generally at room temperature to 150° C., preferably at room temperature to around 100° C. for about 10 minutes to 12 hours. As to the acid to be used, organic acids such as acetic acid, trifluoroacetic acid, formic acid and aromatic sulfonic acid; and mineral acids such as hydrochloric acid, sulfuric acid, hydrobromic acid and phosphoric acids can be exemplified. As to the solvent to be used, alcohols such as methanol, ethanol, propanol, butanol and 3-methoxy-1-butanol; halogenated hydrocarbons such as chloroform, dichloromethane and dichloroethane; aromatic hydrocarbon such as benzene, p-chlorobenzene, toluene and xylene; ethers such as diethyl ether, diisopropyl ether, tetrahydrofuran and dimethoxyethane; esters such as methyl acetate and ethyl acetate; aprotic polar solvents such as N,N-dimethylformamide, dimethyl sulfoxide, acetonitrile and hexamethyl-phosphoryl triamide; pyridine; acetone; water; and mixed solvents thereof can be exemplified.

Reaction formula -9

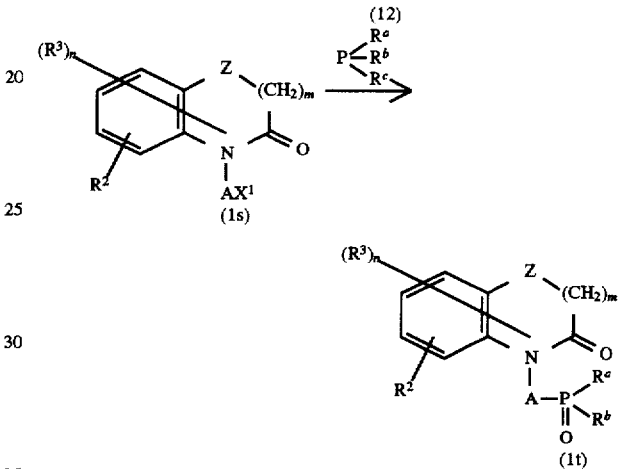

In the reaction formula -9, $R^2$, $R^3$, n, m, z, A and $X^1$ are the same as defined above; $R^a$, $R^b$ and $R^c$ are each the same or different, and is a lower alkoxy group or a hydroxyl group.

The reaction of a compound represented by the general formula (1s) with a compound represented by the general formula (12) can easily be carried out without solvent or in a suitable inert solvent. Ratio of the used amounts of a compound of the general formula (1s) to a compound of the general formula (12) is not specifically restricted, and can be selected from a wide range, generally an equimolar quantity to an excess quantity, preferably an equimolar quantity to 5 times the molar quantity of the latter may be used to the molar quantity of the former. As to the inert solvent to be used aromatic hydrocarbon such as benzene, toluene and xylene; ethers such as dimethyl ether, diethyl ether, diisopropyl ether, tetrahydrofuran, dioxane and diethylene glycol; halogenated hydrocarbons such as dichloromethane, chloroform and carbon tetra-chloride; lower alcohols such as methanol, ethanol, isopropanol, butanol and tert-butanol; ketones such as methyl ethyl ketone; acetic acid, ethyl acetate, acetone, acetonitrile, pyridine, dimethyl sulfoxide, dimethylformamide and hexamethylphosphoryl triamide; and mixed solvents thereof can be exemplified. The above-mentioned reaction is carried out advantageously by using a basic material. As to the basic materials, carbonates such as sodium carbonate, potassium carbonate, sodium hydrogen carbonate and potassium hydrogen carbonate; metal hydroxide such as sodium hydroxide and potassium hydroxide; sodium hydride; metallic potassium, metallic sodium; sodium amide; metal alcoholates such as sodium methylate and sodium ethylate; organic basic compounds such as pyridine, N-ethyldiisopropylamine, dimethylaminopyridine, triethylamine, tripropylamine, DBN, DBU and DABCO can be exemplified. The reaction is carried out generally at room temperature to 250° C., preferably at room temperature to around 180° C., and the reaction is completed generally in about 1 to 24 hours. Into the reaction system, alkali metal halide such as sodium iodide or potassium iodide may be added.

Among cyclic amide derivatives represented by the general formula (1) of the present invention, those having acidic group can be formed corresponding salts thereof by treating with pharmacologically acceptable basic compounds. As to the basic compounds, metal hydroxides such as sodium hydroxide, potassium hydroxide, lithium hydroxide and calcium hydroxide; alkali metal carbonates or bicarbonates such as sodium carbonate and sodium hydrogen carbonate; alkali metal alcoholates such as sodium methylate and potassium ethylate can be exemplified. Among cyclic amide derivatives represented by the general formula (1) of the present invention, those having basic group can be formed corresponding salts thereof by treating with pharmacologically acceptable acids. As to the acids, inorganic acids such as sulfuric acid, nitric acid, hydrochloric acid and hydrobromic acid; organic acids such as acetic acid, p-toluenesulfonic acid, ethane-sulfonic acid, oxalic acid, maleic acid, citric acid, succinic acid and benzoic acid can be exemplified.

The above-mentioned cyclic amide derivatives represented by the general formula (1) involve inevitably their optical isomers.

The objective compounds obtained by various methods of each one of these Reaction formulae-1 to -9 are separated from the reaction system by methods of usual separation means, and can be further purified. As to such separation and purification methods, distillation method, recrystallization method, column chromatography, ion exchanging chromatography, gel chromatography, affinity chromatography, preparative thin layer chromatography and solvent extraction method can be exemplified.

POSSIBILITY OF INDUSTRIAL UTILIZATION

Thus obtained cyclic amide derivatives of the present invention are used as in the form of general preparations of pharmaceutical compositions. Said preparations are prepared by using common diluents or excipients for example fillers, bulking agents, binding agents, wetting agents, disintegrators, surface-active agents, lubricants and the like. These preparations of pharmaceutical compositions can be selected from various forms in accordance with the therapeutical purposes. As to the typical forms thereof, tablets, pills, powders, liquors, suspensions, emulsions, granules, capsules, suppositories, injection preparations (solutions, suspensions), eye drops and eye ointments and the like. Furthermore, inhalants, spraying preparations such as external aerosol preparations, liquid coatings, lotions, gels, oily ointments, emulsion type ointments such as O/W type hydrophilic ointments and W/O type water-absorbing ointments, water-soluble ointments, creams, liniments, cataplasmas, dermatological pastes, plasters, emulsions for external use, and sheet form preparations can be exemplified.

For the purpose to shape in the form of tablets, carriers which are widely known in this field can be used. For example, excipients such as lactose, white sugar, sodium chloride, glucose, urea, starch, calcium carbonate, kaolin, crystalline cellulose and silicic acid; bindering agents such water, ethanol, propanol, simple syrup, glucose solution, starch solution, gelatin solution, carboxymethylcellulose, shelac, methyl cellulose, potassium phosphate and polyvinylpyrrolidon; disintegrating agents such as dried starch, sodium alginate, agar-agar powder, lainalia powder, sodium hydrogen carbonate, calcium carbonate, polyoxyethylene sorbitan fatty acid esters, sodium laurylsulfate, monoglyceride of stearate, starch and lactose; disintegration inhibiting agents such as white sugar, stearin, coconut butter and hydrogenated oils; absorption accelerators such as quaternary ammonium bases and sodium laurylsulfate; wetting agent such as glycerin and starch; adsorption agents such as starch, lactose, kaolin, bentonite and colloidal silicic acid; lubricants such as refined talc, stearates, boric acid powder, and polyethylene glycol, can be exemplified. In case of preparing tablets, if necessary, they can be further coated with usual coating materials, for example make them into tablets coated with sugar, tablets coated with gelatin film, tablets coated with enteric coatings, tablets coated with films or double layer tablets as well as multiple layer tablets.

For the purpose to shape in the form of pills, any carrier which is known and used widely in this field can be used. For example, excipients such as glucose, lactose, starch, coconut butter, hydrogenated vegetable oils, kaolin and talc; binding agents such as powdered gum arabic, powdered tragacanth gum, gelatin and ethanol; disintegrating agents such as laminalia and agar-agar are included can be used.

For the purpose to shape in the form of suppositories, carriers which are known and widely used in this field can be used. For example, polyethylene glycols, coconut butter, higher alcohols, esters of higher alcohols, gelatin and semi-synthesized glycerides can be used.

Capsule preparations are prepared in accordance with conventional method, by mixing the active ingredient compounds with the above-exemplified various carriers, then the mixture is filled in hard gelatine capsules or soft capsules.

In the case of prepare injection preparations, solutions, emulsion and suspensions are sterilized and are preferably make them isotonic to the blood. In making the preparations in the form of injections, the all of diluents which are widely used in this field can be used. For example, water, ethyl alcohol, macrogol, propylene glycol, ethoxylated isostearyl alcohol, polyoxylated isostearyl alcohol and polyoxyethylene sorbitan fatty acid esters can be used. In this case, adequate amount of sodium chloride, glucose or glycerin may be added to the desired injection preparations to make them isotonic to the blood, further usual dissolving agents, buffering agents and analgesic agents can be added. If necessary, coloring agents, preservative agents, perfumes, seasoning agents, sweetening agents and other medicines can also be added into the desired injection preparations.

In case of prepare eye drops and eye ointments, the base materials are suitably selected in accordance with desired form of the preparation, and thus preparations are sterilized. For example, in case of prepare an eye ointment, any type of conventional emulsion-ointment base, water-soluble ointment base and suspension-ointment base can be used. As to typical example of these base materials, white petrolatam, refined lanolin and liquid paraffin can be used. In case of prepare an eye drops, as to the typical base material, sterilized distilled water can be used.

The amount of cyclic amide derivative of the general formula (1) or salt thereof of the present invention to be contained in the preparation of pharmaceutical composition is not specifically restricted, and it can suitably be selected from a wide range, and generally it may be contained about 1 to 70% by weight in the whole composition.

Method for administering the pharmaceutical compositions of the present invention is not specifically restricted, and they can be applied in various preparation forms, and is administered in accordance with age of the patient, distinction of the sex, other conditions and degree of the symptoms. For example, tablets, pills, liquid preparations, suspension preparations, emulsion preparations, granular preparations and capsule preparations are administered orally. In case of using injection preparations, they are administered intravenously singly or in combination with usual injection preparations such as glucose solutions and amino acids solutions. If necessary, the injection preparations are administered singly intramuscularly, intracutaneously, subcutaneously or intraperitoneally. The suppositories are administered into the rectum. In case of the preparation for external use, they are applied to the affected parts.

In case of using the cyclic amide derivative of the present invention as in the form of cosmetics, it is added in skin creams, skin lotions or skin oils for sunburn protection and sunburn prevention. Furthermore, it is added into general cosmetics as for protecting ultraviolet rays and for preventing ultra-violet rays, and also added as the active ingredient in agent for protecting sunburn and in agent for sunburn prevention.

Cosmetic preparations are concretely exemplified such as shampoo, body-shampoo, perfume, eau de cologne, nail enamel, enamel remover, dentifrice, rinse, face powder, eye liner, mascara, eye blow, hair grooming preparation (hair conditioner, hair grower), common skin cream, milky lotion (for protection, cleansing and conditioning the skin), shaving cream, shaving lotion, eye cream, common toilet water (for emollient, cleansing and conditioning the skin), pack, cleansing preparation, beauty oil, bath cosmetics, hair color, nail cream, mouth washes, bleaching preparation, acne preparation, permanent wave preparation, and hair remover.

As to the forms of these cosmetics, liquid preparation, oil preparation, lotion, liniment, oleaginous ointment base, emulsion type ointment base for O/W type hydrophilic ointment and W/O type water-absorbing ointment, water-soluble ointment base, dermatological paste, plaster, adhesive plaster, cream and milk lotion can be exemplified, and such forms may not be restricted within these range. The cosmetics in the form of these types can be prepared in accordance with conventional methods which are known and widely used in this field.

For example, the ointment bases are used singly or in combination with 2 or more of oily bases, and are used singly or in combination with 2 or more of water-soluble ointment bases. As to these ointment bases are concretely exemplified such as, peanut oil, sesame oil, soybean oil, sufflower oil, avocado oil, sunflower oil, corn oil, rapeseed oil, cottonseed oil, castor oil, camelliaseed oil, coconut oil, olive oil, poppy oil, cacao butter, beef tallow, hog fat lard, lanolin and the like; chemically reformed products of these ointment bases by hydrogenation and the like; mineral oils such as petrolatum, paraffin oil and paraffin wax; silicone oil; squalane oil; higher fatty acid esters, higher fatty alcohols and waxes such as isopropyl myristate, n-butyl myristate, isopropyl linolate, propyl ricinolate, isopropyl ricinolate, isobutyl ricinolate, heptyl ricinolate, diethyl sebacate, diisopropyl adipate, cetyl alcohol, stearyl alcohol, bleached bees wax, spermaceti, Japan wax, lanolins, carnauba wax and shellac wax; higher fatty acids such as stearic acid, oleic acid and palmitic acid; mixtures of mono- di- and tri-glycerides of saturated or unsaturated fatty acids having 12 to 18 carbon atoms; polyhydric alcohols such as ethylene glycol, polyethylene glycols, propylene glycol, polypropylene glycols, glycerin, batyl alcohol, pentaerythritol, sorbitol, and mannitol; vegetable gums such as gum arabic, gum benzoin, guaiac resin and gum tragacanth; natural water-soluble macromolecules such as gelatin, starch, casein, dextrin, pectin, pectin sodium, sodium alginate, methyl cellulose, ethyl cellulose, carboxymethyl cellulose, hydroxyethyl cellulose, hydroxypropyl cellulose, nitrocellulose and crystalline cellulose; synthetic water-soluble macro-molecules such as polyvinyl alcohols, polyvinylmethyl ethers, polyvinylpyrrolidones, sodium polyacrylates, carboxyvinyl polymers and polyethyleneimines; surface active agents such as nonionic surfactants, cathionic surfactants, amphoteric surfactants and anionic surfactants; ethanol, isopropanol and water.

In case of preparing the above-mentioned cosmetic products, various types of cosmetic base materials known in the art, for example excipients, binding agents, lubricants and disintegrating agents can be used in accordance with the necessity. Further, if necessary, various types of oils and fats, waxes, hydrocarbons, fatty acids, higher alcohols; oily materials such as ester oils and metallic soaps; liquid extracts of animals and vagetables; medicinal agents such as vitamins, hormons and amino acids; surface active agents, colors, dyestuffs, pigments, perfumes, preservatives, germicides, wetting agent, thickening agents, antioxidants and metal chelating agents; as well as various types of ingredients and additives which are known in the art can be used by combining thereof. In addition to the above, these cosmetic preparations thus obtained can also be used by diluting with suitable solvent such as water or olive oil.

The amount of cyclic amide derivative represented by the general formula (1) or salt thereof of the present invention to be contained as the active ingredient in the cosmetic preparations is not specifically restricted and it can be selected suitably from a wide range, and generally the cyclic amide derivative or salt thereof may be contained about 0.1 to 50% by weight.

Administration dose of the cyclic amide derivative represented by the general formula (1) or salt thereof being contained as the active ingredient in the preparation of pharmaceutical composition or the cosmetic preparation of the present invention may be selected in accordance with method of administration, age of the patient, distinction of the sex and other conditions, degree of disease and so forth. Generally in case of using as for pharmaceutical composition, about 0.6 to 50 mg/kg of the body weight/day of the active ingredient may be administered, and in case of using as for cosmetic preparation, about 0.1 to 30 mg/kg of the body weight/day of the active ingredient may be administered. These preparations may be administered divisionally in 2 to 4 times a day.

EXAMPLES

The present invention will be explained in detail by showing Reference examples, Examples and Pharmacological test results as follows.

Reference Example 1

32.6 Grams of 3,4-dihydro-6-hydroxy-2(1H)-quinolinone was dissolved in 500 ml of methanol containing 12.6 g of potassium hydroxide. Under stirring this solution, 20 ml of allyl bromide was added thereto at room temperature. The reaction mixture was stirred at room temperature for 1 hour, and further stirred at 60° C. for 4 hours. After the reaction, the reaction mixture was concentrated to a half volume under reduced pressure, then 500 ml of water was added and stirred vigorously, the crystals precipitated were collected by filtration. The crystals were washed with water and small amount of diethyl ether in this order, and dried. Recrystallized from ethanol, 28 g (68.9%) of 6-allyloxy-3,4-dihydro-2(1H)-quinolinone was obtained. Colorless needle-like crystals (recrystallized from ethanol)

Melting point: 123°–125° C.

By using suitable starting materials, and employing the reaction condition as well as after treatment procedures similar to those carried out in Reference example 1, there were prepared compounds of Reference Examples 2 to 6 as follows.

Reference Example 2

7-Allyloxy-3,4-dihydro-2(1H)-quinolinone

Colorless needle-like crystals (recrystallized from ethanol)

Melting point: 98°–101°.

Reference Example 3

6-Allyloxy-2(1H)-quinolinone

Colorless needle-like crystals (recrystallized from methanol)

Melting point: 193°–194°.

Reference Example 4

7-Allyloxy-2(1H)-quinolinone

Colorless needle-like crystals (recrystallized from methanol)

Melting point: 151°–153° C.

Reference Example 5

7-Allyloxy-3(2H)-1,4-benzoxazinone $^1$H-NMR (CDCl$_3$, TMS, ppm):

4.49–4.53 (2H, m), 4.59 (2H, s), 5.25–5.45 (2H, m), 5.95–6.10(1H, m), 6.50–6.59 (2H, m), 6.72 (1H, d), 8.51 (1H, s).

Reference Example 6

6-Allyloxy-3(2H)-1,4-benzoxazinone $^1$H-NMR (CDCl$_3$, TMS, ppm):

4.48–4.52 (2H, m), 4.57 (2H, s), 5.25–5.46 (2H, m), 5.92–6.10 (1H, m), 6.42 (1H, d), 6.45 (1H, d—d), 6.88 (1H, d), 8.76 (1H, s).

Reference Example 7

10.2 Grams of 6-allyloxy-3,4-dihydro-2(1H)-quinolinone was dissolved in 100 ml of dimethyl-formamide (DMF), then at room temperature, 2.2 g of 60% oily sodium hydride was added little by little thereto, and the reaction mixture was stirred at 25° to 40° C. until generation of hydrogen was stopped. The reaction mixture was cooled to room temperature, 9.1 g of prenyl bromide was added thereto and stirred at room temperature for 8 hours. After the reaction was completed, water was added, and the reaction mixture was extracted with methylene chloride. The methylene chloride extract was washed with water and an aqueous solution saturated with sodium chloride in this order, then thus washed extract was dried with anhydrous magnesium sulfate. Magnesium sulfate was removed by filtration and concentrated. Thus obtained oily residue was subjected to refining and separating by means of a silica gel flush column chromatography by using mixed solvent of ethyl acetate:n-hexane (1:10 to 1:2) as an eluent to obtain 10.2 g (59.7%) of 6-allyloxy-3,4-dihydro-1-prenyl-2-(1H)-quinolinone.

Light yellow oily substance:

$^1$H-NMR (CDCl$_3$, ppm):

1.74 (3H, s), 1.82 (3H, s), 2.61–2.69 (2H, m), 2.88–2.92 (2H, m), 4.52–4.56 (2H, m), 5.11–5.17 (1H, m), 5.28–5.49 (2H, m), 5.98–6.15 (2H, m), 8.77–8.92 (3H, m).

Reference Example 8

10.2 Grams of 6-allyloxy-2(1H)-quinolinone was dissolved in 100 ml of dimethylformamide, then 2.2 g of 60% oily sodium hydride and 9.1 g of prenyl bromide were added thereto by the procedures similar to those employed in Reference example 7 and reacted. Then, thus obtained reaction mixture was treated and oily mixture was obtained. This mixture was subjected to separation and refining by means of a silica gel flush column chromatography in which a mixture of ethyl acetate:n-hexane (1:10 to 1:2) was used as an eluent. Colorless to light yellow oily product, which was obtained by concentrating the second eluate portion under reduced pressure, was allowed to stand at room temperature, then it was crystallized. There was obtained 4.7 g (34.9%) of 6-allyloxy-2-prenyloxy-quinoline by recrystallization from n-hexane. Colorless needle-like crystals (recrystallized from n-hexane)

Melting point: 53°–54° C.

Reference Example 9

The third eluate portion of silica gel flush column chromatography of Reference example 8 was collected, and concentrated under reduced pressure. Thus obtained oily product was allowed to stand at room temperature, then it was crystallized to obtain 5.7 g (43.4%) of 6-allyloxy-1-prenyl-2(1H)-quinolinone. Colorless granular crystals (recrystallized from n-hexane)

Melting point: 80°–82° C.

Reference Example 10

2 Grams of 6-allyloxy-3,4-dihydro-2(1H)-quinolinone was dissolved in 50 ml of dimethyl-formamide, then 0.5 g of 60% oily sodium hydride and 5 ml of p-bromoanisole were added thereto by the procedures similar to those employed in Reference example 7, further 4 g of cuprous chloride was added, and stirred at 120° C. for 24 hours. The inorganic materials were removed by filtration, and the filtrate was concentrated under reduced pressure. Thus obtained residual product was subjected to extraction with 200 ml of methylene chloride, the extract was washed with water and an aqueous solution saturated with sodium chloride. Then the extract was concentrated and subjected to purification by passing through a silica gel column, there was obtained 1.3 g (42%) of 6-allyloxy-3,4-dihydro-1-(4-methoxyphenyl)-2 (1H)-quinolinone.

Light yellow oily product.

$^1$H-NMR (CDCl$_3$, ppm):

2.79–2.69 (2H, t), 3.01 (2H, t), 3.85 (3H, s), 4.49–4.56 (2H, m), 5.24–5.44 (2H, m), 5.95–6.11 (1H, m), 6.30 (1H, d), 6.59 (1H, m), 6.78 (1H, d),7.00 (2H, d), 7.14 (2H, d).

By the procedure similar to that of employed in Reference example 7, there were obtained compounds of Reference examples 11–13; by the procedures similar to those of employed in Reference examples 8 and 9, there were obtained compounds of Reference examples 14 to 17; and by the procedure similar to those of employed in Reference example 10, there were obtained compounds of Reference examples 18 to 20, respectively as follows.

Reference Example 11

7-Allyloxy-3,4-dihydro-1-prenyl-2(1H)-quinolinone.

Light yellow oily product $^1$H-NMR (CDCl$_3$, ppm):

1.72 (3H, s), 1.80 (3H, s), 2.60–2.64 (2H, m), 2.80–2.86 (2H, m), 4.51–4.54 (4H, m), 5.10–5.13 (1H, m), 5.27–5.45 (2H, m), 5.98–6.11 (1H, m), 6.52–6.59 (2H, m), 7.04 (1H, d).

Reference Example 12

6-Allyloxy-1-cinnamyl-3,4-dihydro-2(1H)-quinolinone

Light yellow oily product $^1$H-NMR (CDCl$_3$, ppm):

2.68–2.73 (2H, m), 2.88–2.94 (2H, m), 4.49–4.53 (2H, m), 4.69–4.71 (2H, m), 5.27–5.45 (2H, m), 5.99–6.08 (1H, m), 6.22–6.31 (1H, m), 6.53 (1H, d), 6.74–6.77 (2H, m), 7.00 (1H, m), 7.21–7.37 (5H, m).

Reference Example 13

6-Allyloxy-1-(4-allyloxy-3-methoxybenzyl)-3,4-dihydro-2(1H)-quinolinone

Colorless needle-like crystals (recrystallized from diethyl ether-n-hexane). Melting point: 93°–65° C.

Reference Example 14

1-Allyl-6-allyloxy-2(1H)-quinolinone

Colorless granular crystals (recrystallized from petroleum ether), Melting point: 49°–51° C.

Reference Example 15

2,6-Diallyloxyquinoline

Colorless granular crystals (recrystallized from n-hexane) Melting point: 58°–60° C.

Reference Example 16

7-Allyloxy-1-prenyl-2(1H)-quinolinone

Light yellow oily product $^1$H-NMR (CDCl$_3$, ppm):

1.72 (3H, s), 1.89 (3H, s), 4.60–4.63 (2H, m), 4.89 (2H, d), 5.11–5.15 (1H, m), 5.31–5.48 (2H, m), 6.02–6.13 (1H, m), 6.55 (1H, d), 6.79–6.84 (3H, m), 7.44 (1H, d), 7.58 (1H, d).

Reference Example 17

7-Allyloxy-2-prenyloxyquinoline

Light yellow oily product $^1$H-NMR (CDCl$_3$, ppm):

1.82 (6H, s), 4.66–4.70 (2H, m), 4.99–5.01 (2H, m), 5.31–5.62 (3H, m), 6.76 (1H, d), 6.99–7.03 (3H, m), 7.21 (1H, d), 7.59 (1H, d), 7.92 (1H, d).

Reference Example 18

5-Allylyoxy-3,4-dihydro-1-phenyl-2(1H)-quinolinone

Light yellow oily product $^1$H-NMR (CDCl$_3$, ppm):

2.79 (2H, t), 3.11 (2H, t), 4.55–4.59 (2H, m), 5.25–5.50 (2H, m), 5.98 (1H, d), 6.00–6.20 (1H, m), 6.58 (1H, d), 7.21 (1H, t), 7.24–7.55 (5H, m).

Reference Example 19

6-Allyloxy-3,4-dihydro-1-(4-fluorophenyl)-2(1H)-quinolinone

Light yellow oily product $^1$H-NMR (CDCl$_3$, ppm):

2.79 (2H, t), 3.01 (2H, t), 4.49–4.56 (2H, m), 5.25–5.45 (2H, m), 5.95–6.11 (1H, m), 6.26 (1H, d), 5.68–6.62 (1H, m), 6.79 (1H, d), 7.13–7.14 (4H, m).

Reference Example 20

6-Allyloxy-3,4-dihydro-1-(3,4-dimethoxy-phenyl)-2(1H)-quinolinone

Light yellow oily product $^1$H-NMR (CDCl$_3$, ppm):

2.80 (2H, t), 3.03 (2H, t), 3.85 (3H, s), 3.93 (3H, s), 4.49–4.56 (2H, m), 5.24–5.45 (2H, m), 5.95–6.11 (1H, m), 6.33 (1H, d), 6.58–6.62 (1H, m), 6.71 (1H, d), 6.78–6.83 (2H, m), 6.97 (2H, d)

In place of the starting material of 6-allyloxy-3,4-dihydro-2(1H)-quinolinone used in Reference example 7, each of the starting materials of Reference examples 5 and 6 or 5-hydroxybenzoxazolinone was used, and by the procedure used in Reference example 7, there were prepared compounds of Reference examples 21–23 as follows.

Reference Example 21

4-Allyl-7-allyloxy-3(2H)-1,4-benzoxazinone

Yellow oily product $^1$H-NMR (CDCl$_3$, ppm):

4.45–4.55 (4H, m), 4.62 (2H, s), 5.25–5.45 (4H, m), 5.75–6.10 (2H, m), 6.50–6.60 (2H, m), 6.87 (1H, d).

Reference Example 22

4-Allyl-6-allyloxy-3(2H)-1,4-benzoxazinone

Yellow oily product $^1$H-NMR (CDCl$_3$, ppm):

4.45–4.54 (4H, m), 4.59 (2H, s), 5.15–5.45 (4H, m), 5.80–6.15 (2H, m), 6.53 (1H, d), 6.60 (1H, d), 6.90 (1H, d).

Reference Example 23

3-Allyl-5-allyloxybenzoxazolinone

Yellow oily product $^1$H-NMR (CDCl$_3$, ppm):

4.40–4.45 (2H, m), 4.50–4.55 (2H, m), 5.25–5.45 (4H, m), 5.80–6.15 (2H, m), 6.58 (1H, d), 6.63 (1H,, m), 7.08 (1H, d).

Example 1

10Grams of 6-allyloxy-2(1H)-quinolinone was suspended in 50 ml of tetralin, and this suspension was stirred at 200° to 230° C. for 4 hours in nitrogen gas atmosphere. After the reaction, the reaction mixture was cooled to room temperature. The crystals thus precipitated were collected by filtration, washed with n-hexane and a small amount of diethyl ether in this order and dried. There was obtained 10 g (100%) of 5-allyl-6-hydroxy-2(1H)-quinolinone as crystalline powder. Melting point: Decomposed from 290° C.

$^1$H-NMR (DMSO-$d_6$, ppm):

3.60 (2H, d), 4.88–4.97 (2H, m), 5.82–5.98 (1H, m), 6.45 (2H, d), 7.07 (2H, s), 7.92 (1H, d), 9.32 (1H, s), 12.50 (1H, s).

Example 2

4 Grams of 2,6-diallyloxyquinoline was reacted similarly as in Example 1, and the reaction mixture thus obtained was treated, there was obtained 4 g (100%) of 5-allyl-6-hydroxy-2(1H)-quinolinone as powdery crystals.

Example 3

2 Grams of 6-allyloxy-1-prenyl-2(1H)-quinolinone was reacted similarly as in Example 1, and the reaction mixture thus obtained was treated, there was obtained 2 g (100%) of 5-allyl-6-hydroxy-1-prenyl-2(1H)-quinolinone.

Pale yellow needle-like crystals (recrystallized from chloroform-methanol). Melting point: 224°–228° C.

Example 4

7.8 Grams of 7-allyloxy-1-prenyl-2(1H)-quinolinone was reacted similarly as in Example 1, and the reaction mixture thus obtained was treated, and dissolved in a small amount of chloroform, then the chloroform solution was subjected to purification by means of a silica gel flush column chromatography. The firstly eluted portion, which was eluted with methylene chloride-methanol (100:1–50:1) [i.e., the 1st eluate portion: 3.8 g (14.1%) of 8-allyl-7-hydroxy-3-prenyl-2 (1H)-quinolinone, pale yellow needle-like crystals, melting point: 138°–142° C.] was removed, then the secondary eluted portion (the 2nd eluate portion) was collected, concentrated and dried, there was obtained 0.8 g (10.3%) of 8-allyl-7-hydroxy-1-prenyl-2(1H)-quinolinone.

Pale yellow powdery crystals (recrystallized from ethyl acetate). Melting point: 198°–203° C.

Example 5

From the flush column chromatography in Example 4, the finally eluted portion was collected, concentrated and dried, there was obtained 4 g (14.9%) of 8-allyl-7-hydroxy-2(1H)-quinolinone.

White powdery crystals (recrystallized from methanol). Melting point: 207°–209° C.

Example 6

4 Grams of 1-allyl-6-allyoxy-2(1H)-quinolinone was reacted similarly as in Example 1 and treated, there was obtained 4 g (100%) of 1,5-diallyl-6-hydroxy-2(1H)-quinolinone. Colorless granular crystals (recrystallized from methanol). Melting point: 205°–206° C.

Example 7

20.3 Grams of 6-allyloxy-3,4-dihydro-2(1H)-quinolinone was reacted similarly as in Example 1 and treated, there was obtained 20 g (100%) of 1:1 mixture of 5-allyl-3,4-dihydro-6-hydroxy-2(1H)-quinolinone and 7-allyl-3,4-dihydro-6-hydroxy-2(1H)-quinolinone. To this mixture was added 1 liter of acetone and boiled for 1 hour, the insoluble matter was collected by filtration, washed with acetone and dried, there was obtained 6.7 g (33%) of 5-allyl-3,4-dihydro-6-hydroxy-2(1H)-quinolinone.

White crystalline powder. Melting point: 236°–239° C.

Example 8

From 20.3 g of 7-allyloxy-3,4-dihydro-2(1H)-quinolinone which was reacted similarly as in Example 1 and treated, there was obtained 18 g (88.7%) of mixture of 6-allyl-3,4-dihydro-7-hydroxy-2(1H)-quinolinone and 8-allyl-3,4-dihydro-7-hydroxy-2(1H)-quinolinone.

Example 9

5 Grams of 6-allyloxy-3,4-dihydro-1-prenyl-2(1H)-quinolinone was reacted similarly as in Example 1 and treated, thus obtained mixture was subjected to purification by means of a flush column chromatography by using ethyl acetate-n-hexane (1:100 to 1:25). The firstly eluted portion was collected and concentrated under reduced pressure. The residue thus obtained was recrystallized from ethyl acetate-n-hexane, there was obtained 0.8 g (16%) of 5-allyl-3,4-dihydro-6-hydroxy-1-prenyl-2(1H)-quinolinone.

Colorless needle-like crystals (recrystallized from ethyl acetate). Melting point: 182°–184° C.

Example 10

From the silica gel flush column chromatography in Example 9, the second eluted portion was collected, and the solvent was removed by distillation, there was obtained 1.8 g (36%) of 7-allyl-3,4-dihydro-6-hydroxy-1-prenyl-2(1H)-quinolinone.

Colorless plate crystals (recrystallized from ethyl acetate). Melting point: 148°–150° C.

Corresponding starting materials are reacted similarly as in Examples 9–10, and the reaction mixture thus obtained were subjected to separation and purification by means of silica gel column chromatography, there were obtained compounds of Examples 11 and 12 as follows.

Example 11

6-Allyl-3,4-dihydro-7-hydroxy-1-prenyl-2(1H)-quinolinone

Colorless needle-like crystals (recrystallized from water-containing ethanol). Melting point: 113°–114° C.

Example 12

8-Allyl-3,4-dihydro-7-hydroxy-1-prenyl-2(1H)-quinolinone.

Colorless granular crystals (recrystallized from diethyl ether). Melting point 143°–145° C.

Example 13

16 Grams of 6-allyloxy-1-cinnamyl-3,4-dihydro-2(1H)-quinolinone obtained in Reference example 12 was reacted similarly as in Example 1, and thus obtained reaction mixture was treated similarly, there was obtained 10.6 g (66.6%) of mixture of 7-allyl-1-cinnamyl-3,4-dihydro-6-hydroxy-2(1H)-quinolinone and 5-allyl-1-cinnamyl-3,4-dihydro-6-hydroxy-2(1H)-quinolinone. Said mixture was subjected to purification by means of a flush column chromatography. The thirdly eluted portion was collected, and concentrated under reduced pressure, there was obtained 7-allyl-1-cinnamyl-3,4-dihydro-6-hydroxy-2(1H)-quinolinone. Colorless granular crystals (recrystallized from ethanol). Melting point: 199°–203° C.

Example 14

6.1 Grams of the mixture of 6-allyl-3,4-dihydro-7-hydroxy-2(1H)-quinolinone and 8-allyl-3,4-dihydro-7-hydroxy-2(1H)-quinolinone obtained in Example 8 was dissolved in 200 ml of methanol containing 1.8 g of potassium hydroxide. Under stirring, 3 ml of allyl bromide was added thereto at room temperature. The reaction mixture was stirred at room temperature for 4 hours, and further stirred at 60° C. for 1 hour. After the reaction was finished, the reaction mixture was concentrated under reduced pressure, next 200 ml of water was added and stirred vigorously, then extracted with 500 ml of ethyl acetate. The extract was washed with water and an aqueous solution saturated with sodium chloride, and dried with anhydrous magnesium sulfate. The magnesium sulfate was removed by filtration, and the filtrate was concentrated to dryness. This mixture was subjected to purification by means of a flush column chromatography by using methylene chloride-methanol (100:1). The first eluted portion was collected and concentrated under reduced pressure, there was obtained 4.4 g (60%) of 8-allyl-7-allyloxy-3,4-dihydro-2(1H)-quinolinone. Colorless needle-like crystals (recrystallized from ethyl acetate-n-hexane). Melting point: 119°–121° C.

Example 15

From the flush column chromatography in Example 14, the secondary eluted portion was collected, concentrated and dried, there was obtained 2.8 g (38%) of 6-allyl-7-allyloxy-3,4-dihydro-2(1H)-quinolinone was obtained.

Colorless needle-like crystals (recrystallized from ethyl acetate-n-hexane). Melting point: 137°–139° C. Example 16

20.3 Grams of the mixture of 5-allyl-3,4-dihydro-6-hydroxy-2(1H)-quinolinone and 7-allyl-3,4-dihydro-6-hydroxy-2(1H)-quinolinone obtained in Example 7 was dissolved in 500 ml of methanol containing 12.6 g of potassium hydroxide. Under stirring, 20 ml of allyl bromide was added thereto at room temperature. The reaction mixture was stirred at room temperature for 1 hour, and further stirred at 60° C. for 4 hours. After the reaction was finished, the reaction mixture was concentrated under reduced pressure to a half volume, 500 ml of water was added thereto and stirred vigorously, then extracted with 500 ml of ethyl acetate. The ethyl acetate extract was washed with water and an aqueous solution saturated with sodium chloride, and dried with anhydrous magnesium sulfate. The magnesium sulfate was removed by filtration, and the filtrate was concentrated and dried. Recrystallized from ethyl acetate-n-hexane, there was obtained 18 g of the mixture of 5-allyl-6-allyloxy-3,4-dihydro-2(1H)-quinolinone and 7-allyl-6-allyloxy-3,4-dihydro-2(1H)-quinolinone. This mixture was used as the starting material in the next Example 17 without subjected to separating the two ingredients.

Example 17

10.2 Grams of the mixture of 5-allyl-6-allyloxy-3,4-dihydro-2(1H)-quinolinone and 7-allyl-6-allyloxy-3,4-dihydro-2(1H)-quinolinone obtained in Example 16 was dissolved in 100 ml of dimethylformamide, then 2.2 g of 60% oily sodium hydride was added little by little, and stirred at 25° to 40° C. until generation of hydrogen gas was ceased. After the reaction mixture was cooled to room temperature, 9.1 g of prenyl bromide was added and stirred at room temperature for 8 hours. After the reaction was finished, water was added and extracted with methylene chloride, then the extract was washed with water and an aqueous solution saturated with sodium chloride in this order, and dried with anhydrous magnesium sulfate. The magnesium sulfate was removed by filtration and the filtrate was concentrated. Thus obtained residual oily product was subjected to separation and purification by means of a silica gel flush column chromatography, there was obtained 10.2 g (59.7%) of 7-allyl-6-allyloxy-3,4-dihydro-1-prenyl-2(1H)-quinolinone.

Colorless granular crystals (recrystallized from ethanol). Melting point: 86°–88° C.

The mixture of 5-allyl-6-allyloxy-3,4-dihydro-2(1H)-quinolinone and 7-allyl-6-allyloxy-3,4-dihydro-2(1H)-quinolinone obtained in Example 16 was used as the starting materials, and reacted with cinnamyl bromide or cyclohexyl methyl chloride similarly as in Example 17, and thus obtained reaction mixture was treated similarly as in Example 17, then subjected to separation and purification by means of a silica gel column chromatography, there were obtained compounds of Examples 18 and 19 as follows.

Example 18

7-Allyl-6-allyloxy-1-cinnamyl-3,4-dihydro-2(1H)-quinolinone.

Colorless needle-like crystals (recrystallized from n-hexane).

Melting point: 76°–77° C.

Example 19

7-Allyl-6-allyloxy-1-cyclohexylmethyl-3,4-dihydro-2(1H)-quinolinone.

Yellow oily product.
$^1$H-NMR (CDCl$_3$, ppm):
0.96–1.20 (5H, m), 1.60–1.75 (6H, m), 2.59–2.63 (2H, m), 2.84 (2H, t), 3.41 (2H, d), 3.81 (2H, d), 4.51–4.54 (2H, m), 5.05–5.12 (2H, m), 5.25–5.47 (2H, m), 5.93–6.12 (1H, m), 6.66 (1H, s), 6.80 (1H, s)

Example 20

81 Grams of 6-allyl-7-allyloxy-3,4-dihydro-2(1H)-quinolinone obtained in Example 15 was dissolved in 500 ml of dimethylformamide, then 13 g of 60% oily sodium hydride and 50 g of prenyl bromide were added thereto and reacted similarly as in Example 17, after the reaction was finished, the reaction mixture was treated similarly, there was obtained yellow oily product. This oily product was subjected to treatment by means of a silica gel flush column chromatography by using a mixed solvent of methylene chloride-methanol (100:1) as the eluent. The secondary eluted portion was collected and concentrated, there was obtained 67 g (64.6%) of 6-allyl-7-allyloxy-3,4-dihydro-1-prenyl-2(1H)-quinolinone as pale yellow oily product. This oily product become a solid matter then it was allowed to stand at below 20° C., the solid matter was washed with ice-cooled petroleum ether to change white solid, dried in a desiccator and pulverized, there was isolated white powdery product.

Pale yellow oily or white solid. Melting point: 20–28° C.
$^1$H-NMR (CDCl$_3$, ppm):
1.73 (3H, s), 1.81 (3H, s), 2.58–2.66 (2H, m), 2.76–2.84 (2H, m), 4.48–4.53 (2H, m), 5.02–5.14 (3H, m), 5.25–5.45 (2H, m), 5.91–6.10 (2H, m), 6.52 (1H, s), 6.90 (1H, s).

Example 21

3.19 Grams of the mixture of 5-allyl-1-cinnamyl-3,4-dihydro-6-hydroxy-2(1H)-quinolinone and 7-allyl-1-cinnamyl-3,4-dihydro-6-hydroxy-2(1H)-quinolinone obtained in Example 13 was dissolved in 100 ml of methanol containing 1 g of potassium hydroxide. Under stirring, 2 g of cinnamy bromide was added thereto at room temperature, then stirred at room temperature for 1 hour, further stirred at 60° C. for 4 hours. After the reaction was finished, the reaction mixture was concentrated to a half volume under reduced pressure, 100 ml of water was added and stirred vigorously, then extracted with 200 ml of ethyl acetate. The extract was washed with water and an aqueous solution saturated with sodium chloride and dried with anhydrous magnesium sulfate. The magnesium sulfate was removed by filtration, the filtrate was concentrated to dryness. The residue was subjected to treatment by means of a silica gel flush column chromatography by using a mixed solvent of ethyl acetate: n-hexane as the eluent. The second eluted portion was collected and concentrated and crystallized from diethyl ether-n-hexane, there was obtained 1.8 g (41.4%) of 5-allyl-1-cinnamyl-6-cinnamyloxy-3,4-dihydro-2(1H)-quinolinone. Colorless granular crystals (recrystallized from diethyl ether-n-hexane). Melting point: 66°–68° C.

Example 22

From the flush column chromatography in Example 21, the later eluted portions were collected, concentrated and crystallized, there was obtained 2.0 g (45.9%) of 7-allyl-1-cinnamyl-6-cinnamyloxy-3,4-dihydro-2(1H)-quinolinone.

Colorless needle-like crystals (recrystallized from diethyl ether-n-hexane). Melting point: 88°–89° C.

By using 1-bromo-2-cyclohexene and treated similarly as in Examples 21 and 22, the compounds of Examples 23 and 24 were prepared.

Example 23

5-Allyl-1-cinnamyl-6-(2-cyclohexenyl)oxy-3,4-dihydro-2(1H)-quinolinone.

Colorless needle-like crystals (recrystallized from diethyl ether-n-hexane). Melting point: 103°–104° C.

Example 24

7-Allyl-1-cinnamyl-6-(2-cyclohexenyl)oxy-3,4-dihydro-2(1H)-quinolinone.

Yellow oily product $^1$H-NMR (CDCl$_3$, ppm):

1.55–2.20 (6H, m), 2.64 (2H, t), 2.89 (2H, t), 3.35 (2H, d), 4.69 (3H, d), 5.01–5.09 (2H, m), 5.83–5.97 (3H, m), 6.18–6.27 (1H, m), 6.56 (1H, d), 6.73 (1H, s), 6.73 (1H, s), 6.90 (1H, s), 7.01–7.35 (5H, m).

Example 25

2.43 Grams of the mixture obtained in Example 8 was dissolved in 20 ml of tetralin, and reacted similarly as in Example 1. After the reaction was finished, the reaction mixture was cooled to room temperature, and was subjected to purification by passing through a silica gel column, there was obtained 1.8 g (74%) of 6,8-diallyl-3,4-dihydro-7-hydroxy-2(1H)-quinolinone.

Cololess needle-like crystals (recrystallized from diethyl ether-n-hexane). Melting point: 86°–88° C.

Example 26

12.2 Grams of the mixture obtained in Example 16 was dissolved in 100 ml of tetralin, and reacted similarly as in Example 1. After the reaction was finished, the reaction mixture was cooled to room temperature, and was subjected to purification by passing through a silica gel column, there was obtained 8.7 g (71%) of 5,7-diallyl-3,4-dihydro-6-hydroxy-2(1H)-quinolinone.

Cololess needle-like crystals (recrystallized from methylene chloride-n-hexane). Melting point: 118°–119° C.

Example 27

2 Grams of 7-allyl-6-allyloxy-3,4-dihydro-1-prenyl-2(1H)-quinolinone obtained in Example 20 was dissolved in 20 ml of tetralin, and reacted similarly as in Example 1. After the reaction was finished, the reaction mixture was cooled to room temperature, and was subjected to purification by passing through a silica gel column, there was obtained 1 g (50%) of 5,7-diallyl-3,4-dihydro-6-hydroxy-1-prenyl-2(1H)-quinolinone.

Colorless flake crystals (recrystallized from ethyl acetate-n-hexane). Melting point: 133°–135° C.

Example 28

10 Grams of 6-allyl-7-allyloxy-3,4-dihydro-1-prenyl-2(1H)-quinolinone obtained in Example 20 was dissolved in 50 ml of tetralin and stirred at 200° to 230° C. for 3 hours. After cooling, the reaction mixture was subjected to purification by passing through a silica gel column, there was obtained 7.8 g (78%) of 6,8-diallyl-3,4-dihydro-7-hydroxy-1-prenyl-2(1H)-quinolinone.

Colorless flake crystals (recrystallized from ethyl acetate-n-hexane). Melting point 94°–96° C.

Example 29

2.4 Grams of the mixture of 6-allyl-7-allyloxy-3,4-dihydro-2(1H)-quinolinone and 6-allyl-7-allyloxy-3,4-dihydro-2(1H)-quinolinone as the reaction intermediate obtained in Example 14 was dissolved in 20 ml of dimethylformamide, then 0.6 g of 60% oily sodium hydride and 2.5 g of cinnamyl bromide were added thereto at room temperature and reacted similarly as in Reference example 7, there was obtained yellow oily product by treating thus obtained reaction mixture. Said oily product was dissolved in 50 ml of tetralin and stirred at 200° to 230° C. for 3 hours. After cooling, the reaction mixture was subjected to purification by passing through a silica gel column, there was obtained 1.2 g (33.4%) of 6,8-diallyl-1-cinnamyl-3,4-dihydro-7-hydroxy-2(1H)-quinolinone. Pale yellow flake crystals (recrystallized from isopropyl ether). Melting point: 132°–138° C.

Example 30

1.34 Grams of 5-allyl-6-hydroxy-1-prenyl-2(1H)-quinolinone obtained as shown in Example 3 was dissolved in 100 ml of dimethylformamide, then 0.5 g of potassium carbonate and 1 ml of allyl bromide were added thereto and stirred at room temperature over-night. After the dimethylformamide was removed by distillation under reduced pressure, the reaction mixture was extracted with methylene chloride. The extract was washed with water, dried with anhydrous magnesium sulfate, then solvent was removed by distillation under reduced pressure, thus obtained residue was dissolved in 10 ml of tetralin and stirred at 200° to 230° C. for 6 hours. After cooling, the reaction mixture was subjected to purification by passing through a silica gel column, there was obtained 0.5 g (34.3%) of 5,7-diallyl-6-hydroxy-1-prenyl-2(1H)-quinolinone.

Example 31

5-Allyloxy-3,4-dihydro-1-phenyl-2(1H)-quinolinone was treated similarly as in Example 1, there was obtained 6-allyl-3,4-dihydro-5-hydroxy-1-phenyl-2(1H)-quinolinone.

Colorless needle-like crystals (recrystallized from ethyl acetate-n-hexane). Melting point: 177°–178.5° C.

Example 32

1.2 Grams of 6-allyloxy-3,4-dihydro-1-(4-methoxyphenyl)-2(1H)-quinolinone was dissolved in 10 ml of tetralin and reacted similarly as in Example 1, the reaction mixture was treated, there was obtained 0.9 g of mixture of 5-allyl-3,4-dihydro-6-hydroxy-1-(4-methoxyphenyl)-2(1H)-quinolinone and 7-allyl-3,4-dihydro-6-hydroxy-1-(4-methoxyphenyl)-2(1H)-quinolinone. 0.9 Grams of this mixture was dissolved in 20 ml of dimethylformamide, then 1 g of potassium carbonate and 1 ml of allyl bromide were added thereto and stirred at room temperature overnight. The reaction mixture was extracted with 100 ml of ethyl acetate, the extract was washed with water and dried with anhydrous magnesium sulfate. After removal of the ethyl acetate by distillation under reduced pressure, 10 ml of tetralin was added and the whole mixture was stirred at 200° C. for 6 hours. After cooling, the reaction mixture was subjected to purification by passing through a silica gel column, there was obtained 0.5 g (37%) of 5,7-diallyl-3,4-dihydro-6-hydroxy-1-(4-methoxyphenyl)-2(1H)-quinolinone.

Colorless needle-like crystals (recrystallized from n-hexane). Melting point: 153.5°–154.5° C.

Example 33

4.8 Grams of the mixture obtained in Example 16 was dissolved in 100 ml of dimethylformamide, to this solution, 4 g of 10-tetrahydropyranyloxy-1-bromodecane, (which was prepared by reacting at room temperature 2.2 g of 60% oily sodium hydride, 10-bromodecanol and dihydropyran in the presence of a small amount of concentrated hydrochloric acid) was added and reacted similarly as in Reference example 7, thus obtained reaction mixture was treated to obtain 4.2 g of mixture of 5-allyl-6-allyloxy-3,4-dihydro-1-(10-tetrahydropyranyloxy)decyl-2(1H)-quinolinone and 7-allyl-6-allyloxy-3,4-dihydro-1-(10-tetrahydropyranyloxy)decyl-2(1H)-quinolinone as in the form of oily product. Without being isolated and purified, this mixture was dissolved in 20 ml of decalin, and was subjected to Claisen rearrangement similarly as in Example 29. After cooling, to this reaction mixture was added 1 ml of hydrochloric acid and 100 ml of water-containing ethanol, then stirred at room temperature for 12 hours. The ethanol was removed by distillation under reduced pressure, thus obtained residue was subjected to isolation and purification by means of a silica gel flush column chromatography by using a mixed solvent of ethyl acetate:n-hexane (1:10 to 1:2) as the eluent, there was obtained 1.7 g (32.2%) of 5,7-diallyl-3,4-dihydro-6-hydroxy-1-(10-hydroxy)-decyl-2(1H)-quinolinone.

Pale yellow oily product.
$^1$H-NMR (CDCl$_3$, ppm):
1.29 (12H, br), 1.45–1.66 (5H, m), 2.52–2.58 (2H, m), 2.76–2.82 (2H, m), 3.43 (4H, t), 3.60–3.67 (2H, m), 3.88 (2H, t), 4.93–5.23 (5H, m), 5.89–6.06 (2H, m), 6.68 (1H, s).

Example 34

1.5 Grams of 7-allyloxy-3(2H)-1,4-benzoxazinone obtained in Reference example 5 was dissolved in 10 ml of tetralin then reacted and treated similarly as in Example 1, there is obtained 1.1 g of mixture of 6-allyl-7-hydroxy-2(1H)-benzoxazinone and 8-allyl-7-hydroxy-2(1H)-benzoxazinone. 1.1 Grams of this mixture was dissolved in 20 ml of dimethylformamide, then 1 g of potassium carbonate and 1 ml of allyl bromide were added thereto and stirred at room temperature overnight. The reaction mixture was extracted with 100 ml of ethyl acetate, after washed with water, the extract was dried with anhydrous magnesium sulfate. After removal of the ethyl acetate by distillation under reduced pressure, 20 ml of tetralin was added and stirred at 180° C. for 6 hours. After cooling, the reaction mixture was subjected to purification by passing through a silica gel column, there was obtained 0.2 g (11%) of 6,8-diallyl-7-hydroxy-3(2H)-1,4-benzoxazinone.

Pale brown powdery crystals (recrystallized from isopropylether-n-hexane). Melting point: 94°–95° C.

Example 35

1.5 Grams of 6-allyloxy-3(2H)-1,4-benzoxazinone obtained in Reference example 6, was reacted and treated similarly as in Example 34, there was obtained 0.4 g (22%) of 5,7-diallyl-6-hydroxy-3-(2H)-1,4-benzoxazinone.

White powdery crystals (recrystallized from ethyl acetate-n-hexane). Melting point: 114°–115° C.

Example 36

0.8 Gram of 4-allyl-7-allyloxy-3(2H)-1,4-benzoxazinone obtained in Reference example 21, was reacted and treated similarly as in Example 34, there was obtained 0.4 g (35%) of 7-hydroxy-4,6,8-triallyl-3(2H)-1,4-benzoxazinone.

White powdery crystals (recrystallized from isopropyl ether). Melting point: 91°–92° C.

Example 37

1.9 Grams of 4-allyl-6-allyloxy-3(2H)-1,4-benzoxazinone obtained in Reference example 22, was reacted and treated similarly as in Example 34, there was obtained 0.9 g (18%) of 6-hydroxy-4,5,7-triallyl-3(2H)-1,4-benzoxazinone.

White powdery crystals (recrystallized from isopropyl ether-n-hexane). Melting point: 71°–73° C.

Example 38

1.9 Grams of 3-allyl-5-allyloxybenzoxazolinone obtained in Reference example 23 was dissolved in 10 ml of tetralin, and reacted and treated similarly as in Example 34, there was obtained 1.5 g (61%) of 5-hydroxy-3,4,6-triallylbenzoxazolinone.

Brown oily product
$^1$H-NMR (CDCl$_3$, ppm):
3.42 (2H, d), 3.54 (2H, d), 4.48–4.54 (2H, m), 4.94–5.30 (6H, m), 5.05 (1H, s), 5.89–6.11 (3H, m), 6.92 (1H, s).

Example 39

3.34 Grams of 6-hydroxybenzothiazolinone was dissolved in 50 ml of dimethylformamide, then 3.5 g of potassium carbonate was added thereto and stirred at 70° C. for 30 minutes. After cooling, to the reaction mixture was added 3 ml of allyl bromide and stirred for 5 hours, then the dimethylformamide was removed by distillation under reduced pressure. To thus obtained residue was added water and extracted with chloroform, the extract was washed with water, dried and concentrated to obtain an oily product. This oily product was used as the starting material, was reacted and treated similarly as in Example 34, there was obtained 0.4 g (23%) of 6-hydroxy-3,5,7-triallylbenzothiazolinone.

Colorless flake crystals (recrystallized from methylene chloride-n-hexane). Melting point: 110°–111° C.

Similar to the procedures as in Examples 25 to 32, the compounds of Examples 40–50 as shown in Table 1 and of Examples 51–60 as shown in Table 2 were prepared from the corresponding staring materials. Further, similar to the procedures as in Example 33, the compounds of Examples 61–66 as shown in Table 3 were prepared from the corresponding starting materials.

TABLE 1

| Example No. | $R^1$ | Recrystallization solvent | Crystal form | Melting point (°C.) |
|---|---|---|---|---|
| 40 | Methyl | Methylene chloride-n-hexane | Colorless needle | 120–122 |
| 41 | Isobutyl | Ethyl acetate-n-hexane | Colorless flake | 133–134 |
| 42 | 3-Chloropropyl | Ethyl acetate-n-hexane | White powder | 122–123 |
| 43 | 4-Bromobutyl | Ethyl acetate-n-hexane | Colorless needle | 128–130 |
| 44 | Cyclohexylmethyl | Ethyl acetate-n-hexane | Colorless needle | 141–142 |
| 45 | 2-Cyclohexenyl | Ethyl acetate-n-hexane | Colorless needle | 149–150 |
| 46 | Allyl | Ethyl acetate-n-hexane | Colorless needle | 101–103 |
| 47 | 2-Propynyl | Ethyl acetate-n-hexane | Colorless flake | 129–131 |
| 48 | Geranyl | n-hexane | Colorless needle | 78–80 |
| 49 | Cinnamyl | Ethyl acetate-n-hexane | Colorless needle | 157–159 |
| 50 | 3-Allyloxybenzyl | Ethyl acetate-n-hexane | White powder | 113–114 |

TABLE 2

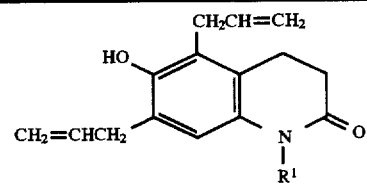

| Example No. | $R^1$ | Recrystallization solvent | Crystal form | Melting point (°C.) |
|---|---|---|---|---|
| 51 | 4-allyloxybenzyl | Ethyl acetate-n-hexane | Colorless needle | 108–113 |
| 52 | 4-Methoxybenzyl | Ethanol | Colorless flake | 163–164 |
| 53 | 3-Allyl-4-hydroxybenzyl | Ethyl acetate-n-hexane | White powder | 121–122 |
| 54 | 3,4-Dimethylbenzyl | Ethyl acetate-n-hexane | Colorless needle | 126–128 |
| 55 | Naphthylmethyl | Ethyl acetate-n-hexane | Colorless needle | 157–158 |
| 56 | 3-(Phthalimido-2-yl)propyl | Ethyl acetate-n-hexane | White powder | 127–129 |
| 57 | Ethoxycarbonylmethyl | Ethyl acetate-n-hexane | White powder | 103–104 |
| 58 | Phenyl | Ethyl acetate-n-hexane | Colorless needle | 182–184 |
| 59 | 4-Fluorophenyl | Ethyl acetate-n-hexane | Colorless plate | 188–190 |
| 60 | 3,4-Dimethoxyphenyl | n-Hexane | Pale yellow powder | 134–137 |

TABLE 3

| Example No. | $R^2$ | $R^3$ | Recrystallization solvent | Crystal form | Melting point (°C.) |
|---|---|---|---|---|---|
| 61 | 5-Hydroxy | 6-Allyl | Ethyl acetate-petroleum ether | White powder | 63–64 |
| 62 | 6-Hydroxy | 7-Allyl | Ethyl acetate-n-hexane | Colorless needle | 77–78 |
| 63 | 6-Hydroxy | 5-Allyl | Ethyl acetate-n-hexane | White powder | 84–86 |
| 64 | 7-Hydroxy | 6-Allyl | Ethyl acetate-n-hexane | White powder | 124–126 |
| 65 | 8-Hydroxy | 7-Allyl | Ethyl acetate-n-hexane | White powder | 65–66 |

TABLE 3-continued

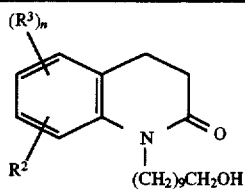

| Example No. | $R^2$ | $R^3$ | Recrystal- lization solvent | Crystal form | Melting point (°C.) |
|---|---|---|---|---|---|
| 66 | 7-Hydroxy | 6,8-Diallyl | Isopropyl ether- n-hexane | White powder | 89–91 |

Example 67

2.4 Grams of 5,7-diallyl-3,4-dihydro-6-hydroxy-1-[3-(phthalimido-2-yl)propyl]-2(1H)-quinolinone obtained in Example 56 and 1 ml of hydrazine monohydrate were dissolved in 50 ml of ethanol, this reaction mixture was stirred at 80° C. for 4 hours. The reaction mixture was cooled, then crystals being precipitated were separated by filtration, and the filtrate was concentrated, thus obtained residual product was extracted with 200 ml of ethyl acetate. The extract was washed with water, dried with anhydrous magnesium sulfate and concentrated to obtain residue. This residue was acidified by adding ethanol-hydrochloric acid and concentrated to dryness under reduced pressure, there was obtained 1 g (53.3%) of 1-(3-aminopropyl)-5,7-diallyl-3,4-dihydro-6-hydroxy-2(1H)-quinolinone hydrochloride.

White powdery crystals (recrystallized from acetone). Melting point: 182°–184° C.

Example 68

1.68 Grams of 1-(3-aminopropyl)-5,7-diallyl-3,4-dihydro-6-hydroxy-2(1H)-quinolinone was dissolved in 100 ml of water, then 10 ml of an aqueous solution containing 1 g of potassium cyanate was added thereto under ice-cooling condition, and stirred at room temperature for 12 hours. The crystals thus precipitated were collected by filtration and washed with water, there was obtained 0.5 g (29%) of 5,7-diallyl-3,4-dihydro-6-hydroxy-1-(3-ureidopropyl)-2(1H)-quinolinone.

White powdery crystals (recrystallized from ethanol). Melting point 203°–204° C.

Example 69

1.68 Grams of 1-(3-aminopropyl)-5,7-diallyl-3,4-dihydro-6-hydroxy-2(1H)-quinolinone was suspended in 100 ml of chloroform, then 5 ml of triethylamine was added thereto and stirred for 30 minutes. Under ice-cooling condition, 2 ml of chloroacetyl chloride was added little by little and stirred for 5 hours. The reaction mixture was washed with water, an aqueous solution saturated with sodium hydrogen carbonate and an aqueous solution saturated with sodium chloride, and dried with anhydrous magnesium sulfate, then concentrated under reduced pressure, there was obtained 1 g (53%) of 1-(3-chloroacetylaminopropyl)-5,7-diallyl-3,4-dihydro-6-hydroxy-2(1H)-quinolinone. White powdery crystals (recrystallized from ethyl acetate-n-hexane). Melting point: 152°–154° C.

In place of chloroacetyl chloride used in Example 69, 2.4 g of p-toluenesulfonyl chloride was used, there was prepared compound of Example 70 as follows.

Example 70

5,7-Diallyl-3,4-dihydro-6-hydroxy-1-[3-(p-toluenesulfonylamino)propyl]-2(1H)-quinolinone. White powdery crystals (recrystallized from diethyl ether). Melting point: 120°–121° C.

Example 71

1.6 Grams of 1-(3-chloropropyl)-5,7-diallyl-3,4-dihydro-6-hydroxy-2(1H)-quinolinone obtained in Example 42 was dissolved in 100 ml of acetonitrile, then 2 g of sodium iodide was added thereto, stirred at 80° C. for 30 minutes and cooled. To this reaction mixture was added 2 ml of triethylamine and 2 g of piperidine and was further stirred at 80° C. for 4 hours, then the reaction mixture was concentrated under reduced pressure, extracted with ethyl acetate. The extract was washed with water, dried and concentrated. Thus obtained oily product was subjected to purication by passing it through a silica gel column chromatography by using methylene chloride-methanol (50:1) as the eluent, there was obtained 0.96 g (52%) of 5,7-diallyl-3,4-dihydro-6-hydroxy-1-[3-(piperidinopropyl)]-2(1H)-quinolinone.

Colorless granular crystals (recrystallized from ethyl acetate-n-hexane). Melting point: 129°–130° C.

By using suitable starting materials and by using procedures similarly as in Example 71, there were prepared the compounds of Examples 72–75 as shown in Table 4.

TABLE 4

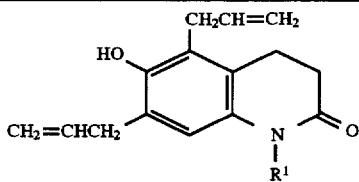

| Example No. | $R^1$ | Recrystal- lization solvent | Crystal form | Melting point (°C.) |
|---|---|---|---|---|
| 72 | 3-Morpholino- propyl | Ethyl acetate | Colorless needle | 141–142 |
| 73 | 3-(1- Piperazinyl)- propyl | Ethanol | Colorless granular | 201–203 |
| 74 | 3-(2-Methoxy- ethylamino)- propyl | Ethyl acetate- n-hexane | Colorless needle | 96–97 |
| 75 | 4-(4- Carbamoyl- piperidino)- butyl | Ethyl acetate- n-hexane | White powder | 147–149 |

Example 76

2 Grams of 5,7-diallyl-3,4-dihydro-1-(ethoxycarbonylmethyl)-6-hydroxy-2(1H)-quinolinone obtained in Example 57 was dissolved in 100 ml of 1N-sodium hydroxide aqueous solution, and the solution was stirred at 60° C. for 4 hours. Under ice-cooling condition, the reaction mixture was acidified with hydrochloric acid, the crystals thus precipitated were collected by filtration, washed with water and dried. There was obtained 0.8 g (53%) of 1-(carboxymethyl)-5,7-diallyl-3,4-dihydro-6-hydroxy-2(1H)-quinolinone.

White powdery crystals (recrystallized from ethanol).
Melting point: 187°–190° C.

Example 77

1.65 Grams of 5,7-diallyl-1-(ethoxy-carbonylmethyl)-3,4-dihydro-6-hydroxy-2(1H)-quinolinone obtained in Example 57 was dissolved in 50 ml of methanol, then 20 ml of 25% ammonia water thereto, the reaction mixture was stirred for 24 hours. Then the reaction mixture was concentrated under reduced pressure. The concentrate was extracted with chloroform, washed with water, dried, then concentrated again under reduced pressure. Thus obtained crude crystals were subjected to purification by passing it through a silica gel column and by using methylene chloridemethanol (50:1) as the eluent, there was obtained 1.2 g (80%) of 1-(carbamoylmethyl)-5,7-diallyl-3,4-dihydro-6-hydroxy-2(1H)-quinolinone.

White powdery crystals (recrystallized from ethanol).
Melting point: 163°–164° C.

Example 78

3.4 Grams of 6-allyloxy-1-(4-allyloxy-3-methoxybenzyl)-3,4-dihydro-2(1H)-quinolinone obtained in Reference example 13 was reacted and treated similarly as in Example 1, the reaction mixture thus obtained was subjected to flush column chromatography by using ethyl acetate:n-hexane (1:100 to 1:25). The secondary eluted portion was collected and concentrated under reduced pressure. The concentrate was recrystallized from ethyl acetate-n-hexane, there was obtained 0.6 g (17.6%) of 5-allyl-6-hydroxy-1-(3-allyl-4-hydroxy-5-methoxybenzyl)-3,4-dihydro-2(1H)-quinolinone. White crystalline powder (recrystallized from ethyl acetate-n-hexane). Melting point: 159°–161° C.

Example 79

2.43 Grams of the mixture of 5-allyl-6-allyloxy-3,4-dihydro-2(1H)-quinolinone and 7-allyl-6-allyloxy-3,4-dihydro-2(1H)-quinolinone obtained in Example 16 was dissolved in 50 ml of dimethylformamide, then 0.6 g of 60% oily sodium hydride was added little by little thereto at room temperature, and stirred at 25° to 40° C. until generation of hydrogen gas was ceased. After the reaction mixture was cooled to room temperature, 1.32 g of 1,4-dibromomethylbenzene was added and stirred at room temperature for 4 hours. After the reaction was finished, water was added thereto, extracted with ethyl acetate, the extract was washed with water, and aqueous solution saturated with sodium chloride, then dried with anhydrous magnesium sulfate. The magnesium sulfate was removed by filtration, the filtrate was concentrated to obtain 5.9 g (100%) of pale yellow oily product. 3 Grams of this yellow oily product was dissolved in 50 ml of tetralin, and was reacted and treated similarly as in Example 1, there was obtained 3 g (100%) of 1,4-bis[(5,7-diallyl-6-hydroxy-2-oxo-1,2,3,4-tetrahydroquinolyl)methyl]-benzene.

Pale yellow powder (recrystallized from ethanol).
Melting point: 213°–215° C.

Example 80

80 Grams of the mixture of 5-allyl-6-allyloxy-3,4-dihydro-2(1H)-quinolinone and 7-allyl-6-allyloxy-3,4-dihydro-2(1H)-quinolinone obtained in Example 16 was dissolved in 300 ml of dimethylformamide, then 15 g of 60% oily sodium hydride was added little by little thereto at room temperature and stirred at 25° to 40° C. until generation of hydrogen gas was ceased. After the reaction mixture was cooled to room temperature, 35 g of prenyl chloride was added thereto and stirred at 50° C. for 2 hours, further stirred at room temperature for 8 hours. After finished the reaction, the dimethylformamide was removed by distillation under reduced pressure to obtain the residue. To the residue was added water and extracted with ethyl acetate. The extract was washed with water and an aqueous solution saturated with sodium chloride, then dried with anhydrous magnesium sulfate. The magnesium sulfate was removed by filtration, and the filtrate was concentrated to obtain pale yellow oily product. This oily product was subjected to separation and purification by means of a silica gel flush chromatography, by using a mixed solvent of ethyl acetate:n-hexane (1:10 to 1:2) as the eluent, there was obtained 29 g (28.3%) of 6-allyloxy-3,4-dihydro-1-prenyl-7-(1-propenyl)-2(1H)-quinolinone.

Colorless needle-like crystals (recrystallized from ethyl acetate-n-hexane). Melting point: 87°–88° C.

$^1$H-NMR (CDCl$_3$, ppm):

1.73 (1H, s), 1.83 (1H, s), 1.90 (3H, d), 2.63 (2H, m), 2.84 (2H, t), 4.52–4.55 (4H, m), 5.12–5.17 (2H, m), 5.27–5.47 (2H, m), 6.01–6.21 (2H, m), 6.66 (1H, s), 6.72 (1H, d), 7.01 (1H, s).

Example 81

5-Allyloxy-1-{3-[4-(3-chlorophenyl)-1-piperazinyl]propyl}-3,4-dihydro-2(1H)-quinolinone was reacted and treated similarly as in Example 1. Thus obtained crude product was subjected to purification by means of a silica gel chromatography, thus obtained product was dissolved in ethanol and acidified with hydrochloric acid, concentrated under reduced pressure to dryness, there was obtained 6-allyl-5-hydroxy-1-{3-[4-(3-chlorophenyl)-1-piperazinyl]propyl}-3,4-dihydro-2(1H)-quinolinone.hydrochloride.

Colorless needle crystals (recrystallized from ethanolisopropyl ether). Melting point: 200°–204° C.

Example 82

1-(3-Chlorophenyl)piperazine was used as cyclic amine and was reacted and treated similarly as in Example 71. Thus obtained crude product was subjected to purification by means of a silica gel chromatography, there is obtained 5,7-diallyl-1-{3-[4-(3-chlorophenyl)-1-piperazinyl]propyl}-3,4-dihydro-6-hydroxy-2(1H)-quinolinone.

Colorless needle-like crystals (recrystallized from ethyl acetate-n-hexane). Melting point: 117.5°–118.5° C.

Example 83

8-Allyl-7-hydroxy-3-prenyl-2(1H)-quinolinone obtained in Example 4 was reacted and treated similarly as in Example 39, there was obtained 6,8-diallyl-7-hydroxy-3-prenyl-2(1H)-quinolinone.

Pale yellow needle-like crystals (recrystallized from acetone). Melting point: 241°–244° C.

Example 84

1-(4-Bromobutyl)-5,7-diallyl-3,4-dihydro-6-hydroxy-2(1H)-quinolinone (1.9 g) prepared in Example 43 was dissolved in acetonitrile (50 ml), then n-butylamine (2 ml) was added and stirred at 80° C. for 4 hours. The reaction mixture was extracted with ethyl acetate, and the extract was washed with an aqueous solution saturated with sodium bicarbonate, next with water, then concentrated under reduced pressure. Thus obtained oily residual product was dissolved in ethanol, acidified by adding oxalic acid, then concentrated to dryness, and recrystallized from acetone, there was obtained of 1-(4-n-butylaminobutyl)-5,7-diallyl-3,4-dihydro-6-hydroxy-2(1H)-quinolinone.oxalate in 35% yield.

White powdery product (recrystallized from acetone).

Melting point: 194°–197° C. (decomposed).

By reacting 1-(4-bromobutyl)-5,7-diallyl-3,4-dihydro-6-hydroxy-2(1H)-quinolinone with suitable amines or cyclic amines similarly as in Example 84, there were obtained compounds of Examples 85 to 87 as follows.

Example 85

5,7-Diallyl-3,4-dihydro-6-hydroxy-1-[4-(2-hydroxy-1,1-dimethyl)ethylamino]butyl-2-(1H)-quinolinone. oxalate.

White powdery crystals (recrystallized from acetone).

Melting point: 129°–132° C.

Example 86

5,7-Diallyl-1-(4-diethylaminobutyl)-3,4-dihydro-6-hydroxy-2(1H)-quinolinone.oxalate White powdery crystals (recrystallized from acetone).

Melting point: 191°–193° C.

Example 87

5,7-Diallyl-3,4-dihydro-6-hydroxy-1-[4-(imidazol-1-yl) butyl ]-2-(1N)-quinolinone.oxalate White powdery crystals (recrystallized from acetone).

Melting point: 125°–128° C.

Example 88

1-(3-Chloropropyl)-5,7-diallyl-3,4-dihydro-6-hydroxy-2(1H)-quinolinone and 1H-1,2,4-triazole were reacted and treated similarly as in Example 71, there was obtained 5,7-diallyl-3,4-dihydro-6-hydroxy-1-[3-(1,2,4-triazol-4-yl)propyl]-2(1H)-quinolinone.

White powdery crystals (recrystallized from acetone).

Melting point: 129°–132° C.

By reacting a quinolinone compound having a haloalkyl group at 1-position with an ester of amino acid, there were prepared compounds of Examples 89 to 90 as follows.

Example 89

1-(4-Bromobutyl)-5,7-diallyl-3,4-dihydro-6-hydroxy-2(1H)-quinolinone (1.9 g) was dissolved in 50 ml of acetonitrile, then 2 g of L-leucine methyl ester hydrochloride and 5 ml of triethylamine were added thereto, and stirred at 80° C. for 4 hours. The reaction mixture was extracted with ethyl acetate, the extract was washed with an aqueous solution saturated with sodium bicarbonate, next with water, then was concentrated under reduced pressure. Thus obtained oily residual product was subjected to purification by means of a silica gel column chromatography, then recrystallized from acetone, there was obtained 1-[4-(1-methoxycarbonyl-4-methyl)pentylamino]butyl-5,7-diallyl-3,4-dihydro-6-hydroxy-2(1H)-quinolinone.hydrochloride.

White powdery crystals (recrystallized from acetate).

Melting point: 184°–186° C.

Example 90

5,7-Diallyl-3,4-dihydro-1-[4-(1-methoxy-carbonyl-4-methyl)pentylamino]butyl-6-hydroxy-2(1H)-quinolinone (1 g) obtained in Example 89 was dissolved in 10 ml of methanol and 10 ml of 1N-sodium hydroxide aqueous solution, then this mixture was stirred at 70° C. for 1 hour. After cooling, the reaction mixture was acidified by adding hydrochloric acid, further the acidified reaction mixture was made basic by adding 25% ammonia water. The reaction mixture was concentrated under reduced pressure to dryness, thus obtained solid residual product was subjected to extraction by means of a Soxhlet's extractor with chloroform as the solvent. The chloroform extract was concentrated under reduced pressure to dryness, then recrystallized from acetone, there was obtained 1-[4-(1-carboxy-4-methyl)pentylamino]butyl-5,7-diallyl-3,4-dihydro-6-hydroxy-2(1H)-quinolinone.

White powdery crystals (recrystallized from acetone).

Melting point: 166°–174° C. (decomposed).

Example 91

1-(4-Bromobutyl)-5,7-diallyl-3,4-dihydro-6-hydroxy-2(1H)-quinolinone (1.9 g) was dissolved in 50 ml of acetonitrile, then 2 g of N-methylglycine ethyl ester hydrochloride and 5 ml of triethylamine were added thereto, and stirred at 80° C. for 4 hours. The reaction mixture was extracted with ethyl acetate, the extract was washed with an aqueous solution saturated with sodium bicarbonate, next with water, then concentrated under reduced pressure. Thus obtained oily residual product was subjected to purification by means of a silica gel column chromatography, then dissolved in 10 ml of methanol and 10 ml of 1N-sodium hydroxide aqueous solution, and stirred at 70° C. for 1 hour. After the reaction mixture was cooled, the mixture was acidified by adding hydrochloric acid, further the acidified reaction mixture was made basic by adding 25% ammonia water. This reaction mixture was concentrated under reduced pressure to dryness, thus obtained solid residual product was subjected to extraction by means of Soxhlet's extractor with chloroform as the solvent. The chloroform extract was concentrated under reduced pressure to dryness, and recrystallized from acetone, there was obtained 1-[4-(N-carboxymethyl-N-methyl-amino)butyl ]-5,7-diallyl-3,4-dihydro-6-hydroxy-2(1H)-quinolinone.

White powdery crystals (recrystallized from acetone).

Melting point: 174°–181° C. (decomposed).

Example 92

1-(4-Bromobutyl)-5,7-diallyl-3,4-dihydro-6-hydroxy-2(1H)-quinolinone (1.9 g) was dissolved in 50 ml of acetonitrile, then 2 g of L-proline methyl ester hydrochloride and 5 ml of triethylamine were added thereto, and stirred at 80° C. for 4 hours. The reaction mixture was extracted with ethylacetate, the extract was washed with an aqueous solution saturated with sodium bicarbonate, next with water, then concentrated under reduced pressure. The obtained oily residual product was subjected to purification by means of a silica gel column chromatography, then dissolved in 10 ml of methanol and 10 ml of 1N-sodium hydroxide aqueous solution, and stirred at 70° C. for 1 hour. After the reaction mixture was cooled, the mixture was acidified by adding hydrochloric acid, further the acidified reaction mixture was made basic by adding 25% ammonia water. This reaction mixture was concentrated under reduced pressure to dryness, thus obtained solid residual product was subjected to extraction by means of Soxhlet's extractor with chloroform as the solvent. The chloroform extract was concentrated under reduced pressure to dryness, and recrystallized from acetone, there was obtained 1-[4-(2-carboxy-1- pyrrodinyl)butyl ]-5,7-diallyl-3,4-dihydro-6-hydroxy-2(1H)-quinolinone.

White powdery crystals (recrystallized from acetone).

Melting point: 147°–151° C.

Example 93

Mixture of 1-(4-bromobutyl)-5,7-diallyl-3,4-dihydro-6-hydroxy-2(1H)-quinolinone (1.5 g), triethylphosphite (3 ml) and sodium iodide (100 mg) was stirred at 150° C. for 4 hours. After the reaction mixture was cooled, the reaction mixture was subjected to purification by passing it through a silica gel column chromatography by using ethyl acetate-n-hexane as the eluent, then recrystallized from water-containing ethanol, there was obtained 5,7-diallyl-1-(4-diethoxy-phosphorylbutyl)-3,4-dihydro-6-hydroxy-2(1H)-quinolinone in 64% yield.

White powdery product (recrystallized from water-containing ethanol).

Melting point: 38°–42° C.

Example 94

5,7-Diallyl-3,4-dihydro-6-hydroxy-2(1H)-quinolinone (24.3 g) obtained in Example 26 was dissolved in 100 ml of 3,4-dihydro-2H-pyran, then 1 ml of concentrated hydrochloric acid was added thereto and stirred at 60° C. for 8 hours. The reaction mixture was cooled, and neutralized with 10% sodium bicarbonate solution, then extracted with ethyl acetate. The extract was washed with an aqueous solution saturated with sodium bicarbonate, and concentrated under reduced pressure. Recrystallized from ethyl acetate-n-hexane, there was obtained 14 g (58%) of 5,7-diallyl-3,4-dihydro-6-(2-tetrahydropyranyloxy)-2(1H)-quinolinone.

White crystalline powder (recrystallized from ethyl acetate-n-hexane).

Melting point: 119°–120° C.

Example 95

5,7-Diallyl-3,4-dihydro-6-(2-tetrahydropyranyloxy)-2 (1H)-quinolinone (6.47 g) obtained in Example 94 was dissolved in 100 ml of dimethylformamide, then 1.2 g of 60% oily sodium hydride was added little by little thereto at room temperature and stirred until generation of hydrogen gas was ceased. Then, 5 ml of 2-bromoethylcyanide was added thereto and stirred at room temperature for 4 hours. After finished the reaction, water was added to the reaction mixture and extracted with ethyl acetate. The extract was washed with water, and an aqueous solution saturated with sodium chloride in this order, then dried with anhydrous magnesium sulfate. The magnesium sulfate was removed by filtration, and the filtrate was concentrated to obtain pale yellow oily product. This oily product was subjected to purification by means of a silica gel column chromatography (by using methylene chloride-ethyl acetate=4:1 as the eluent).

Recrystallized from ethyl acetate-n-hexane there was obtained 1-(2-cyanoethyl)-5,7-diallyl-3,4-dihydro-6-(2-tetrahydropyranyloxy)-2(1H)-quinolinone.

Colorless needle crystals (recrystallized from ethyl acetate-n-hexane).

Melting point: 93°–94° C.

Example 96

1-(2-Cyanoethyl)-5,7-diallyl-3,4-dihydro-6-(2-tetrahydropyranyloxy)-2(1H)-quinolinone (1 g) obtained in Example 95 was dissolved in 50 ml of methanol, then 6N-hydrochloric acid was added thereto and stirred at 60° C. for 30 minutes so as to remove the tetrahydropyranyl group, and concentrated under reduced pressure to dryness. Thus obtained residual product was subjected to purification by means of a silica gel column chromatography, then recrystallized from ethyl acetate-n-hexane, there was obtained 1-(2-cyanoethyl)-5,7-diallyl-3,4-dihydro-6-hydroxy-2(1H)-quinolinone.

Colorless needle-like crystals (recrystallized from ethyl acetate-n-hexane).

Melting point: 114°–116° C.

Suitable halogenated compounds and 5,7-diallyl-3,4-dihydro-6-(2-tetrahydropyranyloxy)-2(1H)-quinolinone were reacted and treated similarly as in Examples 95 or 96, there were prepared compounds of Examples 97 to 108 as shown in Table 5 as follows.

TABLE 5

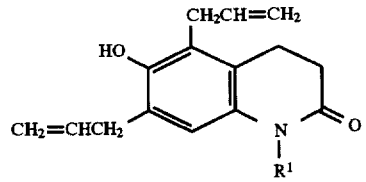

| Example No. | $R^1$ | Recrystallization solvent | Crystal form | Melting point (°C.) |
|---|---|---|---|---|
| 97 | 1-Ethyl- | Ethyl acetate-n-hexane | Colorless needles | 108–109 |
| 98 | 1-Isopropyl- | Ethyl acetate-n-hexane | Colorless needles | 149–150 |
| 99 | 1-n-Butyl- | Ethanol | Colorless plates | 116–117 |
| 100 | 1-(3-Methylbutyl)- | Ethyl acetate-n-hexane | Colorless plates | 119–120 |
| 101 | 1-Octyl- | Ethyl acetate-n-hexane | Colorless needles | 102–103 |
| 102 | 1-Dodecyl- | Ethyl acetate-n-hexane | Colorless flakes | 90–91 |
| 103 | 1-(2-Acetyloxyethyl)- | Ethyl acetate-n-hexane | Colorless flakes | 87–88 |
| 104 | 1-(4-Acetyloxybutyl)- | Ethyl acetate-n-hexane | Colorless flakes | 107–108 |
| 105 | 1-(4-Methoxycarbonylbutyl)- | Ethyl acetate-n-hexane | Colorless flakes | 84–86 |
| 106 | 1-(5-Ethoxycarbonylpentyl)- | Ethyl acetate-n-hexane | Colorless flakes | 79–80 |
| 107 | 1-(4-Methoxycarbonylbenzyl)- | Ethyl acetate- | White powder | 155–157 |
| 108 | 1-(2-Ethoxycarbonylethyl)- | Diethyl ether-n-hexane | White powder | 127–129 |

Example 109

1-(2-Acetyloxyethyl)-5,7-diallyl-3,4-dihydro-6-hydroxy-2(1H)-quinolinone (1 g) prepared in Example 103 was hydrolyzed similarly as in Example 76, there was obtained 5,7-diallyl-3,4-dihydro-6-hydroxy-1-(2-hydroxyethyl)-2 (1H)-quinolinone.

White powdery crystals (recrystallized from ethyl acetate-n-hexane).

Melting point: 106°–108° C.

Example 110

1-(2-Acetyloxybutyl)-5,7-diallyl-3,4-dihydro-6-hydroxy-2(1H)-quinolinone (1 g) prepared in Example 104 was hydrolyzed similarly as in Example 109, there was obtained 5,7-diallyl-3,4-dihydro-6-hydroxy-1-(2-hydroxybutyl)-2(1H)-quinolinone.

Colorless granular crystals (recrystallized from ethylacetate-n-haxane).

Melting point: 115°–116° C.

Example 111

5,7-Diallyl-3,4-dihydro-6-hydroxy-1-(4-methoxycarbonylbenzyl)-2(1H)-quinolinone (1 g) prepared in Example 107 was hydrolyzed similarly as in Example 109, there was obtained 1-(4-carboxybenzyl)-5,7-diallyl-3,4-dihydro-6-hydroxy-2(1H)-quinolinone. White powdery crystals (recrystallized from methanol).

Melting point: 242°–246° C.

Example 112

5,7-Diallyl-3,4-dihydro-6-hydroxy-1-(2-ethoxycarbonylethyl)-2(1H)-quinolinone (1 g) prepared in Example 108 was hydrolyzed similarly as in Example 109, there was obtained 1-(4-carboxyethyl)-5,7-diallyl-3,4-dihydro-6-hydroxy-2(1H)-quinolinone.

White powder crystals (recrystallized from ethyl acetate-n-hexane). Melting point: 174°–176° C.

Example 113

1-(4-Carboxymethyl)-5,7-diallyl-3,4-dihydro-6-hydroxy-2(1H)-quinolinone was dissolved in 50 ml of methanol, then under ice-cooling condition, an methanol solution of potassium hydroxide was added thereto so as to adjust pH=8 to 9, then concentrated to dryness. Recrystallized from methanol, there was obtained sodium (5,7-diallyl-6-hydroxy-1,2,3,4-tetrahydro-2-oxoquinolin-1-yl)acetate. Pale yellow powder crystals (recrystallized from methanol).

Melting point: 212°–221° C. (decomposed).

Similar to as in Example 113, there were prepared compounds of Examples 114 and 115 as follows.

Example 114

1-(4-Carboxybenzyl)-5,7-diallyl-3,4-dihydro-6-hydroxy-2(1H)-quinolinone was treated similarly as in Example 113, there was obtained sodium 4-(5,7-diallyl-6-hydroxy-1,2,3,4-tetrahydro-2-oxoquinolin-1-yl)-methylbenzoate.

Pale yellow powdery crystals (recrystallized from acetone).

Melting point: 268°–285° C. (decomposed).

Example 115

Sodium 2-(5,7-Diallyl-6-hydroxy-1,2,3,4-tetrahydro-2-oxoquinolin-1-yl)propionate.

Pale yellow powdery crystals (recrystallized from acetone).

Melting point: 201°–203° C. (decomposed).

Example 116

2-(4-Chlorobutyl)-1-cyclohexyl-1H-1,2,3,4-tetrazole was reacted with 5,7-diallyl-3,4-dihydro-6-(2-tetrahydropyranyloxy-2(1H)-quinolinone in accordance with methods of preparation similarly as in Examples 95 and 96, there was obtained 1-[4-(1-cyclohexyl-1H-1,2,3,4-tetrazol-2-yl)butyl-5,7-diallyl-3,4,-dihydro-2(1H)-quinolinone.

Pale yellow powdery crystals (recrystallized from ethanol).

Melting point: 121°–124° C.

5,7-Diallyl-3,4-dihydro-6-hydroxy-1-prenyl-2(1H)-quinolinone obtained in Example 27 was reacted with a suitable corresponding starting material, similarly as in Example 16, there were obtained compounds of Examples 117 to 120 as follows.

Example 117

6-Acetyloxy-5,7-diallyl-3,4-dihydro-1-prenyl-2(1H)-quinolinone.

Boiling point: 140°–150° C./0.4 mmHg

Example 118

6-(3-Carboxypropionyloxy)-5,7-diallyl-3,4-dihydro-1-prenyl-2(1H)-quinolinone.

White powder (recrystallized from acetone-water).

Melting point: 148°–151° C.

Example 119

5,7-Dialyl-3,4-dihydro-6-(3-nicotinoyloxy)-1-prenyl-2(1H)-quinolinone-hydrochloride.

Pale yellow powder crystals (recrystallized from acetone-water).

Melting point: 142°–151° C.

Example 120

Sodium 5,7-diallyl-3,4-dihydro-1-prenyl-2(1H)-quinolinone-6-oxide.

Reddish orange powder crystals (recrystallized from methanol)

Melting point: 110°–117° C. (decomposed).

Pharmacological tests

Pharmacological tests of the cyclic amide derivatives of the present invention relating to in vitro test for determination of the activity for inhibiting the formation of lipid peroxides by ultraviolet radiation, and the activity for scavenging radicals; and in vivo test for determination of the activity for photoprotection were conducted as follows:

(A) The activity for inhibiting the formation of lipid peroxides

The activity for inhibiting the formation of lipid peroxides which are increasingly formed by exposed to the ultraviolet-B radiation to the skin homogenate of guinea pig was determined by a procedure of thiobarbituric acid method (TBA method).

Unsaturated fatty acids of bioconstituents are oxidized finally to malondialdehyde by the actions of various radicals formed due to exposed to the ultraviolet rays. The activity for inhibiting the formation of lipid peroxides can be evaluated by degree of decreasing the optical absorbance of the condensate of thus formed malondialdehyde with thiobarbituric acid, by adding a test sample of the cyclic amide derivative of the present invention to the homogenate. In this test, vitamin E which was used as the reference compound, is known that it possesses antioxidation activity, activity for scavenging radicals and activity for inhibiting the formation of lipid peroxides.

The test was conducted by applying OGURA's method [cf. Kurume Igakukai Zasshi (Journal of Kurume Medical Academy (Japan)), 1984, Vol. 47, pp. 223–236]. That is, the hairs covering in the back of an albino guinea pig (Hartley strain, female) were clipped by using an electric hair clippers under anesthesia. After the enucleation of the hair clipped portion of the skin, the subcutaneous tissue of this skin was removed in cold physiological saline. Distilled water in an amount of 9 times by weight of the skin tissue was added to this skin subcutaneous tissue, then was subjected to homogenation and centrifugation (600 g, for 5 minutes) to obtain the supernatant liquid. 5 Microliters each of test sample solutions of various concentrations was added to 0.5 ml each of the supernatant liquid, then the ultraviolet ray in the intensity of 9.5 mW/cm$^2$ was irradiated for 60 minutes by using fluorescent lamps (TOSHIBA FL-20SE, manufactured by Toshiba Corporation) as a light source. As to the reference sample solution, the solvent for dissolution of the test compound was used in place of the test sample solution. After ultraviolet radiation, the amount of lipid peroxide being formed in the sample solution (TBA value) was measured by TBA method (cf. Analytical Biochemistry, 1979, Vol. 95, pp. 351–358), and the inhibition rate of lipid peroxide formation shown by the test sample was calculated by the following formula:

$$\text{Inhibition rate of lipid peroxide formation (\%)} = \left(1 - \frac{\text{TBA value of the test sample solution}}{\text{TBA value of the reference solution}}\right) \times 100$$

Test results of inhibition rate of lipid peroxide formation of the test compounds in the concentration of $10^{-4}$M are shown in Table 6. Vitamin E ($\alpha$-tocopherol) used as the reference compound in the same concentration ($10^{-4}$M) showed about 77–79% of the inhibition as shown by the test samples.

TABLE 6

| Example No. | Inhibition rate of lipid peroxide formation (%) | Example No. | Inhibition rate of lipid peroxide formation (%) |
| --- | --- | --- | --- |
| 10 | 82 | 51 | 95 |
| 11 | 70 | 52 | 100 |
| 17 | 85 | 53 | 95 |
| 20 | 81 | 54 | 96 |
| 25 | 78 | 57 | 78 |
| 26 | 80 | 60 | 83 |
| 27 | 82 | 62 | 81 |
| 28 | 80 | 63 | 81 |
| 32 | 87 | 65 | 79 |
| 33 | 83 | 67 | 75 |
| 38 | 80 | 68 | 68 |
| 39 | 82 | 69 | 78 |
| 40 | 84 | 74 | 68 |
| 41 | 96 | 76 | 68 |
| 44 | 100 | 78 | 95 |
| 45 | 95 | 80 | 95 |
| 46 | 95 | 86 | 71 |
| 48 | 95 | 93 | 73 |
| 50 | 89 | | |

As can be seen from the test results in Table 6, cyclic amide derivatives of the present invention inhibit the formation of thiobarbituric acid reaction products formed in the skin of guinea pig by the irradiation of ultraviolet rays. Thus, cyclic amide derivatives of the present invention inhibit the actions of active oxygen species and of lipid peroxides species which are formed increasingly by ultraviolet radiation. Therefore, cyclic amide derivatives of the present invention can be expected to the usefulness of agents for preventing and treating various diseases caused by active oxygen species formed increasingly by ultraviolet radiation, and preventive agents and cosmetics, quasi-drugs and medicines for external use for preventing sunburn, winkles and melasma caused by the sunlight.

(B) The activity for inhibiting skin erythema which is caused by ultraviolet radiation This test is an experimental model of quantitative evaluation method for measuring protective effect of the test compound relating to the skin erythema reaction (sunburn) caused by ultraviolet radiation (Cf. The Journal of Dermatology, Vol. 17, pp. 595–598, 1990).

The hairs covering in the back of albino guinea pig (Hartley strain, female, 7–8 week age) were shaved by using an electric hair clippers and a shaver. In the next day, the guinea pig was fixed in Bowlman's cage, then a light shield tape (adhesive plaster for patch test), having 4 round holes of 1.5 cm in diameter was adhered on the hair clipped portion so as to provide 4 sites (round holes) to be exposed to the ultraviolet rays. The solvent for dissolving the test compound of 10 µl was topically applied to a site (control site to be exposed), and 10 µl each of the test sample solutions in predetermined concentrations was topically applied to the remaining three sites (test sites to be exposed). 30 Minutes later the applications, the ultraviolet rays in the intensity of 1.3–1.5 mW/cm$^2$ was irradiated for 30 minutes by using fluorescent lamps (TOSHIBA FL-20SE) as the light source. 24 Hours later ultraviolet radiation, the degrees of flush ($\Delta a$ value) of the control site and the test sites applied with the test sample solutions were measured by using a color difference meter (OFC-300A type, manufacture by NIPPON DENSHOKU KOGYO CO., LTD.) and the rate of activity for inhibiting the skin erythema of the test compound was calculated by the following formula:

$$\text{Rate of activity for inhibiting the skin erythema (\%)} = \left(1 - \frac{\Delta a \text{ value of the test site}}{\Delta a \text{ value of the control site}}\right) \times 100$$

($\Delta a$ value: difference between $a$-values of irradiated skin and not irradiated skin)

Each one of the test sample solutions was prepared by dissolving each test compounds in three kinds of concentrations within 0.1 to 10%, and applied.

Rate of activity for inhibiting the skin erythema by the test sample solutions of 3% concentration of the test compound are shown in Table 7 as follows, and the figures in parentheses represent 50% inhibitory concentration (IC$_{50}$ value; concentration in %) of the test compound.

TABLE 7

| Example No. | Rate of activity for inhibiting the skin erythema (%) (IC$_{50}$; concentration in %) | Example No. | Rate of activity for inhibiting the skin erythema (%) (IC$_{50}$; concentration in %) |
| --- | --- | --- | --- |
| 10 | 38 | 67 | 31 |
| 20 | 37 | 68 | 43 |
| 26 | 36 | 71 | 45 |
| 27 | 60 (1.3) | 72 | 33 |
| 28 | 30 | 76 | 50 (3.1) |
| 33 | 18 (9.4) | 77 | 50 (2.7) |
| 35 | 41 (5.9) | 84 | 31 |

TABLE 7-continued

| Example No. | Rate of activity for inhibiting the skin erythema (%) (IC$_{50}$; concentration in %) | Example No. | Rate of activity for inhibiting the skin erythema (%) (IC$_{50}$; concentration in %) |
|---|---|---|---|
| 36 | 26 (9.8) | 85 | 39 |
| 37 | 39 (7.7) | 87 | 28 |
| 39 | 42 (4.7) | 88 | 37 |
| 40 | 23 (5.6) | 101 | 37 |
| 41 | 57 (2.0) | 102 | 57 (3.7) |
| 42 | 45 | 104 | 31 |
| 44 | 63 (1.6) | 105 | 44 |
| 48 | 37 | 107 | 44 |
| 50 | 36 | 110 | 44 |
| 60 | 27 | 113 | 52 (2.5) |
| 63 | 35 (6.5) | 115 | 33 |

As can be seen from the test results in Table 7, cyclic amide derivatives of the present invention inhibit the skin erythema reaction caused by ultraviolet radiation in guinea pig. Thus, cyclic amide derivatives of the present invention are useful as agent for protecting various disease including skin cancer caused by the ultraviolet rays, and also these derivatives are useful as agents for protecting sunburn, wrinkles and melasma caused by the sunlight, cosmetics, quasi-drugs and medicines for external use.

(C) The activity for preventing the lens opacity

The test was conducted by referring to a method of Abraham Spector (cf. Current Eye Research, Vol. 2, 1993, pp. 163–179).

The lens samples obtained from rat (Wistar strain, male, 6–10 week age) were placed on 24-well plate, and were cultured in DEMEM (Dulbecco's modified Eagle's medium manufactured by Nissui Pharmaceutical Co., Ltd.) at 37° C. overnight, a 5% $CO_2$ environment was used. Under dissecting microscope observation, the lens samples having transparency were only selected to use the test. Thus selected lens samples were transferred to midium (1 ml) in which the test compound was dissolved. (As to the reference test, the medium without containing the test compound was used.) The ultraviolet rays in the intensity of 8.8 mW/cm$^2$ was irradiated for 60 minutes by using a fluorescent lamp (TOSHIBA FL-20SE) to the lens samples. After the irradiation, the medium was replaced to new medium containing the test compound and further cultured overnight. The medium without the test compound was replaced everyday during 3 days. By using a dissecting microscope, opacity of the lens samples were observed. The degrees of opacity of the lens samples was determined by deviding the field of vision into 8 fields as follows: Score 0: transparent; Score 1: some loss of transparency; and Score 2: completely opaque. Rate of activity for preventing the lens opacity was calculated from the following formula:

$$\text{Rate of the activity for preventing the lens opacity (\%)} = \left(1 - \frac{\text{sum of the scores in 8 fields of vision shown by the test lens sample}}{\text{sum of the scores in 8 fields of vision shown by the reference lens sample}}\right) \times 100$$

Test results of rate of the activity for preventing the lens opacity given by test compounds in the concentration of 10$^{-4}$M are shown in Table 8. The cyclic amide derivatives or salts thereof of the present invention show about 10 times higher effect as compared with that of shown by vitamin C.

TABLE 8

| Example No. | Concentration of test compound (10$^{-4}$M) | Rate of the activity for preventing lens opacity (%) |
|---|---|---|
| 41 | 1 | 55 |
| 67 | 1 | 40 |
| 98 | 1 | 45 |
| 101 | 1 | 55 |
| 103 | 1 | 57 |
| 109 | 1 | 66 |
| 115 | 1 | 63 |
| Vitamin C | 10 | 84 |
| Vitamin C | 1 | −11 |

As can be seen from Table 8, the cyclic amide derivatives of the present invention prevent the opacity of the lens of rat caused by irradiation of the ultraviolet rays. From these test results, the cyclic amide derivatives and salts thereof of the present invention are useful as agent for preventing cataract.

We claim:

1. A pharmaceutical composition containing a pharmaceutically acceptable carrier and, as the effective ingredient, a cyclic amide derivative or a salt thereof represented by the general formula (1):

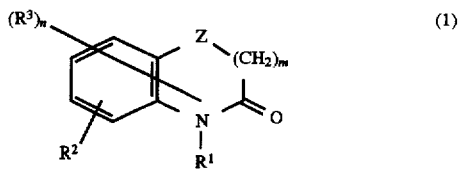

wherein $R^2$ is a hydroxyl group, a lower alkenyloxy group, a phenyl-lower alkenyloxy group, a cycloalkenyloxy group, a tetrahydropyranyloxy group, or a pyridyloxy group;

$R^3$ is a lower alkenyl group;

Z is a group of —$CH_2$— or a group of —CH=CH—;

n is an integer of 1 to 3;

m is 0 or 1; provided that when Z is a group of —$CH_2$—, then m is 1 and when Z is a group of —CH=CH—, then m is 0;

$R^1$ is a hydrogen atom, an alkyl group, an alkenyl group, a phenyl-lower alkenyl group, a cycloalkyl-lower alkyl group, a phenyl group which may have, in the phenyl ring, one or more substituents selected from the group consisting of a lower alkoxy group and a halogen atom, a hydroxyl group-substituted alkyl group, a halogen-substituted lower alkyl group, a cycloalkenyl group; a lower alkynyl group, a phenyl-lower alkyl group which may have, in the phenyl ring, 1 to 3 substituents selected from the group consisting of a lower alkenyloxy group, a lower alkoxy group, a lower alkenyl group, a hydroxyl group, a lower alkyl group, a carboxyl group, a lower alkoxycarbonyl group and a group of the formula:

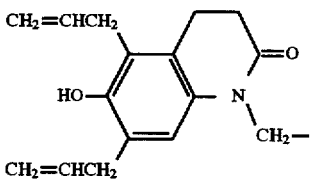

a naphthyl-substituted lower alkyl group, a phthalimido-substituted lower alkyl group, a lower alkoxycarbonyl-substituted lower alkyl group, a group of the formula:

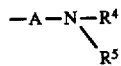

(wherein A is a lower alkylene group; $R^4$ and $R^5$ are the same or different, and are each a hydrogen atom, a carbamoyl group, a lower alkanoyl group which may have one or more halogen atoms, a phenylsulfonyl group which may have, in the phenyl ring, one or more lower alkyl groups as substituents, a lower alkoxy-lower alkyl group, a lower alkyl group, a hydroxyl group-substituted lower alkyl group, a lower alkoxycarbonyl group-substituted lower alkyl group, or a carboxy-substituted lower alkyl group, further $R^4$ and $R^5$ may form a 5- or 6-membered saturated or unsaturated heterocyclic group by combining to each other, together with the adjacent nitrogen atom being bonded thereto, further with or without other nitrogen atom or oxygen atom; said heterocyclic group may have one or more substituents, selected from the group consisting of a carbamoyl group, a carboxyl group, a cycloalkyl group and a phenyl group which may have one or more halogen atoms as substituents in the phenyl ring);

a lower alkanoyloxy-lower alkyl group, a cyano group-substituted lower alkyl group, a group of the formula:

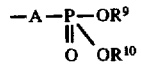

(wherein A is a lower alkylene group; $R^9$ and $R^{10}$ are the same or different, and are each a hydrogen atom or a lower alkyl group), a carboxy-substituted lower alkyl group, a lower alkoxycarbonyl-substituted lower alkyl group or a carbamoyl-substituted lower alkyl group provided that when n is 1, Z is a group of —CH=CH— and $R^1$ is a hydrogen atom, then $R^2$ should not be a hydroxyl group, a lower alkanoyloxy group, a tetrahydropyranyloxy group or a pyridyloxy group.

2. The pharmaceutical composition according to claim 1, containing as the effective ingredient, the cyclic amide derivative or salt thereof represented by the general formula (1), wherein $R^2$ is a hydroxyl group or a lower alkenyloxy group; $R^1$ is an alkyl group, a cycloalkyl-lower alkyl group, a carboxy-substituted lower alkyl group, a carbamoyl-substituted lower alkyl group, an alkenyl group, a lower alkanoyloxy-lower alkyl group, a hydroxyl group-substituted alkyl group, a phenyl-lower alkyl group which may have, in the phenyl ring, 1 to 3 substituents selected from the group consisting of a lower alkenyloxy group, a lower alkoxy group, a lower alkenyl group, a hydroxyl group, a lower alkyl group, a carboxyl group, a lower alkoxycarbonyl group and a group of the formula:

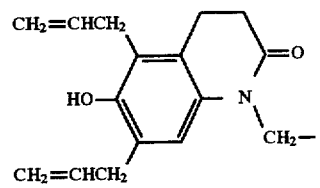

or a group of the formula:

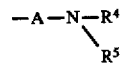

(wherein A is a lower alkylene group; $R^4$ and $R^5$ are the same or different, and are each a hydrogen atom, a carbamoyl group, a lower alkanoyl group which may have halogen atom(s), a phenylsulfonyl group which may have, in the phenyl ring, lower alkyl group(s) as substituent(s), a lower alkoxy-lower alkyl group, a lower alkyl group, a hydroxyl group-substituted lower alkyl group, a lower alkoxycarbonyl group-substituted lower alkyl group, or a carboxy-substituted lower alkyl group; further, $R^4$ and $R^5$ may form a 5- or 6-membered saturated or unsaturated heterocyclic group by combining to each other, together with the adjacent nitrogen atom being bonded thereto, further with or without other nitrogen atom or oxygen atom; said heterocyclic group may have, substituent(s) selected from the group consisting of a carbamoyl group, a carboxyl group, a cycloalkyl group and a phenyl group which may have halogen atom(s) as substituent(s) in the phenyl ring); and n is 2 or 3.

3. The pharmaceutical composition according to claim 1, wherein the effective ingredient is the cyclic amide derivative or salt thereof represented by the general formula (1), selected from the group consisting of:

1-(3-aminopropyl)-5,7-diallyl-3,4-dihydro-6-hydroxy-2 (1H)-quinolinone;

5,7-diallyl-3,4-dihydro-6-hydroxy-1-(2-methylpropyl)-2 (1H)-quinolinone;

1-(cyclohexylmethyl)-5,7-diallyl-3,4-dihydro-6-hydroxy-2(1H)-quinolinone;

(5,7-diallyl-6-hydroxy-1,2,3,4-tetrahydro-2-oxoquinolin-1-yl)acetic acid sodium salt;

1-(carbamoylmethyl)-5,7-diallyl-3,4-dihydro-6-hydroxy-2(1H)-quinolinone;

5,7-diallyl-3,4-dihydro-6-hydroxy-1-prenyl-2(1H)-quinolinone;

2-(5,7-diallyl-6-hydroxy-1,2,3,4-tetrahydro-2-oxoquinolin-1-yl)propionic acid sodium salt;

1-isopropyl-5,7-diallyl-3,4-dihydro-6-hydroxy-2(1H)-quinolinone;

1-octyl-5,7-diallyl-3,4-dihydro-6-hydroxy-2(1H)-quinolinone;

1-(2-acetyloxyethyl)-5,7-diallyl-3,4-dihydro-6-hydroxy-2(1H)-quinolinone;

5,7-diallyl-3,4-dihydro-6-hydroxy-1-(2-hydroxyethyl)-2-(1H)-quinolinone;

5,7-diallyl-3,4-dihydro-6-hydroxy-1-(4-methoxybenzyl)-2(1H)-quinolinone;

1-(3-allyloxybenzyl)-5,7-diallyl-3,4-dihydro-6-hydroxy-2(1H)-quinolinone and 1-(cyclohexylmethyl)-5,7-diallyl-3,4-dihydro-6-hydroxy-2(1H)-quinolinone.

4. A cyclic amide derivative or a salt thereof represented by the general formula (2):

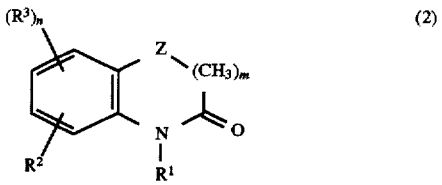

wherein $R^2$ is a hydroxyl group, a lower alkenyloxy group, a phenyl-lower alkenyloxy group, a cycloalkenyloxy group, a tetrahydropyranyloxy group, or a pyridyloxy group;

$R^3$ is a lower alkenyl group;

Z is, a group of —$CH_2$— or a group of —CH=CH—;

n is an integer of 1 to 3;

m is 0 or 1; provided that when Z is a group of —$CH_2$—, then m is 1 and when Z is a group of —CH=CH—, then m is 0;

$R^1$ is a hydrogen atom, an alkyl group, an alkenyl group, a phenyl-lower alkenyl group, a cycloalkyl-lower alkyl group, a phenyl group which may have, in the phenyl ring, one or more substituents selected from the group consisting of a lower alkoxy group and a halogen atom, a hydroxyl group-substituted alkyl group, a halogen-substituted lower alkyl group, a cycloalkenyl group; a lower alkynyl group, a phenyl-lower alkyl group which may have, in the phenyl ring, 1 to 3 substituents selected from the group consisting of a lower alkenyloxy group, a lower alkoxy group, a lower alkenyl group, a hydroxyl group, a lower alkyl group, a carboxyl group, a lower alkoxy-carbonyl group and a group of the formula:

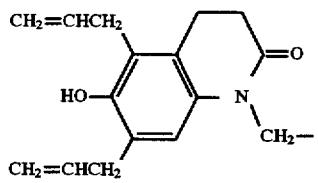

a naphthyl-substituted lower alkyl group, a phthalimido-substituted lower alkyl group, a lower alkoxycarbonyl-substituted lower alkyl group, a group of the formula:

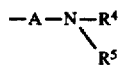

(wherein A is a lower alkylene group; $R^4$ and $R^5$ are the same or different, and are each a hydrogen atom, a carbamoyl group, a lower alkanoyl group which may have one or more halogen atoms, a phenylsulfonyl group which may have, in the phenyl ring, one or more lower alkyl groups as substituents, lower alkoxy-lower alkyl group, a lower alkyl group, a hydroxyl group-substituted lower alkyl group, a lower alkoxycarbonyl group-substituted lower alkyl group, or a carboxy-substituted lower alkyl group; further $R^4$ and $R^5$ may form a 5- or 6-membered saturated or unsaturated heterocyclic group by combining to each other, together with the adjacent nitrogen atom being bonded thereto, further with or without other nitrogen atom or oxygen atom; said heterocyclic group may have one or more substituents selected from the group consisting of a carbamoyl group, a carboxyl group, a cycloalkyl group and a phenyl group which may have one or more halogen atoms as substituents in the phenyl ring);

a lower alkanoyloxy-lower alkyl group, a cyano group-substituted lower alkyl group, a group of the formula:

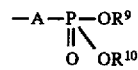

(wherein A is a lower alkylene group; $R^9$ and $R^{10}$ are the same or different, and are each a hydrogen atom or a lower alkyl group), a carboxy-substituted lower alkyl group, a lower alkoxycarbonyl-substituted lower alkyl group or a carbamoyl-substituted lower alkyl group; provided that (i) when n is 1, $R^2$ is OH, Z is a group of —CH=CH— or a group of —$CH_2$— and m is 1, then $R^1$ should not be a hydrogen atom, a lower alkyl group, a lower alkenyl group, a phenyl-lower alkyl group, a phenyl group or a piperidinyl-lower alkyl group;

(ii) when Z is a group of —CH=CH— or a group of —$CH_2$— and m is 1, and $R^2$ is a hydroxyl group which is substituted at 7-position in the formula (2), then $R^1$ should not be a hydrogen atom or a lower alkyl group and;

(iii) when n is 1, Z is a group of —CH=CH— and $R^1$ is a hydrogen atom, then $R^2$ should not be a hydroxyl group, a lower alkanoyloxy group, tetrahydropyranyloxy group or a pyridyloxy group.

5. The cyclic amide derivative or salt thereof according to claim 4, wherein $R^2$ is a hydroxyl group or a lower alkenyloxy group.

6. The cyclic amide derivative or salt thereof according to claim 4, wherein $R^2$ is a phenyl-lower alkenyloxy group, a cycloalkenyloxy group, a tetrahydropyranyloxy group, or a pyridyloxy group.

7. The cyclic amide derivative or salt thereof according to claim 5, wherein $R^1$ is an alkyl group, a cycloalkyl-lower alkyl group, a carboxy-substituted lower alkyl group, a carbamoyl-substituted lower alkyl group, an alkenyl group, a lower alkanoyloxy-lower alkyl group, a hydroxyl group-substituted alkyl group, a phenyl-lower alkyl group which may have, in the phenyl ring, 1 to 3 substituents selected from the group consisting of a lower alkenyloxy group, a lower alkoxy group, a lower alkenyl group, a hydroxyl group, a lower alkyl group, a carboxyl group, a lower alkoxycarbonyl group and a group of the formula:

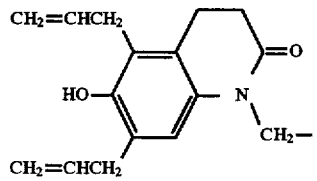

or a group of the formula

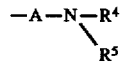

(wherein A is a lower alkylene group; $R^4$ and $R^5$ are the same or different, and are each a hydrogen atom, a carbamoyl group, a lower alkanoyl group which may have halogen atom(s), a phenylsulfonyl group which may have, in the phenyl ring, lower alkyl group(s) as substituent(s), a lower alkoxy-lower alkyl group, a lower alkyl group, a hydroxyl group-substituted lower alkyl group, a lower alkoxycarbonyl-substituted lower alkyl group, or a carboxy-substituted lower alkyl group; further, $R^4$ and $R^5$ may form a 5- or 6-membered saturated or unsaturated heterocyclic group by combining to each other, together with the adjacent nitrogen atom being bonded thereto, further with or without other nitrogen atom or oxygen atom; said heterocyclic group may have, substituent(s) selected from the group consisting of a carbamoyl group, a carboxyl group, a cycloalkyl group and a phenyl group which may have halogen atom(s) as substituent(s) in the phenyl ring).

8. The cyclic amide derivative or salt thereof according to claim 4, wherein $R^1$ is a hydrogen atom, a phenyl-lower alkenyl group, a phenyl group which may have, in the phenyl ring, substituent(s) selected from the group consisting of a lower alkoxy group and a halogen atom, a halogen-substituted lower alkyl group, a cycloalkenyl group, a lower alkynyl group, a naphthyl-substituted lower alkyl group, a phthalimido-substituted lower alkyl group, a lower alkoxycarbonyl-substituted lower alkyl group, a cyano group-substituted lower alkyl group, a group of the formula:

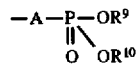

(wherein A is a lower alkylene group; $R^9$ and $R^{10}$ are the same or different, and are each a hydrogen atom or a lower alkyl group), or a lower alkoxycarbonyl-substituted lower alkyl group.

9. The cyclic amide derivative or salt thereof according to claim 6, wherein $R^1$ is an alkyl group, a cycloalkyl-lower alkyl group, a carboxy-substituted lower alkyl group, a carbamoyl-substituted lower alkyl group, an alkenyl group, a lower alkanoyloxy-lower alkyl group, a hydroxyl group-substituted alkyl group, a phenyl-lower alkyl group which may have, in the phenyl ring, 1 to 3 substituents selected from the group consisting of a lower alkenyloxy group, a lower alkoxy group, a lower alkenyl group, a hydroxyl group, a lower alkyl group, a carboxyl group, a lower alkoxycarbonyl group and a group of the formula:

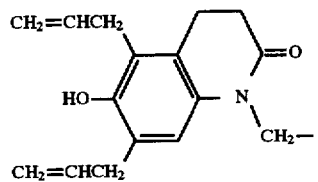

or a group of the formula

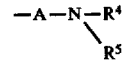

(wherein A is a lower alkylene group; $R^4$ and $R^5$ are the same or different, and are each a hydrogen atom, a carbamoyl group, a lower alkanoyl group which may have halogen atom(s), a phenylsulfonyl group which may have, in the phenyl ring, lower alkyl group(s) as substituent(s), a lower alkoxy-lower alkyl group, a lower alkyl group, a hydroxyl group-substituted lower alkyl group, a lower alkoxycarbonyl-substituted lower alkyl group, or a carboxy-substituted lower alkyl group; further, $R^4$ and RI may form a 5- or 6-membered saturated or unsaturated heterocyclic group by combining to each other, together with the adjacent nitrogen atom being bonded thereto, further with or without other nitrogen atom or oxygen atom; said heterocyclic group may have, substituent(s) selected from the group consisting of a carbamoyl group, a carboxyl group, a cycloalkyl group and a phenyl group which may have halogen atom(s) as substituent(s) in the phenyl ring).

10. The cyclic amide derivative or salt thereof according to claim 6, wherein $R^1$ is a hydrogen atom, a phenyl-lower alkenyl group, a phenyl group which may have, in the phenyl ring, substituent(s) selected from the group consisting of a lower alkoxy group and a halogen atom, a halogen-substituted lower alkyl group, a cycloalkenyl group, a lower alkynyl group, a naphthyl-substituted lower alkyl group, a phthalimido-substituted lower alkyl group, a lower alkoxycarbonyl-substituted lower alkyl group, a cyano group-substituted lower alkyl group, a group of the formula:

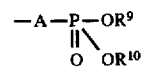

(wherein A is a lower alkylene group; $R^9$ and $R^{10}$ are the same or different, and are each a hydrogen atom or a lower alkyl group), or a lower alkoxycarbonyl-substituted lower alkyl group.

11. The cyclic amide derivative or salt thereof according to claim 7, wherein $R^1$ is a group of the formula:

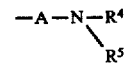

(wherein A is a lower alkylene group; $R^4$ and $R^5$ are the same or different, and are each a hydrogen atom, a carbamoyl group, a lower alkanoyl group which may have halogen atom(s), a phenylsulfonyl group which may have, in the phenyl ring, lower alkyl group(s) as substituent(s), a lower alkoxy-lower alkyl group, a lower alkyl group, a hydroxyl group-substituted lower alkyl group, a lower alkoxycarbonyl-substituted lower alkyl group, or a carboxy-substituted lower alkyl group).

12. The cyclic amide derivative or salt thereof according to claim 7, wherein $R^1$ is a group of the formula:

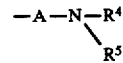

(wherein A is a lower alkylene group; $R^4$ and $R^5$ may form a 5- or 6-membered saturated or unsaturated heterocyclic group by combining to each other, together with the adjacent nitrogen atom being bonded thereto, further with or without other nitrogen atom or oxygen atom; said heterocyclic group may have, substituent(s) selected from the group consisting of a carbamoyl group, a carboxyl group, a cycloalkyl group and a phenyl group which may have halogen atom(s) as substituent(s) in the phenyl ring).

13. The cyclic amide derivative or salt thereof according to claim 11, wherein n is 1.

14. The cyclic amide derivative or salt thereof according to claim 11, wherein n is 2 or 3.

15. The cyclic amide derivative or salt thereof according to claim 8, wherein n is 1.

16. The cyclic amide derivative or salt thereof according to claim 8, wherein n is 2 or 3.

17. The cyclic amide derivative or salt thereof according to claim 4, which is selected from the group consisting of:

1-(3-aminopropyl)-5,7-diallyl-3,4-dihydro-6-hydroxy-2(1H)-quinolinone;

5,7-diallyl-3,4-dihydro-6-hydroxy-1-(2-methylpropyl)-2(1H)-quinolinone;

1-(cyclohexylmethyl)-5,7-diallyl-3,4-dihydro-6-hydroxy-2(1H)-quinolinone;

(5,7-diallyl-6-hydroxy-1,2,3,4-tetrahydro-2-oxoquinolin-1-yl)acetic acid sodium salt;

1-(carbamoylmethyl)-5,7-diallyl-3,4-dihydro-6-hydroxy-2(1H)-quinolinone and 5,7-diallyl-3,4-dihydro-6-hydroxy-1-prenyl-2(1H)-quinolinone.

18. The cyclic amide derivative or salt thereof according to claim 4, which is selected from the group consisting of:

2-(5,7-diallyl-6-hydroxy-1,2,3,4-tetrahydro-2-oxoquinolin-1-yl)propionic acid sodium salt;

1-isopropyl-5,7-diallyl-3,4-dihydro-6-hydroxy-2(1H)-quinolinone;

1-octyl-5,7-diallyl-3,4-dihydro-6-hydroxy-2(1H)-quinolinone;

1-(2-acetyloxyethyl)-5,7-diallyl-3,4-dihydro-6-hydroxy-2(1H)-quinolinone;

5,7-diallyl-3,4-dihydro-6-hydroxy-1-(2-hydroxyethyl)-2(1H)-quinolinone;

5,7-diallyl-3,4-dihydro-6-hydroxy-1-(4-methoxybenzyl)-2(1H)-quinolinone;

1-(3-allyloxybenzyl)-5,7-diallyl-3,4-dihydro-6-hydroxy-2(1H)-quinolinone and 1-(cyclohexylmethyl)-5,7-diallyl-3,4-dihydro-6-hydroxy-2(1H)-quinolinone.

19. A method for preventing or treating cataract or erythema by administering the pharmaceutical composition according to claim 2.

20. A method for preventing or treating cataract or erythema by administering the pharmaceutical.

21. A method for preventing or treating cataract or erythema by administering a pharmaceutical composition containing a pharmaceutically acceptable carrier and, as the effective ingredient, a cyclic amide derivative or a salt thereof represented by the formula (1):

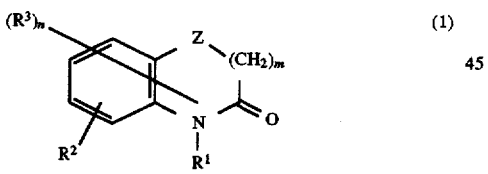

wherein $R^2$ is a hydroxyl group, a lower alkenyloxy group, a phenyl-lower alkenyloxy group, a cycloalkenyloxy group, a tetrahydropyranyloxy group, or a pyridyloxy group;

$R^3$ is a lower alkenyl group;

Z is a group of —$CH_2$— or a group of —CH=CH—;

n is an integer of 1 to 3;

m is 0 or 1; provided that when Z is a group of —$CH_2$— then m is 1 and when Z is a group of —CH=CH—, then m is 0;

$R^1$ is a hydrogen atom, an alkyl group, an alkenyl group, a phenyl-lower alkenyl group, a cycloalkyl-lower alkyl group, a phenyl group which may have, in the phenyl ring, one or more substituents selected from the group consisting of a lower alkoxy group and a halogen atom, a hydroxyl group-substituted alkyl group, a halogen-substituted lower alkyl group, a cycloalkenyl group; a lower alkynyl group, a phenyl-lower alkyl group which may have, in the phenyl ring, 1 to 3 substituents selected from the group consisting of a lower alkenyloxy group, a lower alkoxy group, a lower alkenyl group, a hydroxyl group, a lower alkyl group, a carboxyl group, a lower alkoxycarbonyl group and a group of the formula:

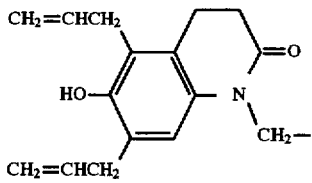

a naphthyl-substituted lower alkyl group, a phthalimido-substituted lower alkyl group, a lower alkoxycarbonyl-substituted lower alkyl group, a group of the formula:

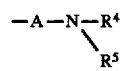

(wherein A is a lower alkylene group; $R^4$ and $R^5$ are the same or different, and are each a hydrogen atom, a carbamoyl group, a lower alkanoyl group which may have one or more halogen atoms, a phenylsulfonyl group which may have, in the phenyl ring, one or more lower alkyl groups as substituents, a lower alkoxy-lower alkyl group, a lower alkyl group, a hydroxyl group-substituted lower alkyl group, a lower alkoxycarbonyl group-substituted lower alkyl group, or a carboxy-substituted lower alkyl group; further $R^4$ and $R^1$ may form a 5- or 6-membered saturated or unsaturated hereocyclic group by combining to each other, together with the adjacent nitrogen atom being bonded thereto, further with or without other nitrogen atom or oxygen atom; said heterocyclic group may have one or more-substituents selected from the group consisting of a carbamoyl group, a carboxyl group, a cycloalkyl group and a phenyl group which may have one or more halogen atoms as substituents in the phenyl ring);

a lower alkanoyloxy-lower alkyl group, a cyano group-substituted lower alkyl group, a group of the formula:

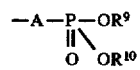

(wherein A is a lower alkylene group; $R^9$ and $R^{10}$ are the same or different, and are each a hydrogen atom or a lower alkyl group), a carboxy-substituted lower alkyl group, a lower alkoxycarbonyl-substituted lower alkyl group or a carbamoyl-substituted lower alkyl group.

22. The pharmaceutical composition of claim 1, wherein $R^2$ is a hydroxyl group, a lower alkenyloxy group, a phenyl-lower alkenyloxy group, a cycloalkenyloxy group or a tetrahydropyranyloxy group; Z is a group of —$CH_2$—; and m is 1.

23. The cyclic amide derivative or a salt thereof of claim 4, wherein $R^2$ is a hydroxyl group, a lower alkenyloxy group, a phenyl-lower alkenyloxy group, a cycloalkenyloxy group or a tetrahydropyranyloxy group; Z is a group of —$CH_2$—; and m is 1.

* * * * *

UNITED STATES PATENT AND TRADEMARK OFFICE
CERTIFICATE OF CORRECTION

PATENT NO. : 5,786,367
DATED : July 28, 1998
INVENTOR(S) : Yasuo Oshiro et al.

It is certified that error appears in the above-indentified patent and that said Letters Patent is hereby corrected as shown below:

Column 63, claim 8, line 2, "claim 4" should read --claim 5--.

Column 65, claim 20, line 2, after "pharmaceutical" insert --composition according to claim 3--.

Column 66, claim 21, line 34, "$R^1$" should read --$R^5$--.

Signed and Sealed this

Twenty-second Day of June, 1999

Attest:

Q. TODD DICKINSON

Attesting Officer     Acting Commissioner of Patents and Trademarks